United States Patent
Tai

(10) Patent No.: US 11,794,009 B2
(45) Date of Patent: Oct. 24, 2023

(54) DEVICES, SYSTEMS AND METHODS FOR TREATING UROLOGICAL AND GASTROINTESTINAL DISORDERS BY ELECTRICAL STIMULATION OF THE FOOT

(71) Applicant: University of Pittsburgh—Of the Commonwealth System of Higher Education, Pittsburgh, PA (US)

(72) Inventor: Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 127 days.

(21) Appl. No.: 17/318,110

(22) Filed: May 12, 2021

(65) Prior Publication Data
US 2021/0370059 A1 Dec. 2, 2021

Related U.S. Application Data

(62) Division of application No. 15/539,503, filed as application No. PCT/US2015/067017 on Dec. 21, 2015, now abandoned.
(Continued)

(51) Int. Cl.
*A61N 1/36* (2006.01)
*A61K 31/137* (2006.01)
(Continued)

(52) U.S. Cl.
CPC ........ *A61N 1/36007* (2013.01); *A61K 31/137* (2013.01); *A61K 31/381* (2013.01);
(Continued)

(58) Field of Classification Search
CPC .............. A61N 1/36007; A61N 1/0456; A61N 1/0492; A61N 1/36021
See application file for complete search history.

(56) References Cited

U.S. PATENT DOCUMENTS

| 3,881,494 A | 5/1975 | Paul, Jr. |
| 3,902,502 A | 9/1975 | Iss et al. |

(Continued)

FOREIGN PATENT DOCUMENTS

| WO | 2006113468 A2 | 10/2006 |
| WO | 2014151431 A2 | 9/2014 |

OTHER PUBLICATIONS

Schwen Z, Matsuta Y, Shen B, Wang J, Roppolo JR, de Groat WC, Tai C. Inhibition of bladder overactivity by duloxetine in combination with foot stimulation or WAY-100635 treatment in cats. Am J Physiol Renal Physiol. 2013; 305: F1663-F1668 doi: 10.1152/ajprenal.00523.2013 pmid: 24154699 (Year: 2013).*
(Continued)

*Primary Examiner* — Eric D. Bertram
(74) *Attorney, Agent, or Firm* — The Webb Law Firm

(57) ABSTRACT

Provided herein are devices, systems, and methods for treating urological and gastrointestinal disorders, including bedwetting, through stimulation of the dorsal or plantar surface of the foot, including the superficial peroneal nerve and branches thereof, such as the dorsal intermediate and medial cutaneous nerves, or the medial and/or and lateral plantar nerves. The device facilitates placement of electrodes on the foot. Also provided herein is a system including the device, a pulse generator, and a controller, and methods of manufacturing and using the same.

18 Claims, 25 Drawing Sheets

Related U.S. Application Data

(60) Provisional application No. 62/235,849, filed on Oct. 1, 2015, provisional application No. 62/096,226, filed on Dec. 23, 2014, provisional application No. 62/096,265, filed on Dec. 23, 2014.

(51) Int. Cl.

| | | |
|---|---|---|
| *A61N 1/04* | (2006.01) | |
| *A61N 1/372* | (2006.01) | |
| *A61K 31/428* | (2006.01) | |
| *A61N 1/18* | (2006.01) | |
| *A61K 31/435* | (2006.01) | |
| *A61N 1/24* | (2006.01) | |
| *A61N 1/32* | (2006.01) | |
| *A61K 31/381* | (2006.01) | |

(52) U.S. Cl.
CPC .......... *A61K 31/428* (2013.01); *A61K 31/435* (2013.01); *A61N 1/04* (2013.01); *A61N 1/0456* (2013.01); *A61N 1/0484* (2013.01); *A61N 1/0492* (2013.01); *A61N 1/18* (2013.01); *A61N 1/24* (2013.01); *A61N 1/32* (2013.01); *A61N 1/3603* (2017.08); *A61N 1/36021* (2013.01); *A61N 1/372* (2013.01); *A61N 1/37264* (2013.01); *A61N 1/36034* (2017.08)

(56) References Cited

U.S. PATENT DOCUMENTS

| | | | |
|---|---|---|---|
| 4,454,883 A | 6/1984 | Ellus | |
| 4,930,504 A * | 6/1990 | Diamantopoulos | A61N 5/0616 250/494.1 |
| 5,273,033 A | 12/1993 | Hoffman | |
| 5,326,272 A | 7/1994 | Harhen et al. | |
| 5,330,516 A * | 7/1994 | Nathan | A61N 1/36003 607/48 |
| 5,368,043 A * | 11/1994 | Sunouchi | A61B 5/394 600/590 |
| 5,766,236 A * | 6/1998 | Detty | A61N 1/321 607/152 |
| 6,341,237 B1 * | 1/2002 | Hurtado | A61N 1/36003 607/148 |
| 6,615,080 B1 | 9/2003 | Unsworth et al. | |
| 6,701,185 B2 | 3/2004 | Burnett et al. | |
| 6,862,481 B1 * | 3/2005 | Demian | A61N 1/36021 607/144 |
| 6,889,088 B2 * | 5/2005 | Demian | A61N 1/36021 607/144 |
| 7,047,078 B2 | 5/2006 | Boggs et al. | |
| 7,678,821 B2 | 3/2010 | Paborji | |
| 7,683,168 B2 | 3/2010 | Jan et al. | |
| 8,435,166 B2 | 5/2013 | Burnett et al. | |
| 9,878,154 B2 | 1/2018 | Tai | |
| 10,315,029 B2 | 6/2019 | Tai | |
| 2004/0044384 A1 * | 3/2004 | Leber | A61N 5/0619 607/96 |
| 2004/0248979 A1 | 12/2004 | Brettman et al. | |
| 2004/0254624 A1 | 12/2004 | Johnson | |
| 2005/0143783 A1 | 6/2005 | Boveja et al. | |
| 2008/0033510 A1 | 2/2008 | Herregraven et al. | |
| 2008/0306325 A1 | 12/2008 | Burnett et al. | |
| 2009/0036945 A1 | 2/2009 | Chancellor et al. | |
| 2010/0145413 A1 | 6/2010 | Brogan et al. | |
| 2010/0204538 A1 | 8/2010 | Burnett et al. | |
| 2011/0178572 A1 * | 7/2011 | Czyrny | A61N 1/36031 607/46 |
| 2011/0270140 A1 | 11/2011 | Israeli | |
| 2012/0101326 A1 | 4/2012 | Simon et al. | |
| 2012/0289560 A1 | 11/2012 | Paborji et al. | |
| 2012/0289565 A1 | 11/2012 | Paborji et al. | |
| 2013/0006322 A1 * | 1/2013 | Tai | A61N 1/36007 607/40 |
| 2014/0046423 A1 * | 2/2014 | Rajguru | A61N 2/02 607/144 |
| 2014/0277326 A1 * | 9/2014 | Rhodes | A61N 1/36025 607/148 |
| 2015/0148878 A1 * | 5/2015 | Yoo | A61N 1/0456 607/148 |

OTHER PUBLICATIONS

Andersson et al., "Pharmacology of the Lower Urinary Tract: Basis for Current and Future Treatments of Urinary Incontinence", Pharmacological Review, 2004, pp. 581-631, vol. 56, No. 4.

Beringer et al., "The Science and Practice of Pharmacy", Remington, 2005, Ch. 37, 39, 41, 42, and 45, 21st Ed.

Bjorvatn et al., "Venlafaxine and its Interaction with WAY100635: Effects on Serotonergic Unit Activity and Behavior in Cats", European Journal of Pharmacology, 2000, pp. 121-132, vol. 404.

Bower et al., "PinQ: A Valid, Reliable and Reproducible Quality-of-Life Measure in Children with Bladder Dysfunction", Journal of Pediatric Urology, 2006, pp. 185-189, vol. 2.

Chen et al., "Electrical Stimulation of Somatic Afferent Nerves in the Foot Increase Bladder Capacity in Healthy Human Subjects", The Journal of Urology, 2014, pp. 1009-1013, vol. 191.

Chen et al., "Post-Stimulation Inhibitory Effect on Reflex Bladder Activity Induced by Activation of Somatic Afferent Nerves in the Foot", The Journal of Urology, 2012, pp. 338-343, vol. 187.

De Groat et al., "Developmental and Injury Induced Plasticity in the Micturition Reflex Pathway", Behavioral Brain Research, 1998, pp. 127-140, vol. 92.

George et al., "Use of Combined Anticholinergic Medication and Sacral Neuromodulation in the Treatment of Refractory Overactive Bladder", Female Pelvic Medicine & Reconstructive Surgery, 2011, pp. 97-99, vol. 17, No. 2.

Godec et al., "Bladder Inhibition with Functional Electrical Stimulation", Urology, 1975, pp. 663-666, vol. 6.

Godec, "Electrical Stimulation for Incontinence: Technique, Selection and Results", Urology, 1976, pp. 388-397, vol. 7, No. 4.

Grond et al., "Clinical Pharmacology of Tramadol", Clin Pharmacokinet, 2004, pp. 879-923, vol. 43.

Lindstrom et al., "The Neurophysiological Basis of Bladder Inhibition in Response to Intravaginal Electrical Stimulation", The Journal of Urology, 1983, pp. 405-410, vol. 129.

Mally et al., "Combination of Foot Stimulation and Tramadol Treatment Reverses Irritation Induced Bladder Overactivity in Cats", The Journal of Urology, 2012, pp. 2426-2432, vol. 188.

Marchand et al., "Blockade of Supraspinal 5-HT(1A) Receptors Potentiates the Inhibitory Effect of Venlafaxine on Wind-up Activity in Mononeuropathic Rats", Brain Research, 2004, pp. 288-292, vol. 1008.

McGuire et al., "Treatment of Motor and Sensory Detrusor Instability by Electrical Stimulation", The Journal of Urology, 1983, pp. 78-79, vol. 129.

McPherson, "The Effects of Somatic Stimuli on the Bladder in the Cat", The Journal of Physiology, 1966, pp. 185-196, vol. 185.

Nakamura et al., "Bladder Inhibition by Electrical Stimulation of the Perianal Skin", 1986, pp. 62-63, vol. 41.

Nakib et al., "Neuromodulation versus Neurotoxin for the Treatment of Refractory Detrusor Overactivity: for Neuromodulation", Nature Clinical Practice Urology, 2008, pp. 118-119, vol. 5, No. 3.

Peters et al., "Sacral Versus Pudendal Nerve Stimulation for Voiding Dysfunction: A Prospective Single-Blinded, Randomized, Crossover Trial", Neurourology and Urodynamics, 2005, pp. 643-647, vol. 24.

Peters et al., "Randomized Trial of Percutaneous Tibial Nerve Stimulation Versus Extended-Release Tolterodine: Results From the Overactive Bladder Innovative Therapy Trial", The Journal of Urology, 2009, pp. 1055-1061, vol. 182.

Peters et al., "A Prospective, Single-Blind, Randomized Crossover Trial of Sacral vs Pudendal Nerve Stimulation for Interstitial Cystitis", Journal Compilation, 2007, pp. 835-839, vol. 100.

(56) References Cited

OTHER PUBLICATIONS

Queralto et al., "Preliminary Results of Peripheral Transcutaneous Neuromodulation in the Treatment of Idiopathic Fecal Incontinence", International Journal of Colorectal Disease, 2006, pp. 670-672, vol. 21.
Sato et al., "Reflex Bladder Activity Induced by Electrical Stimulation of Hind Limb Somatic Afferents in the Cat", Journal of the Autonomic Nervous System, 1980, pp. 229-241, vol. 1.
Schulpen, "The Burden of Nocturnal Enuresis", Acta Paediatrica, 1997, pp. 981-984, vol. 86.
Schwen et al., "Combination of Foot Stimulation and Tolterodine Treatment Eliminates Bladder Overactivity in Cats", Neurourology and Urodynamics, 2014, pp. 1266-1271, vol. 33.
Schwen et al., "Inhibition of Bladder Overactivity by Duloxetine in Combination with Foot Stimulation or WAY-100635 Treatment in Cats", American Journal of Physiology Renal Physiology, 2013, pp. F1663-F1668, vol. 305.
Shen et al., "Bladder Activity Modulated by Transcutaneous Pudendal Nerve Stimulation", Neuroscience, 2008, pp. 1-2, https://www.abstractsonline.com/Plan/AbstractPrintView . . . .
Sutherland et al., "Sacral Nerve Stimulation for Voiding Dysfunction: One Institution's 11-Year Experience", Neurourology and Urodynamics, 2007, pp. 19-28, vol. 26.
Tai et al., "Suppression of Bladder Reflex Activity in Chronic Spinal Cord Injured Cats by Activation of Serotonin 5-HT (1A) Receptors", Experimental Neurology, 2006, pp. 427-437, vol. 199.
Tai et al., "Inhibitory and Excitatory Perigenital-to-Bladder Spinal Reflexes in the Cat", American Journal of Physiology Renal Physiology, 2007, pp. F591-F602, vol. 294.
Tai et al., "Pudendal-to-Bladder Reflex in Chronic Spinal-Cord Injured Cats", Experimental Neurology, 2006, pp. 225-234, vol. 197.
Thor, "Serotonin and Norepinephrine Involvement in Efferent Pathways to the Urethral Rhabdosphincter: Implications for Treating Stress Urinary Incontinence", Urology, 2003, pp. 3-9, vol. 62, Supplemental 4A.
Van Balken, "Percutaneous Tibial Nerve Stimulation: The Urgent PC.sup.[R] device", Expert Review of Medical Devices, 2007, p. 693 (14 pages), vol. 4.5, https://sremote.pitt.edu/ps/,DanaInfo=go.gale . . . .
Van Der Pal et al., "Percutaneous Tibial Nerve Stimulation in the Treatment of Refractory Overactive Bladder Syndrome: Is Maintenance Treatment Necessary?", BJU International, 2006, pp. 547-550, vol. 97.
Vitton et al., "Transcutaneous Posterior Tibial Nerve Stimulation for Fecal Incontinence in Inflammatory Bowel Disease Patients: A Therapeutic Option?", Inflammatory Bowel Disease, 2009, pp. 402-405, vol. 15, No. 3.
Walter et al. "Inhibiting the Hyperreflexic Bladder With Electrical Stimulation in a Spinal Animal Mode", Neurourology and Urodynamics, 1993, pp. 241-253, vol. 12.
Wang et al., "Bladder Inhibition or Excitation by Electrical Perianal Stimulation in a Cat Model of Chronic Spinal Cord Injury", Journal Compilation, 2008, pp. 530-536, vol. 103.
Wheeler et al., "Bladder Inhibition by Penile Nerve Stimulation in Spinal Cord Injury Patients", The Journal of Urology, 1992, pp. 100-103, vol. 147.
PCT International Report on Patentability re: PCT/US2015/067017.

* cited by examiner (a)

(b)

| | Week 1 (7 days) | Week 2-3 (7 days) | Number of Responders (%) | p value |
|---|---|---|---|---|
| Voiding Frequency (voids/day) | 10±0.4 | 8.5±0.4 | 8 (50%) | 0.0044* |
| Volume (mL/void) | 187±10 | 217±10 | | 0.0465* |
| Incontinence Frequency (episodes/day) | 3.5±0.4 | 1.4±0.3 | 8 (50%) | 0.0001* |
| Severity (per void) | 1.7±0.04 | 1.3±0.1 | | 0.0006* |
| Urgency Frequency (episodes/day) | 8.5±0.4 | 6.2±0.4 | 11 (69%) | $P < 0.0001$* |
| Strength (per void) | 1.2±0.1 | 0.8±0.1 | | 0.0011* |
| Nocturia (episodes/day) | 1.8±0.1 | 1.0±0.1 | 7 (44%) | 0.0001* |

*Fig. 26*

| N = 15 | W3 | W4 |
|---|---|---|
| Number of values | 15 | 14 |
| Minimum | 12.00 | 12.00 |
| Maximum | 28.86 | 45.14 |
| Mean | 18.99 | 21.08 |
| Std. Deviation | 3.817 | 7.702 |
| Std. Error | 0.9855 | 2.058 |

DEVICES, SYSTEMS AND METHODS FOR TREATING UROLOGICAL AND GASTROINTESTINAL DISORDERS BY ELECTRICAL STIMULATION OF THE FOOT

CROSS-REFERENCE TO RELATED APPLICATIONS

This application is a divisional of U.S. patent application Ser. No. 15/539,503, filed Jun. 23, 2017, which is the National Stage of International Patent Application No. PCT/US2015/067017, filed Dec. 21, 2015, which claims the benefit of U.S. Provisional Patent Application Nos. 62/096,226, filed Dec. 23, 2014, 62/096,265, filed Dec. 23, 2014, and 62/235,849, filed Oct. 1, 2015, each of which is incorporated herein by reference in its entirety.

STATEMENT REGARDING FEDERALLY SPONSORED RESEARCH OR DEVELOPMENT

This invention was made with government support under Grant Nos. DK-068566, DK-090006, and DK-094905 awarded by the National Institutes of Health. The government has certain rights in the invention.

BACKGROUND

Overactive bladder (OAB) is a syndrome characterized by urinary urgency with or without urge incontinence, often with frequency and nocturia. OAB patients have a significantly impaired quality of life. First line therapy involves such behavioral therapies as fluid management, pelvic floor muscle physical therapy, and bladder training. Pharmacotherapy is offered concomitantly or subsequently if behavioral strategies fail. Anti-muscarinics are the most common drugs used for OAB treatment. However, drug therapy often has low efficacy and significant adverse effects. Consequently, 70% of patients discontinue therapy within the first year of treatment.

FDA-approved treatments for patients that have failed behavioral and anti-muscarinic therapies include intradetrusor injection of onabotulinumtoxinA, sacral neuromodulation, or tibial neuromodulation. OnabotulinumtoxinA requires repeat injections every 6-12 months and results in adverse events such as urinary tract infection and urinary retention. Sacral neuromodulation is invasive, requiring surgery to implant both the electrodes and the neurostimulator. Furthermore, the costs associated with sacral neuromodulation have limited this option for some OAB patients. Tibial neuromodulation is a minimally invasive, office-based procedure that involves inserting a needle electrode near the ankle to stimulate the tibial nerve. The tibial nerve is stimulated for 30 minutes each week for 12 consecutive weeks, followed by one stimulation per month to maintain efficacy.

Additionally, nocturnal enuresis, or bedwetting at night, is a very common problem of childhood. The American Psychiatric Association defines nocturnal enuresis as wetting two or more times per week for at least three consecutive months in children over the age of five. About 80% of the bedwetting children have never achieved nighttime dryness for a period more than 6 months. The other 20% children have bedwetting re-appear after achieving more than 6 months of nighttime dryness. Most bedwetting children (80%) are healthy without known lower urinary tract diseases. The pathology and etiology underlying bedwetting is not fully understood. Current treatment options for effectively and safely curing bedwetting are cumbersome and most are not readily effective.

Behavioral therapy and bedwetting alarms are the first-line treatments for bedwetting. Although behavioral therapy can reduce the frequency of bedwetting, its efficacy is very limited. Further, while alarm training is an effective treatment, it can produce a significant amount of stress to the child and family due to disruptions of nighttime sleep, especially to a family with crowded housing or intolerance to sleep disturbance. Other problems in using a bedwetting alarm include the difficulties in setting up each night, failure of the alarm to wake the child, false alarm, alarm failure, and skin irritation. Due to these problems, many children and families either decline or discontinue the use of bedwetting alarms.

Medications are used to treat the symptoms of bedwetting after behavioral and alarm therapies do not produce beneficial effects, but medications, such as imipramine and desmopressin, do not cure bedwetting. At present, a safe, effective, and easy-to-use treatment for bedwetting in children is not available.

Several non-invasive neuromodulation approaches have been investigated previously in an attempt to treat bladder overactivity (but heretofore have not been tested for bed wetting), including intra-vaginal simulation. However, these approaches targeted very inconvenient locations causing discomfort and difficulty in maintaining the electrodes in place for an extended time period. Accordingly, a need exists in the art for a device, system, and method of using the same for non-invasive, non-painful stimulation of nerves that can modulate urological and gastrointestinal activity and treat urological (including bed wetting) and gastrointestinal disorders in humans.

SUMMARY

The devices, systems, and methods described herein are useful for stimulating a physiological response and for inhibiting or treating conditions, such as overactive bladder (OAB) symptoms including bladder overactivity, urinary frequency, urinary urgency, urinary incontinence (including without limitation bedwetting, a type of urinary incontinence), interstitial cystitis (IC), urinary retention, and pelvic pain; and gastrointestinal conditions, such as fecal incontinence, irritable bowel syndrome (IBS), and constipation.

The present devices, systems, and methods are superior to prior methods because they do not involve invasive activities, such as electrode implantation, for instance, as is currently used for urinary incontinence, and do not require precise placement of the electrodes. The devices, systems, and methods disclosed herein involve electrical stimulation applied to the skin of the dorsal or plantar surface of the foot of a patient, unexpectedly being able to inhibit bladder contractions in a non-invasive manner that is easily implemented by patients and which is amenable to comfortable placement and stimulation by electrodes in foot orthotics, thin films (rigid or flexible) and other devices that can comfortably fit on the patient's foot, greatly enhancing patient independence and reducing costs of such procedures. The following are exemplary aspects, illustrative of the devices, systems and methods described herein. It should be noted that the devices, systems, and methods described herein apply equally to the left and right foot, and the methods may stimulate the right foot, the left foot, alternate stimulation, and/or stimulate both feet at the same time.

Provided herein is an electrode-containing device. In one aspect, the device includes a base adapted to cover a portion of a plantar surface of a human foot including a portion of the forefoot overlaying a plurality of branches of the medial or lateral plantar nerves and a portion of the hindfoot overlaying the medial and lateral plantar nerves; a first electrode attached to the base at a position adapted to the hindfoot to contact skin overlaying the medial and lateral plantar nerves; a second electrode attached to the base at a position adapted to the forefoot to contact skin overlaying a plurality of branches of the medial or lateral plantar nerves in the forefoot; and a first and second electrical lead attached to the first and second electrodes, respectively.

In another aspect, the device includes a base adapted to cover a portion of a dorsal surface of a human foot including a portion of the forefoot overlaying a plurality of branches of the dorsal intermediate and medial cutaneous nerves, deep peroneal nerve, sural nerve, and/or saphenous nerve, and a portion of the hindfoot overlaying the superficial peroneal nerve, deep peroneal nerve, and/or saphenous nerve; a first electrode attached to the base at a position adapted to a dorsal portion of the hindfoot to contact skin overlaying the superficial peroneal nerve, deep peroneal nerve, and/or saphenous nerve; a second electrode attached to the base at a position adapted to a dorsal portion of the forefoot to contact skin overlaying a plurality of branches of the dorsal intermediate and medial cutaneous nerves, deep peroneal nerve, sural nerve, and/or saphenous nerve in the forefoot; and a first and second electrical lead attached to the first and second electrodes, respectively.

In aspects, the first electrode of the device is a cathode and the second electrode is an anode. In some aspects, the first electrode is an anode and the second electrode is a cathode.

In aspects, the first electrode or the second electrode overlays at least 50% of the width of the sole at the forefoot.

In aspects, the first electrode overlays at least a portion of the metatarsophalangeal joint. In some aspects, the second electrode overlays at least a portion of the metatarsophalangeal joint.

In aspects, the first electrode overlays at least a portion of the calcaneus bone. In some aspects, the second electrode overlays at least a portion of the calcaneus bone.

In aspects, the first electrode overlays a predominance of branches of the medial and lateral plantar nerves in the forefoot. In some aspects, the second electrode overlays a predominance of branches of the medial and lateral plantar nerves in the forefoot.

In aspects, the base of the device has a perimeter having the shape of a sole of a foot, and optionally is an orthotic insert. In some aspects, the base has a perimeter having the shape of the dorsal area of a foot from the proximal phalanges to the talocrural joint.

In aspects, the base of the device is a thin polymeric film having an adhesive on a side comprising the electrodes and facing the foot.

In aspects, the device further includes one or more connectors for an external pulse generator attached to the leads.

In aspects, the device further includes an adhesive on a surface of the base and/or electrodes for removably securing the device to a patient's foot.

In aspects, the base of the device is shaped substantially like a plantar surface or sole of a human foot. In some aspects, the base is shaped substantially to interact with the dorsal surface of a human foot.

Also provided herein is an electrical nerve stimulation system. In aspects, the system includes a device as described herein and a pulse generator external to the electrode-containing device and connected to the leads, configured to generate pulses of pulsewidth 0.01-3 ms between 1-100 V and 1-100 mA, at frequency 1-50 Hz.

In aspects, the system includes an adjustment mechanism for adjusting one or more parameters of the pulses. In aspects, the adjustment mechanism includes a wireless receiver in wireless communication with a wireless controller.

In aspects, the pulse generator of the system produces monophasic, rectangular pulses or biphasic pulses. In some aspects, the pulse generator provides pulses having a pulsewidth of 0.2 ms at 5 Hz, and wherein the intensity of the pulses is from 2-6 times a toe twitch threshold of a patient. In some aspects, the pulse generator provides a fixed output of pulses of pulsewidth 0.01-3 ms between 1-100 V and 1-100 mA, at frequency 1-50 Hz.

Also provided herein is a method of treating urological or gastrointestinal disorders. In aspects, the method includes the steps of applying an electrode-containing device as described herein to a foot of a patient in need of such treatment, wherein the electrode-containing device is attached to a pulse generator external to the electrode-containing device comprising a connector for connecting the pulse generator to the device; and stimulating the patient's foot with the device with pulses of pulsewidth 0.01-3 ms between 1-100 V and 1-100 mA, at frequency 1-50 Hz, thereby stimulating either the lateral and/or medial plantar nerves or the dorsal intermediate and medial cutaneous nerves, deep peroneal nerve, sural nerve, and/or saphenous nerves of the patient.

In aspects, the urological or gastrointestinal disorder is one or more of: overactive bladder (OAB) symptoms including bladder overactivity, urinary frequency, urinary urgency, urinary incontinence; interstitial cystitis (IC); urinary retention; pelvic pain; fecal incontinence; irritable bowel syndrome (IBS); and constipation. In some aspects the urological or gastrointestinal disorder is urinary incontinence.

In some aspects, the urinary incontinence is bedwetting and the device delivers pulses of a frequency of 5 Hz, 0.2 ms pulsewidth, and/or from greater than 0 mA to 100 mA, preferably from 2-6 times a toe twitch threshold of a patient.

In aspects of the method, the patient's foot is stimulated for from 1 to 360 minutes. In some aspects, the patient's foot is stimulated for at least 30 minutes. In some aspects, the patient's foot is stimulated for at least 180 minutes.

In aspects, the method further includes the step of administering an anti-muscarinic compound to the patient. In some aspects, the anti-muscarinic compound is one or more of atropine, benztropine, biperiden, ipratropium, oxitropium, tiotropium, glycopyrrolate, oxybutynin, tolterodine, chlorpheniramine, diphenhydramine, dimenhydrinate, orphenadrine, trihexyphenidyl, and dicyclomine. In some aspects, the anti-muscarinic compound is tolterodine.

In aspects of the method, the anti-muscarinic compound is administered at between 0.003 and 1 mg/kg and is administered orally or parenterally.

In aspects, the method further includes the step of administering to a patient in need thereof a serotonin reuptake inhibitor and/or a serotonin receptor antagonist. In some aspects, the serotonin reuptake inhibitor is one or more of alaproclate, citalopram, dapoxetine, escitalopram, femoxetine, fluoxetine, fluvoxamine, ifoxetine, indalpine, omiloxetine, panuramine, paroxetine, pirandamine, duloxetine, dapoxetine, sertraline, and zimelidine and the serotonin receptor antagonist is one or more of alprenolol, AV-965, BMY-7,378, cyanopindolol, dotarizine, flopropione, GR-46,611, isodocyanopindolol, isamoltane, lecozotan, methiothepin, methysergide, MPPF, NAN-190, oxprenolol, pindobind, pindolol, propranolol, risperidone, robalzotan, SB-649,915 (which acts as both a reuptake inhibitor and a receptor antagonist), SDZ-216,525, spiperone, spiramide, spiroxatrine, UH-301, WAY100135, WAY 100635, and xylamidine.

In some aspects of the method, the serotonin reuptake inhibitor is duloxetine. In some aspects, the serotonin receptor antagonist is WAY100635.

In aspects, the method further includes the step of administering both a serotonin reuptake inhibitor and a serotonin receptor antagonist. In some aspects, the serotonin reuptake inhibitor is duloxetine and the serotonin receptor antagonist is WAY100635 and duloxetine is administered at between 0.003 and 5 mg/kg and WAY100635 is administered at between 0.1 and 1 mg/kg. In some aspects, the serotonin reuptake inhibitor or the serotonin receptor antagonist are administered orally or parenterally.

In aspects, the method further includes the step of administering an opioid drug to the patient. In some aspects, the opioid drug is one or more of tramadol, morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine, buprenorphine, fentanyl, pethidine, levorphanol, methadone, dextropropoxyphene, tapentadol, endorphins, enkephalins, dynorphins, and endomorphins. In some aspects the opioid drug is tramadol.

In aspects of the method, the opioid drug is administered at between 0.003 and 1 mg/kg, and is administered orally or parenterally.

Also provided herein is a method of manufacturing an electrode-containing device. In aspects the method includes the steps of forming a base adapted to cover a portion of a bottom surface of a human foot including a portion of the forefoot overlaying a plurality of branches of the medial or lateral plantar nerves and a portion of the hindfoot overlaying the medial and lateral plantar nerves; attaching a first electrode to the base at a position in the base adapted to contact skin overlaying the medial and lateral plantar nerves; attaching a second electrode to the base at a position in the base adapted to contact skin overlaying a plurality of branches of the medial or lateral plantar nerves in the forefoot; and attaching electrode leads for the first and second electrodes to the base.

In some aspects the method includes the steps of forming a base adapted to cover a portion of a dorsal surface of a human foot including a portion of the forefoot overlaying a plurality of branches of the dorsal intermediate and medial cutaneous nerves, deep peroneal nerve, sural nerve, and/or saphenous nerve, and a portion of the hindfoot overlaying the superficial peroneal nerve, deep peroneal nerve, and/or saphenous nerve; attaching a first electrode to the base at a position in the base adapted to contact skin overlaying the superficial peroneal nerve, deep peroneal nerve, and/or saphenous nerve; attaching a second electrode to the base at a position in the base adapted to contact skin overlaying a plurality of branches of the dorsal intermediate and medial cutaneous nerves, deep peroneal nerve, sural nerve, and/or saphenous nerve in the forefoot; and attaching electrode leads for the first and second electrodes to the base.

In aspects, the first electrode is adapted to engage skin of the sole of the foot over at least 50% of the width of the forefoot. In some aspects, the first electrode is adapted to engage skin of the dorsal surface of the foot over at least 50% of the width of the forefoot.

In some aspects, the second electrode is adapted to engage skin of the sole of the foot over at least 50% of the width of the forefoot. In some aspects, the second electrode is adapted to engage skin of the dorsal surface of the foot over at least 50% of the width of the forefoot.

In aspects of the method, a plurality of the devices are manufactured to accommodate a plurality of standardized foot sizes.

In aspects, the electrodes are embedded within the base.

In aspects, the base is configured to have a perimeter having the shape of a sole of a foot, and optionally is an orthotic insert. In some aspects, the base is configured to have a perimeter having the shape of the dorsal area of a foot from the proximal phalanges to the talocrural joint. In some aspects, electrode leads are embedded within the base.

BRIEF DESCRIPTION OF THE DRAWINGS

FIG. 26 shows a table of results of daily voiding from diaries in subjects who responded to foot stimulation as described herein.

DETAILED DESCRIPTION

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the electrodes and base are described as overlaying an anatomical feature. This means that the described electrodes or base are positioned or configured/adapted for placement on skin superficial to (overlaying) a specific anatomical feature, such as an area of the foot, nerves and/or the bone(s) underlying the skin at that area of the foot. That is, the specified bone lies partially or wholly underneath the skin said to be overlaying the specified bone and/or nerve. Skin overlaying a specified bone can overlap the specified bone and another bone. To facilitate description of the position of an electrode in the foot, the "anterior-to-posterior axis" of the foot is an axis extending from the toes (anterior) to the heel (posterior) in an anterior to posterior direction. Likewise, "medial," "lateral," "dorsal," "plantar," "superficial," "proximal" and "distal" have their art-recognized meanings.

As used herein, the term "dorsal surface of the foot" refers to the top surface of the foot, including the ankle (talocrural) region and talocrural joint.

As used herein, the term "plantar surface of the foot" refers to the sole, or bottom surface of the foot.

As used herein, the term "ball of the foot" refers to the plantar surface of the foot, between the arch and the toes, around at least an anterior portion, e.g., the anterior 50%, of the metatarsals and the metatarsophalangeal joint.

Figure 1:
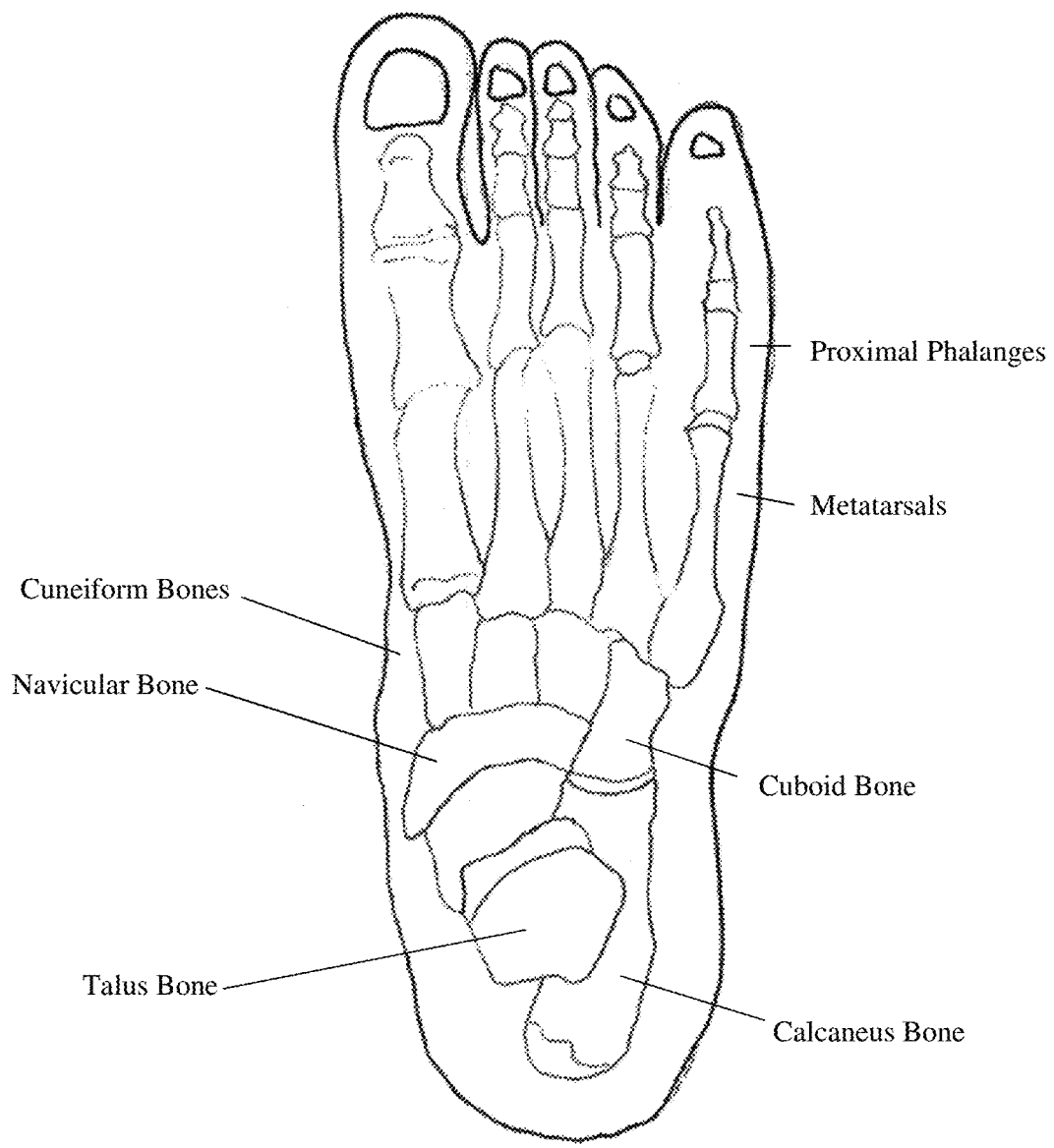
FIG. 1 is a schematic diagram of the dorsal (top) surface of a human foot, showing the bones of the human foot.
Figure 2:
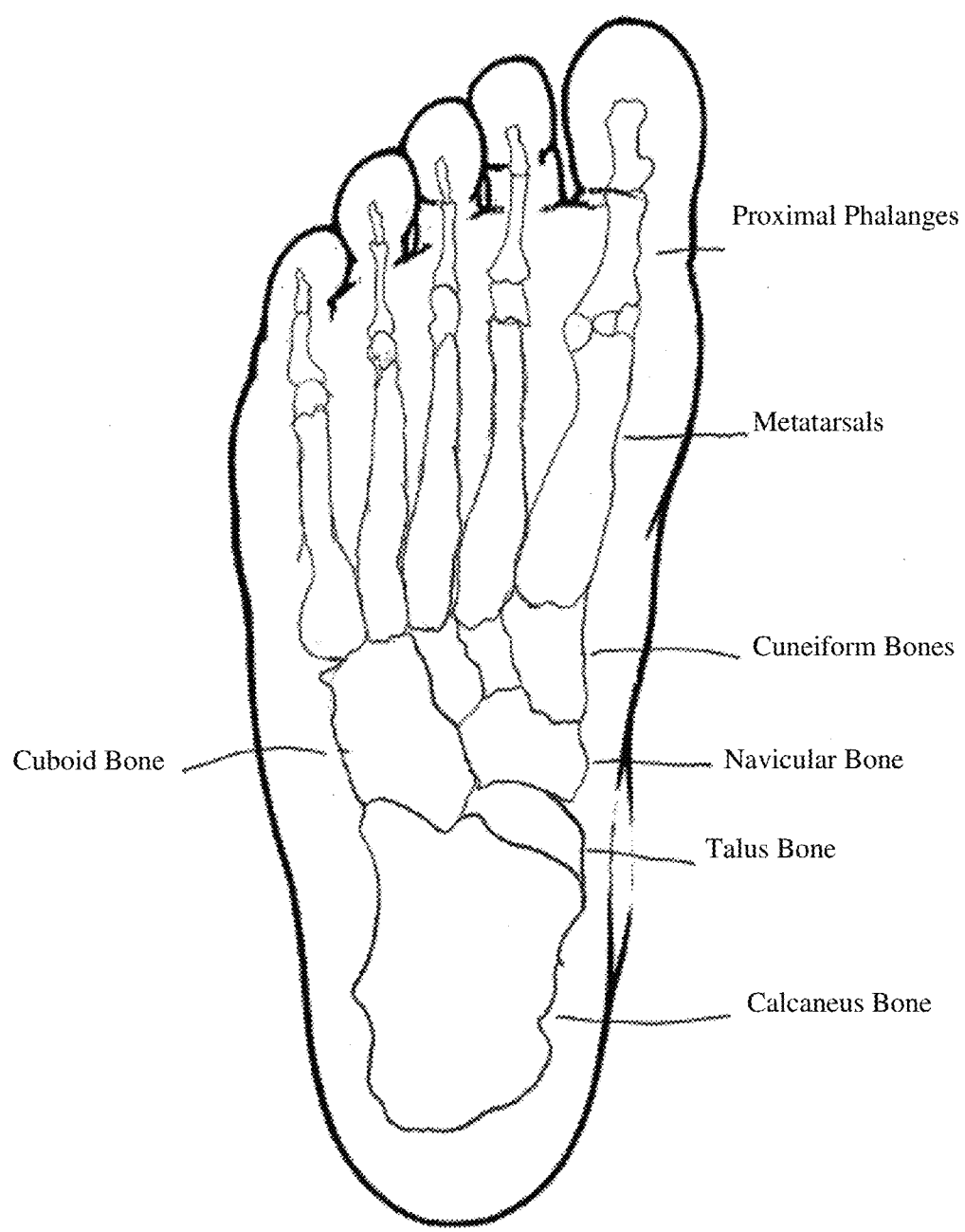
FIG. 2 is a schematic diagram of the plantar (bottom) surface of a human foot, showing the bones of the human foot.

As used herein, the term "forefoot" refers to the part of the foot (both dorsal and plantar surface) including and superficial to the metatarsals and proximal phalanges of the foot (FIGS. 1-2). This is the widest (medial to lateral) section of the foot. The medial longitudinal arch is the medial arch of the foot, and includes the calcaneus, talus, navicular, cuneiform and the first through third metatarsal. Its posterior portion includes the calcaneus and talus bones, and the medial and lateral plantar nerves enter the sole of the foot from the ankle at this point.

As used herein, the term "midfoot" refers to the part of the foot (both dorsal and plantar surface) including and superficial to the cuboid, navicular, and/or cuneiform bones (FIGS. 1-2).

As used herein, the term "hindfoot" refers to part of the foot (both dorsal and plantar surface) including and superficial to the talus and/or calcaneus bones, and/or the talocrural joint (FIGS. 1-2).

As used herein, the term "predominance" means more than 50%, for example when it is stated that an electrode of the electrode-containing device described herein overlays a predominance of the superficial peroneal nerve and branches thereof, for example of the dorsal intermediate and dorsal medial cutaneous nerves or the lateral and medial plantar nerves in the forefoot, the electrodes cover an amount of skin on the dorsal or plantar surface of the foot that overlays at least 50% of the superficial peroneal or lateral and medial plantar nerves and branches thereof (e.g., with regard to the peroneal nerve, the dorsal intermediate and dorsal medial cutaneous nerves), deep peroneal nerve, sural nerve, and saphenous nerve (FIGS. 3-4) at a given position in the anterior to posterior axis of the foot (e.g., on a frontal (coronal) plane) of the forefoot.

The ranges provided herein, for example and without limitation electric pulse frequencies, are based on experimentation on humans as well as cats. The frequencies necessary to elicit a desired response in humans and cats are very similar. As illustrated in U.S. Pat. No. 7,047,078, stimulation of the pudendal nerve in human subjects produce similar results as compared to the results in cats. As such, frequency ranges applicable to cats are considered to be effective in humans.

The devices, systems, and methods described herein provide a stimulus effective to inhibit bladder contractions and are expected to affect urological conditions including: overactive bladder (OAB) symptoms including bladder overactivity, urinary frequency, urinary urgency, urinary incontinence (including bedwetting), interstitial cystitis (IC), urinary retention, and pelvic pain. The devices, systems, and methods are also expected to affect gastrointestinal conditions, such as fecal incontinence, irritable bowel syndrome (IBS), and constipation. For example, sacral neuromodulation can treat both overactive bladder and urinary retention. In another example, transcutaneous stimulation of the tibial nerve approximately 10 cm above the ankle has shown some limited potential in alleviating urinary and fecal incontinence (see e.g., Queralto et al. Preliminary results of peripheral transcutaneous neuromodulation in the treatment of idiopathic fecal incontinence *Int J Colorectal Dis* (2006) 21: 670-672 and Vitton et al. Transcutaneous Posterior Tibial Nerve Stimulation for Fecal Incontinence in Inflammatory Bowel Disease Patients: A Therapeutic Option? *Inflamm Bowel Dis* 2009; 15: 402-405), though these methods are sub-optimal because they require precise placement of the electrode over the tibial nerve and are not believed to stimulate substantially, if at all, any nerves in addition to the tibial nerve. It is believed that sacral neuromodulation modulates the central nervous system (CNS) by stimulating the sacral root and sending neural activity into the CNS. This neuromodulation input can balance the CNS, that is, if the bladder is overactive, the sacral neuromodulation will cause the CNS to inhibit bladder activity, but if the bladder is retaining too much urine, then the sacral neuromodulation will make the CNS more excitatory to the bladder.

The foot stimulation methods described herein, using the devices and systems also described herein, are another type of neuromodulation that is less invasive and less troublesome to the user. The devices and systems send modulatory neural signal from the nerves of the foot to the CNS. The following examples show that neuromodulation caused by delivering stimulation to the foot through at least one cathodal and at least one anodal electrode can modulate the CNS to inhibit the bladder. This is not to say that foot neuromodulation can only induce inhibitory effects. When the pathological condition is the opposite (for example, urinary retention), foot neuromodulation at different intensities and durations, or the same, should be able to modulate the CNS to facilitate bladder contraction or facilitate voiding. In summary, foot stimulation is another type of neuromodulation that can induce either inhibitory or excitatory effect depending on the state of the CNS (that is, exciting or inhibiting an organ). As the following examples show, stimulation of nerves of the foot (somatic nerve) can modulate the bladder (autonomic organ). Therefore, it is logical and reasonable to conclude that such stimulation will also modulate other autonomic organs, for example in the gastrointestinal system.

It should also be recognized that the optimal electrical stimulation parameters to elicit a desired effect may vary to some degree from subject-to-subject, depending on a number of factors. Optimal frequencies to elicit the desired goals can be adjusted from person-to-person. A "patient" may be human or animal and unless specified otherwise embraces a specific patient, a class of patients or any human or animal in a generic sense and does not imply any doctor-patient relationship. Thus, a structure configured to, or adapted to, a patient's foot includes structures configured to a specific patient and/or a group of patients.

Subject to the limitations presented herein, any positioning of electrodes on the foot (at or below the ankle (talocrural) joint of a patient, on the dorsal (top) surface of a foot or the plantar (bottom)) that is useful in modulating urological, bladder, gastrointestinal, and/or rectal contractions/activity should be considered within the scope of the present devices, systems, and methods, and slight alterations of the specific positioning described below should also be considered to be within the scope of the described devices, systems, and methods.

Figure 3:
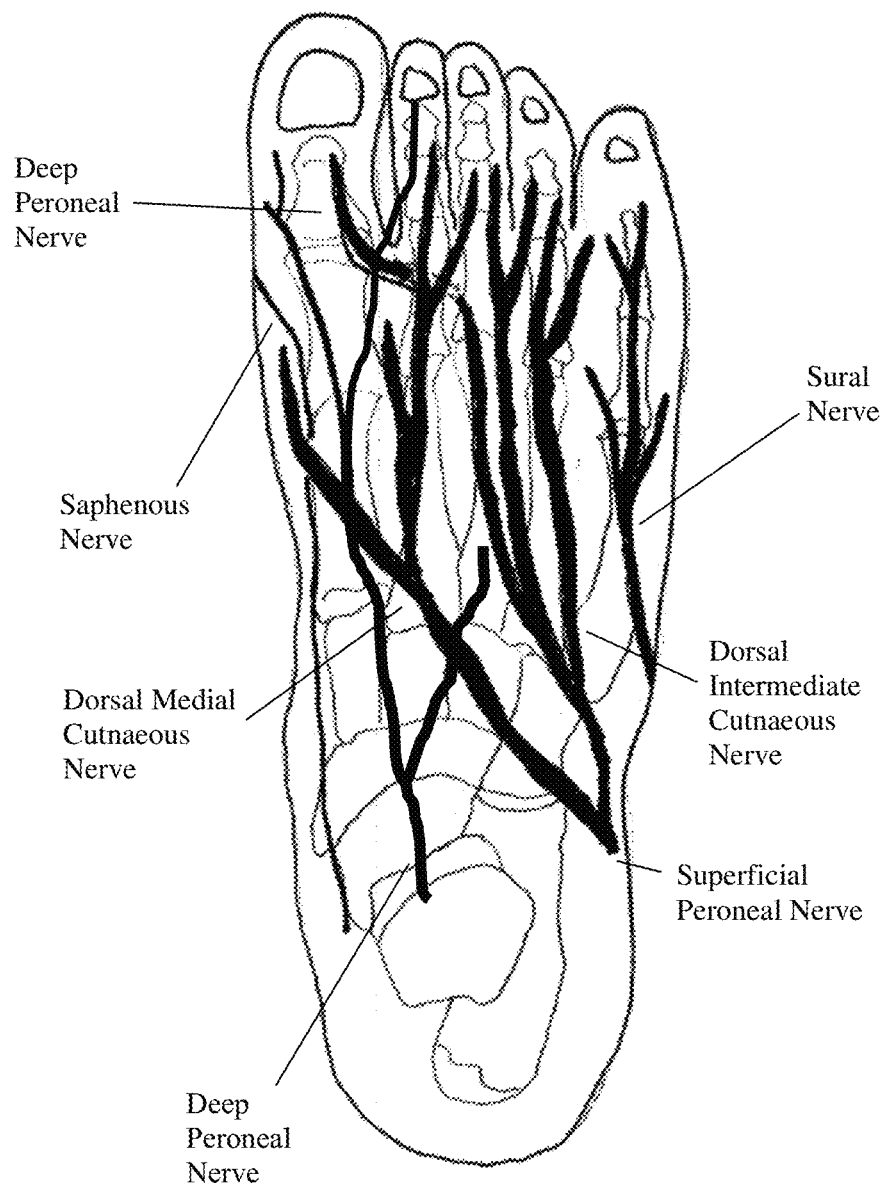
FIG. 3 is a schematic diagram of the dorsal (top) surface of a human foot, showing the bones of the human foot and the nerves, including the superficial peroneal nerve, dorsal intermediate cutaneous nerve, dorsal medial cutaneous nerve, deep peroneal nerve, sural nerve, and saphenous nerve.

Provided herein is an electrode-containing device for stimulating at least a portion of the superficial peroneal nerve and branches thereof (e.g. dorsal intermediate and dorsal medial cutaneous nerves), deep peroneal nerve, sural nerve, and/or saphenous nerve of a patient. The electrodes include a posterior (first) electrode and an anterior (second) electrode. The first electrode is positioned on the dorsal surface of the foot to stimulate the superficial peroneal nerve and branches thereof (e.g. dorsal intermediate and dorsal medial cutaneous nerves), deep peroneal nerve, and/or saphenous nerve at a portion of the foot overlaying at least a portion of the talus and/or calcaneus bones, as the superficial peroneal nerve, deep peroneal nerve, and/or saphenous nerve passes over the calcaneus and/or talus bones from the medial side of the foot/ankle to the dorsal surface of the foot. Thus, the first electrode is positioned on the dorsal surface of the foot and/or the talocrural joint to overlay at least a portion of the talocrural joint, at least a portion of the calcaneus bone and/or at least a portion of the talus bone (FIGS. 1 and 3). In some aspects the first electrode may be positioned on the lateral surface of the talocrural region/talocurural joint, to overlay the sural nerve. In other aspects the base is shaped such that the first electrode overlays the skin covering the superficial peroneal nerve, deep peroneal nerve, saphenous nerve, and/or sural nerve.

The second (anterior) electrode is sized and positioned to overlay approximately 50% or more of the branches of the superficial peroneal nerve and branches thereof (e.g. dorsal intermediate and dorsal medial cutaneous nerves), deep peroneal nerve, sural nerve, and/or saphenous nerve at the midfoot or forefoot, for example and without limitation spanning at least 50% of the width of the foot at its placement point on the anterior-posterior axis of the foot (FIGS. 1, 3). Thus, the second electrode overlays an anterior portion of the metatarsals, the metatarsophalangeal joint, and/or the proximal phalanges. In aspects, the second electrode of the device overlays, and provides stimulation to, at least 50% of the branches of the superficial peroneal nerve branches thereof (e.g. dorsal intermediate and dorsal medial cutaneous nerves), deep peroneal nerve, sural nerve, and/or saphenous nerve, for example and without limitation, 50%, more than 50%, more than 60%, more than 70%, more than 80% or more than 90% of the superficial peroneal nerve branches (e.g. dorsal intermediate and dorsal medial cutaneous nerves), deep peroneal nerve, sural nerve, and/or saphenous nerve at a given anterior-to-posterior position in the midfoot or forefoot, such as overlaying the metatarsophalangeal joint (FIG. 1). In aspects, the second electrode of the device overlays 50% or more of the superficial peroneal nerve and branches thereof (e.g. dorsal intermediate and dorsal medial cutaneous nerves), deep peroneal nerve, sural nerve, and/or saphenous nerve (FIG. 3). In one aspect, the device overlays, and thus may be used to stimulate, a nerve and branches of that nerve. For example, the device overlays the superficial peroneal nerve and branches thereof, the dorsal intermediate and/or dorsal medial cutaneous nerves and branches thereof, the saphenous nerve and/or branches thereof, the deep peroneal nerve and/or branches thereof, and the sural nerve and/or branches thereof.

The base is adapted to a portion of the dorsal surface of the foot, meaning it has a two- or three-dimensional shape that permits and optimally facilitates placement of the electrodes at specific positions on the dorsal surface of the foot as described herein. The base may have a perimeter shaped in any suitable manner to allow for electrode placement to stimulate the superficial peroneal nerve and branches thereof (e.g. dorsal intermediate and dorsal medial cutaneous nerves), deep peroneal nerve, sural nerve, and/or saphenous nerve as described herein, and to facilitate easy and reproducible placement of the device. The base may be shaped in any suitable manner to allow for electrode placement to stimulate the superficial peroneal nerve and branches thereof (e.g. dorsal intermediate and dorsal medial cutaneous nerves), deep peroneal nerve, sural nerve, and/or saphenous nerve as described herein, and to facilitate easy and reproducible placement of the device. One example of such an arrangement of electrodes is shown schematically in FIG. 5, panel A.

Figure 5:
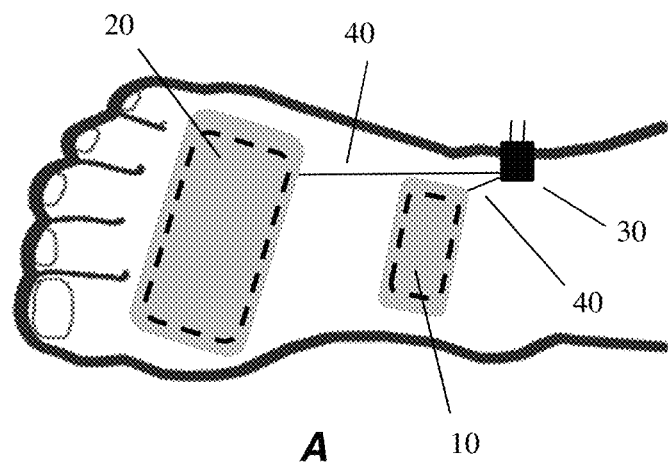
FIG. 5 is a schematic diagram of aspects of base shapes and electrode placement on the dorsal surface of a foot of a device described herein.
Figure 5:
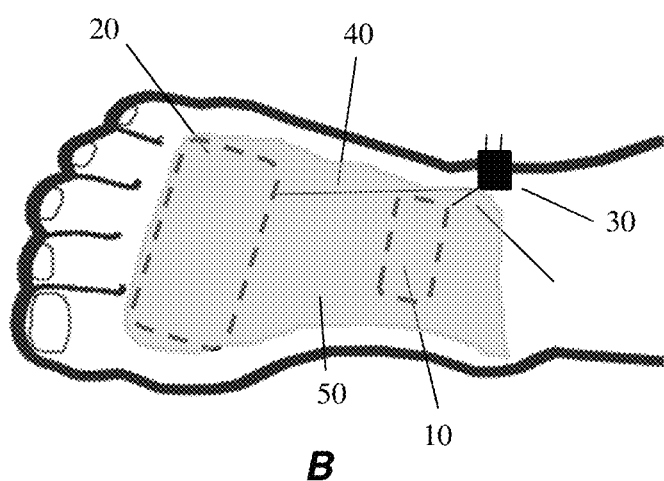
Figure 5:
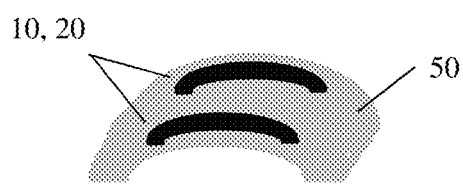

In aspects, the base is substantially shaped to overlay the dorsal surface of a human foot, or a portion thereof, for example from the talocrural joint to the proximal phalanges (FIG. 5, panel B). In other aspects, the base is substantially shaped to overlay the dorsal surface of a human foot, from just anterior to the talocrural joint to the metatarsophalangeal joint. Those of skill in the art will appreciate that the base can be of any size, and in one aspect is manufactured as an insert to match standard foot sizes so as to optimize placement of the electrodes and to facilitate proper placement of the device on the dorsal surface of the foot by a layperson (end-user). For example, the base may be sized to correspond to United States shoe sizes 1-15 and/or United Kingdom shoe sizes 0-14. The base may also be sized in width from A to G (and corresponding United Kingdom widths). The base may also be configured and/or contoured to account for any foot disorder that would benefit from a modified base, so that the electrodes in the device comfortably overlay the areas for which stimulation provides maximal effect in either stimulating or inhibiting bladder, gastrointestinal, and/or rectal contractions/activity.

In other aspects, the base may be any suitable size and configuration that allows for the electrodes to cover the requisite percentage or number of branches of the superficial peroneal nerve and branches thereof (e.g. dorsal intermediate and dorsal medial cutaneous nerves), deep peroneal nerve, sural nerve, and/or saphenous nerve. For example, the device may be substantially shaped as in FIG. 5, panels B and C, wherein the electrodes are contained within a two or three-dimensional structure that is configured to contour to the dorsal surface of the foot to allow for close interaction between the electrodes and the dorsal surface of the foot. In other aspects, the base can be of any shape or amount of material, for example an "I" shape, to allow for inclusion of electrodes of sufficient size while reducing the amount of base material needed. It should be noted that FIG. 5 is a schematic, illustrative figure, and should be treated as such. The possible range of coverage and shapes of the device is as described herein.

Figure 4:
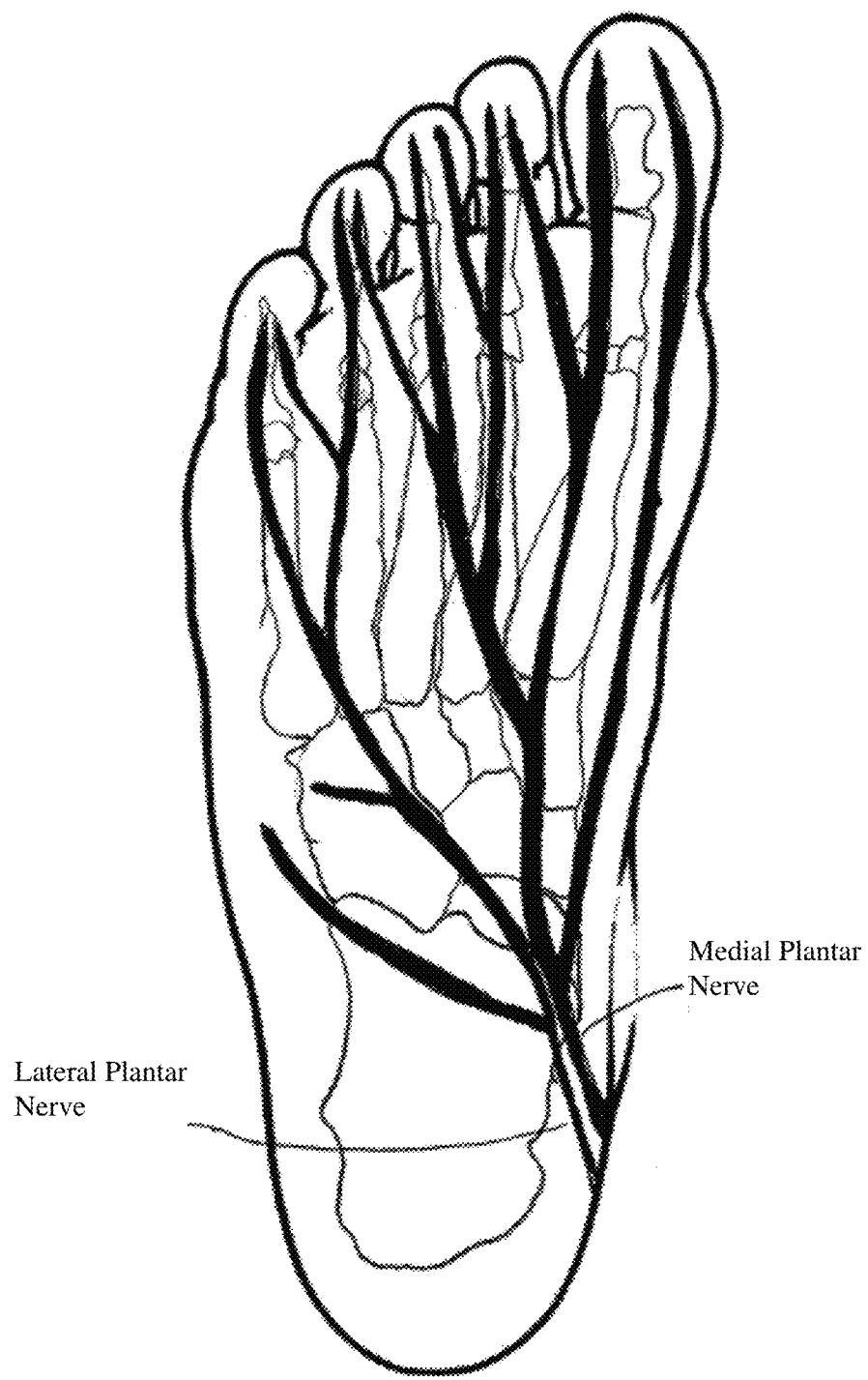
FIG. 4 is a schematic diagram of the plantar (bottom) surface of a human foot, showing the bones of the human foot and the nerves, including the lateral and medial plantar nerves.

Also provided herein is an electrode-containing device for stimulating at least a portion of the medial and lateral plantar nerves of a patient. The electrodes include a first (posterior) electrode positioned on the sole (plantar surface) of the foot to stimulate the medial and lateral plantar nerves at a posterior portion of the medial longitudinal arch of the foot as the nerves pass from the medial side of the foot/ankle to the sole of the foot. Thus, the first electrode is positioned on the sole of the foot to overlay a medial, anterior portion of the calcaneus bone and optionally a portion of the talus bone (FIGS. 2, 4). A second (anterior) electrode is sized and positioned to overlay a plurality of, e.g., 50% or more of, the branches of the medial and lateral plantar nerves at the midfoot or forefoot, for example and without limitation spanning at least 50% of the width of the sole of the foot at its placement point on skin of the sole of foot at the forefoot (FIGS. 1-4).

The second electrode in this aspect may overlay branches of either the medial or lateral planter nerve or branches of both. In aspects, the second electrode of the device overlays, and provides stimulation to, at least 50% of the branches of the medial and lateral plantar nerve branches, for example and without limitation, 50%, more than 50%, more than 60%, more than 70%, more than 80% or more than 90% of the medial and lateral plantar nerve branches at a given anterior-to-posterior position in the forefoot, such as overlaying the metatarsophalangeal joint, or ball of the foot (FIG. 2). In aspects, the second electrode of the device overlays 50% or more of the medial and lateral plantar nerve branches of the forefoot (FIG. 4). In one aspect, the device overlays, and thus may be used to stimulate, a nerve and branches of that nerve. For example, the device overlays the plantar nerve and branches of the plantar nerve, and/or the medial and/or lateral plantar nerves, and branches thereof.

Figure 6:
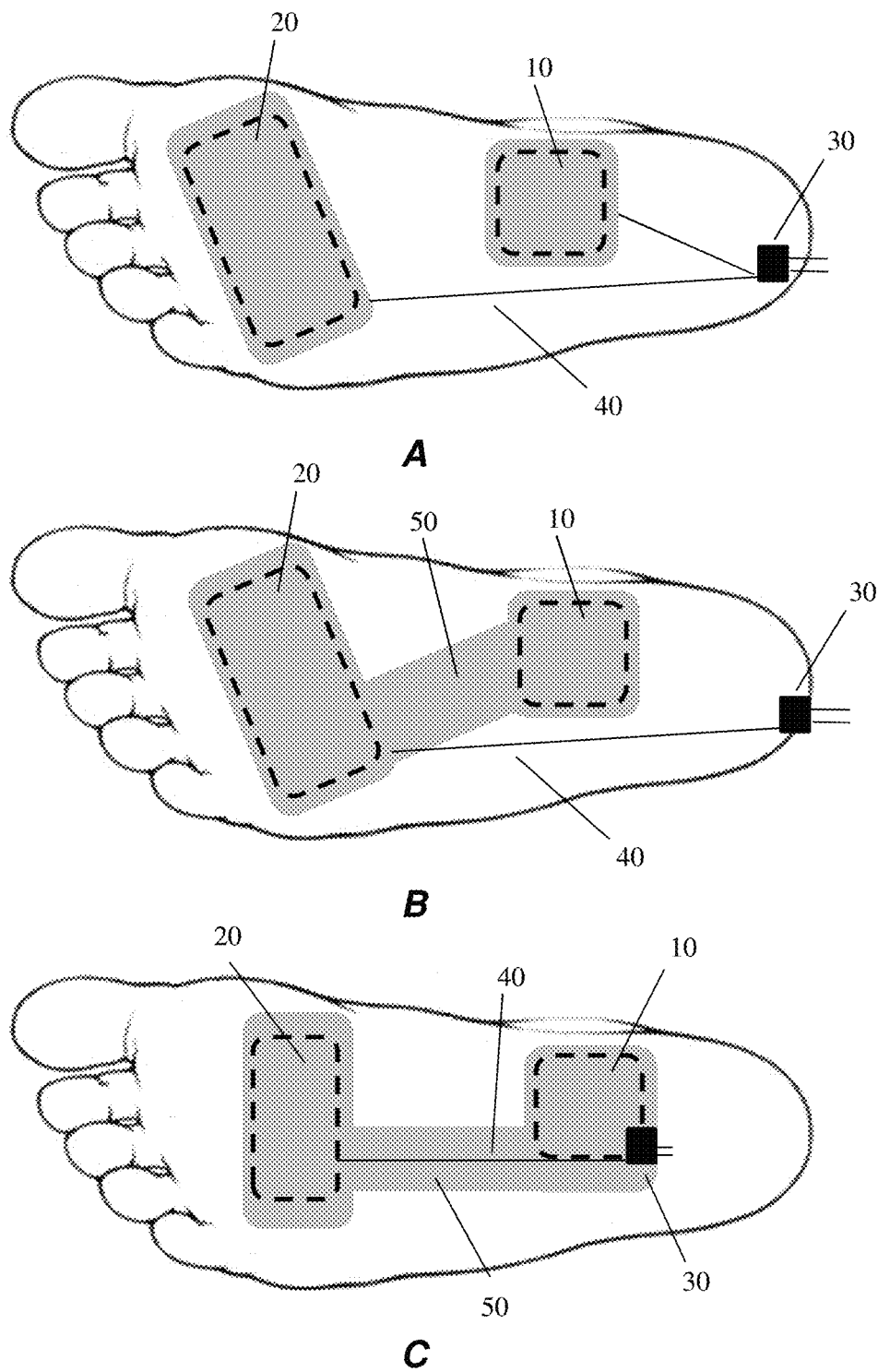
FIG. 6 is a schematic diagram of aspects of base shapes and electrode placement on the plantar surface of a foot of a device described herein.
Figure 7:
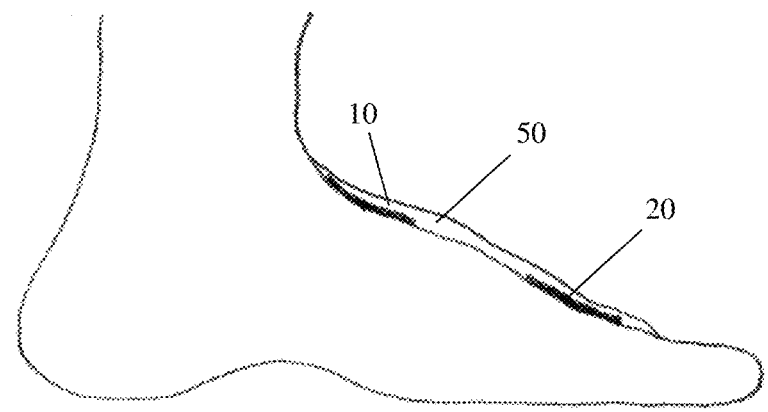
FIG. 7 is a schematic diagram of the side of a human foot and one aspect of a device for placement on the dorsal surface of a foot as described herein.
Figure 8:
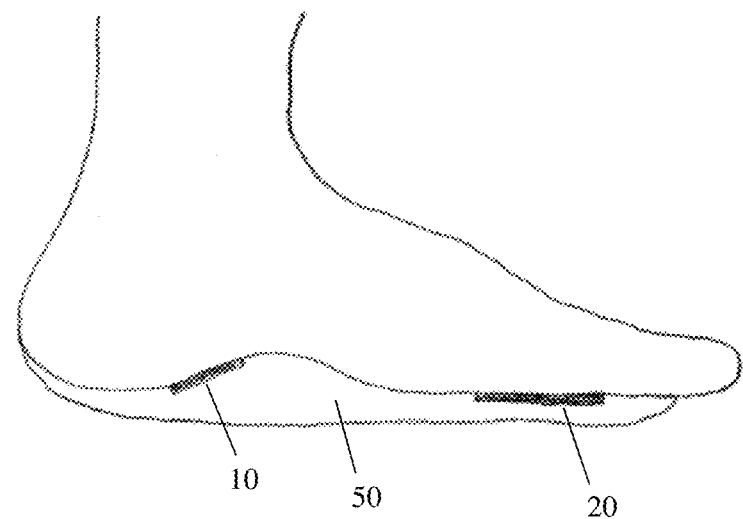
FIG. 8 is a schematic diagram of the side of a human foot and one aspect of a device for placement on the plantar surface of a foot as described herein.
Figure 8:
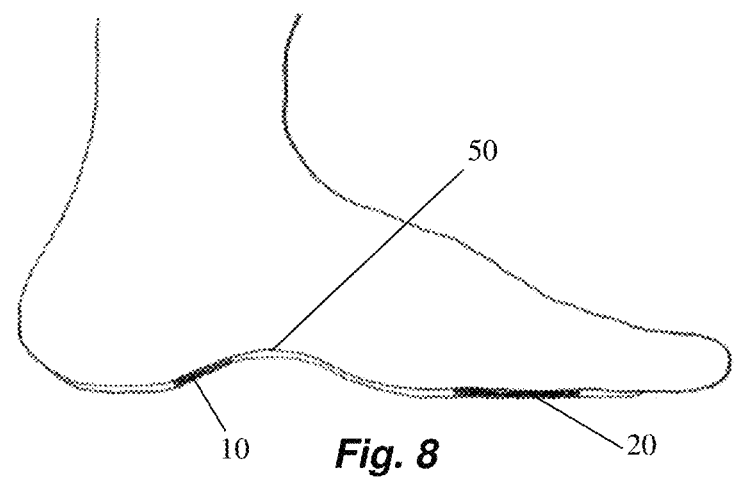

No matter whether the device described herein is designed to overlay the dorsal (FIGS. 5 and 7) or plantar (FIGS. 6 and 8) surface of the foot, the base may be formed of any material that provides comfort or minimizes discomfort, given that in aspects, the base is provided between the dorsal or plantar surface of an individual's foot and the individual's footwear and/or garments (socks, hose, and the like). In one aspect, the base is formed of a substantially or completely non-conductive material. Such materials include: gels, foams, rubbers, cellulose-based materials, cellophanes, silicon-based products, polymers, neoprene, animal hides, leathers, polyethylene, ethyl vinyl acetate, polypropylene, polyimide, polyester, polyethylene terephthalate, polyaryletheretherketone, polytetrafluoroethylene, polyethylene naphthalate, co-polymer plastics, and combinations thereof, which are known to those of skill in the art. The base may optionally include materials for added comfort, such as gels and the like, which are also known to those of skill in the art. In aspects, the base may be formed of mixtures of suitable materials, either in an amalgamation in a one-piece construction or in discrete layers of one or more materials. In one aspect, the base is an orthotic, custom-designed for the individual in need of the electrode-containing device (FIG. 8). In another aspect, the base has a thin profile, such as a thin film, membrane, or polymer, suitable for placement between the dorsal or plantar surface of an individual's foot and the individual's footwear or garment, such a sock, legging, hose, or the like (FIGS. 7 and 8).

The base of the device includes at least two positions for placement of electrodes to provide the stimulation capable of modulating urological, bladder, gastrointestinal, and/or rectal activity (FIGS. 5-13). With regard to the FIGS. 5-8, at least one electrode position, for the first electrode (10), is at a posterior portion of the base (50) of the device and at least one electrode position, for the second electrode (20), is at an anterior portion of the base. At least one of the electrode positions is for a cathodal electrode, or an electrode that acts as a cathode, and at least one of the electrode positions is for an anodal electrode, or an electrode that acts as an anode. According to one aspect, the second (anterior) electrode position, and electrode (20) that occupies said position, is of sufficient size such that it extends over a predominance, or more than 50%, of the width of the forefoot. In aspects, the base (50) also includes a connector (30), e.g., male or female plugs or other electrical connectors as are known in the art, for providing direct electrical connection between the electrode-containing device and a pulse generator. The electrodes (10, 20) are connected to a connector (30) via conductive leads (e.g., wires, traces, etc.) (40). Electrodes (10, 20) may each have a distinct lead connecting them to the connector (30), or may be connected in series (i.e., only one lead emerges from connector (30) to the electrodes).

In aspects, the electrodes (10, 20) are directly electrically connected to a pulse generator, but a connector (30) at some point between the pulse generator and the electrodes is preferred so that the electrode assembly can be replaced or exchanged. The connector (30) may be any low-profile electric connector, male or female, suitable for use in a low-profile foot orthotic, thin film, or the like so as to prevent discomfort to the patient when shoes are worn over the device. Non-limiting examples of such a low-profile connector may be see in U.S. Pat. No. 5,326,272. Low-profile electrical connectors are known to those of skill in the art. It may be preferable that leads (40) extend from the base of the device so that the connector (30) can be located in various locations for comfort. The pulse generator may be connected to the device through one or more wires, carrying a plurality of leads (i.e. at least one lead for the anode and at least one lead for the cathode).

The electrodes (10, 20) of the electrode-containing device reside on a surface of the base (50) that comes into contact with the dorsal (top—FIG. 5) or plantar surface (bottom—FIG. 6) of the foot during normal use. The electrodes are formed of a conductive material, suitable for conducting electrical stimulation from the electrode-containing device through the skin of the individual to the nerves underlying the skin of the foot. Suitable materials for forming the electrodes of the base include metals and metal foils, such as, for example and without limitation, copper, gold, silver, tin, nickel, steel, cupronickel, nickel-cobalt ferrous alloys, and carbon-based materials. Those of skill in the art are aware of the typical constitution of electrodes suitable for use with TENS (Transcutaneous Electrical Nerve Stimulation), NMES (Neuromuscular Electrical Stimulation), patterned Electrical Neuromuscular Stimulation (PENS), and Interferential Current (IFC). So long as the electrode is capable of delivering a suitable electrical current to the skin of a patient when placed atop or underneath a patient's foot at a position described herein, it is considered to be useful in the devices, systems, and methods described herein.

In aspects, the electrodes are replaceable electrodes. The electrodes may be held in place in the base by any suitable mechanism, such as for example and without limitation, by one or more snaps, snap connections, hook and loop connections, Velcro®, disposable and/or reusable adhesives that allow for removable adhesion of the device to a patient's foot, and the like. By way of non-limiting example, areas of adhesive placement for the device described herein may be seen between the hashed lines and the outline of the base in FIGS. 5 and 6. The adhesive may be conductive or non-conductive. In aspects, the adhesive is non-conductive. The use of a non-conductive adhesive such as described herein for removably adhering the base to a patient's foot maintains a discrete area of stimulation. By removably adhering it is meant that the adhesive is sufficient to maintain the base in a position for stimulation to the indicated areas during walking and movement of the individual, but is not so strong so as to cause injury and/or substantial pain during removal of the base from the foot, or to damage clothing/garments during removal.

Figure 13:
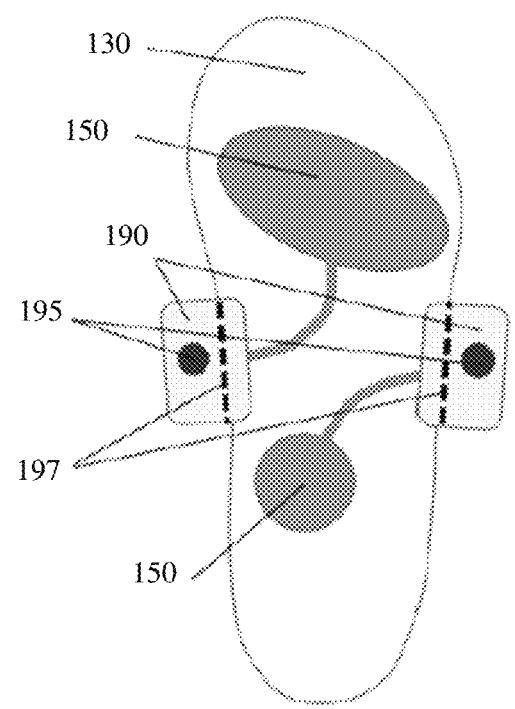
FIG. 13 is a schematic diagram of the (a) bottom and (b) side of a human foot and placement on the plantar surface of the foot of one aspect of a device as described herein.
Figure 13:
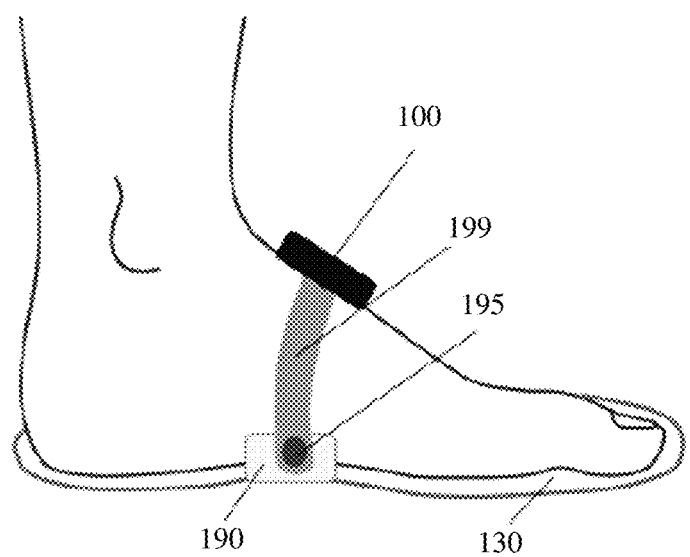

Those of skill in the art will appreciate and have knowledge of suitable means for holding the electrode in place in the base material, and will understand that the amount of adhesive and type of adhesive that is suitable for holding the device in place, on the foot of the patient or in the footwear of the patient, can be adjusted. Non-limiting examples of medically-acceptable adhesives include: adhesives used on bandages, medical tapes (such as those manufactured by 3M, St. Paul, MN, USA), including those formed of silicone or cloth, Soft-Pro™ Silicone Gel, Acrylics, and PU Gel manufactured by Scapa Healthcare (Liverpool, New York, USA and Inglewood, CA, USA), Uro-Bond® III Adhesive, manufactured by Urocare (Pomona, CA, USA), and the like known to those of skill in the art). In other aspects, the device may comprise and be held in place by elastic bands, or bands that may connect through snap connections, hook and loop connections, Velcro®, and the like. The bands can encircle the dorsal or plantar portion of the foot and connect there by any suitable means. For example, and without limitation, FIG. 13 shows one aspect of a device that is configured for placement on the plantar surface of a patient's foot. In other aspects, the device includes material that fits between toes/phalanges of the wearer's foot for supporting the device in place (in addition to any support provided by footwear or garments).

In aspects, the electrodes include a conductive gel or paste for increasing conductance and/or reducing impedance/resistance between the electrode and the foot of the patient. For example, and without limitation, conductive gels/pastes may be provided within the hashed line portion shown in FIGS. 5 and 6. Suitable conductive gels are known to those of skill in the art. For example and without limitation, a suitable conductive gel is Spectra 360 Electrode Gel manufactured by Parker Labs (New Jersey, USA) or Ten20 EEG Conductive Paste manufactured by Weaver and Company (Colorado, USA). In aspects in which the electrodes are replaceable, the electrodes may be pre-packaged with an amount of conductive gel or paste. According to one aspect, the conductive gel has adhesive properties, for example Ten20 EEG Conductive Paste (Weaver and Company, Colorado, USA), Tensive Conductive Adhesive Gel (Parker Labs, New Jersey, USA), and the like, which are known to those of skill in the art. In aspects, the conductive gel or paste surrounds an electrode center and is encapsulated by a conductive material, such that gel/paste is able to improve conductivity/decrease impedance/resistance without causing spillage of the conductive gel/paste onto the patient's foot or garments. In aspects in which the electrodes do not come pre-packaged with gel, the patient may apply such gel/paste each day before the electrode-containing device is applied to the foot.

The electrodes of the electrode-containing device are spaced-apart and oriented by configuration of the electrodes on the base. The electrodes are attached to the base, meaning they are affixed to a surface of, or partially or completely embedded within the base, leaving a functional surface of the electrode exposed for skin contact. The size and positioning of the electrodes in the base is based on the relative location of anatomical features of the dorsal or plantar surface of the foot, and depends on the size of an individual's foot, and, optionally, based on the specific contours of an individual's foot or a foot of a typical individual. In certain aspects, the configuration of the electrodes within the device provides electrical stimulation to at least a portion of the forefoot and/or midfoot and at least a portion of the hindfoot and/or talocrural region/talocrural joint. Exemplary arrangements of electrodes on an electrode-containing devices are shown in FIGS. 5-13. In aspects, the electrodes overlay at least a portion of the metatarsophalangeal joint and at least a portion of the calcaneus and/or talus bones. Any arrangement of electrodes in which stimulation can be provided to the nerves of the foot, particularly to a predominance of the superficial peroneal nerve and branches thereof (e.g. dorsal intermediate and dorsal medial cutaneous nerves), deep peroneal nerve, sural nerve, saphenous nerve, and/or the lateral and/or medial plantar nerves is contemplated by the present invention. As provided above, at least one of the electrodes acts as a cathode and at least one of the electrodes acts as an anode. That is, the flow of electrons from the electrode-containing device of the present invention is from anode, through the tissue of the foot, to the cathode.

In aspects, the at least one cathode is the anterior electrode and overlays at least a portion of the forefoot and/or midfoot, and the at least one anode is the posterior electrode and overlays at least a portion of the hindfoot and/or talocrural joint. In other aspects, the cathode overlays at least a portion of the metatarsophalangeal joint and the anode overlays at least a portion of the talus and/or calcaneus bones. The opposite configuration may also be suitable for providing electrical stimulation in accordance with the present invention. That is, the anode may be the anterior electrode and may overlay at least a portion of the forefoot and/or the metatarsophalangeal joint and the cathode may be the posterior electrode and overlay at least a portion of the talus and/or calcaneus bones.

Without wishing to be bound by this theory, the device, system and method described herein stimulate the superficial peroneal nerve and branches thereof (e.g. dorsal intermediate and dorsal of the tibial nerves, namely the medial cutaneous nerves), deep peroneal nerve, sural nerve, and/or saphenous nerves. In aspects, the device, system and method described herein stimulate the medial and/or lateral plantar branches of the tibial nerve.

The electrodes of the electrode-containing device described herein provide electrical pulses effective to modulate urological, bladder, gastrointestinal, and/or rectal activity. In one aspect, the stimulation provided by the device inhibits bladder contractions. This is thought to produce a storage stage, similar to the typical storage stage of the normal micturition or defecation processes. As will be recognized by a person of skill in the art, characteristics of electrical pulse, including, without limitation, amplitude (pulse strength, referring to the magnitude or size of a signal voltage or current), voltage, amperage, duration, frequency, polarity, phase, relative timing and symmetry of positive and negative pulses in biphasic stimulation, and/or wave shape (e.g., square, sine, triangle, sawtooth, or variations or combinations thereof) may be varied in order to optimize results in any particular subject or class of subjects. Subjects may be classified by species, disease/condition, sex, or any other factor that can be generalized to a group. Stated ranges are intended to include all values and ranges within the stated ranges. So long as other characteristics of the electrical signals (e.g., without limitation, amplitude, voltage, amperage, duration, polarity, phase, relative timing and symmetry of positive and negative pulses in biphasic stimulation, and/or wave shape) are within useful ranges, modulation of the pulse frequency will achieve a desired result. Useful values for those other characteristics are well-known in the art and/or can be readily established by routine experimentation.

One characteristic of the electrical signals used to produce a desired response, as described above, is pulse frequency. Although effective ranges (e.g., frequencies able to produce a stated effect) may vary from subject-to-subject, and the controlling factor is achieving a desired outcome, certain, non-limiting exemplary ranges may be as follows. For inhibiting bladder or bowel contractions, those frequencies may range from approximately 1 Hz (Hertz, or pulses per second) to approximately 500 Hz, though in practice, the range may be more typically 1-50 Hz, the range typically used for human nerve stimulation. Data below shows a range of at least from 5-20 Hz, with 5 Hz pulses being preferred in some instances. Useful pulse durations (pulse widths) typically range from 0.01 to 3.0 ms (milliseconds), for example 0.2-1.0 ms or 1 ms pulses.

Another characteristic of the pulses are the voltage. Nerve stimulation can be achieved in a typical range of from 1-100 V, for example 3-16 V as shown in the examples below, with a range of from 1 to 20 V being preferred in many instances. The typical voltage for foot stimulation may be from 2 to 6 times the toe twitch motility threshold (2 T-6 T), where the pulses cause toe twitching.

Yet another characteristic of the pulses is the current that is applied to produce the stimulation that is capable of modulating urological, bladder, gastrointestinal, and/or rectal activity. Stimulation can be achieved in a typical range of from 1 milliamperes (mA) to 80 mA. As shown in the examples below, a range of 15 mA to 60 mA, or 25 mA to 60 mA is preferred in many instances for providing the range of 2 T to 6 T desired in one aspect.

As indicated above, the waveform of the pulses may vary, so long as the desired effect is realized. One skilled in the art will appreciate that other types of electrical stimulation may also be used in accordance with device, system and methods described herein. Monophasic or biphasic stimuli, or a mixture thereof may be used. Damage to nerves by the application of an electrical current may be minimized, as is known in the art, by application of biphasic pulses or biphasic waveforms to the nerve(s), as opposed to a monophasic pulses or waveforms that can damage nerves in some instances of long-term use. "Biphasic current," "biphasic pulses" or "biphasic waveforms" refer to two or more pulses that are of opposite polarity that typically are of equal or substantially equal net charge (hence, biphasic and charge balanced) and may be symmetrical asymmetrical or substantially symmetrical. This is accomplished, for example, by applying through an electrode one or more positive pulses, followed by one or more negative pulses, typically of the same amplitude and duration as the positive pulses, or vice versa, such that the net charge applied to the target of the electrode is zero or approximately zero. The opposite polarity pulses may have different amplitudes, profiles or durations, so long as the net applied charge by the biphasic pulse pair (the combination of the positive and negative pulses) is approximately zero.

The waveform may be of any useful shape, including without limitation: sine, square, rectangular, triangle sawtooth, rectilinear, pulse, exponential, truncated exponential, damped sinusoidal. The pulses may increase or decrease over the stimulus period. In aspects, the waveform is rectangular. The pulses may be applied continuously or intermittently as needed. As indicated below, stimulation of the foot at certain voltages for certain time periods elicits post-stimulus inhibition of bladder contractions. Therefore, the stimulus may be applied for short intervals (e.g. 1-10 minutes) or longer intervals (up to 360 minutes) to achieve longer-lasting relief, in terms of hours or days. In certain aspects, the stimulus is applied for at least 15, 30, 45, 60, 75, 90, or more minutes. The stimulus may be applied intermittently (that is, the pulses are turned on and off alternately during a stimulus interval for any time period) during continuous or interval stimulus protocols. For example, the stimulus may be applied for 5 seconds on and 5 seconds off over an interval of, for example, 1-10 minutes or longer. Other examples of intermittent application of pulses may be 1-90 seconds on and 1-90 seconds off over up to a 360 minute time period. So long as other pulse parameters are within acceptable limits, the inhibition is temporary and does not damage the involved nerves. For example, intermittent application of pulses may be continuous, that is, for as long as the pulses are having the desired effect, and for as long as the patient desires (i.e., is not painful or harmful to the patient). A benefit of stimulating the dorsal surface of the foot, compared to stimulation of the plantar surface of the foot, is that continuous stimulation is not needed when the dorsal surface of the foot is stimulated. This increases comfort and patient compliance. However, in one aspect, the stimulation is provided continuously, for example to treat severe symptoms, or any symptom that does not respond to intermittent, short-term stimulation to the degree desired by a clinician or the patient. Additionally, the full weight of the patient's body does not bear on the electrodes, which can reduce discomfort compared to placement of electrodes on the plantar surface.

In another aspect, a system for use in inhibiting in a patient one or more of: bladder contractions, rectum contractions, urination (including bedwetting), defecation, and pelvic pain of the bladder, urethra, prostate, anus or rectum is provided. The system comprises the electrode-containing device essentially as described above and a pulse generator unit, in communication with the device, configured to produce electric pulses able to modulate urological, bladder, gastrointestinal, and/or rectal activity, such as inhibition of bladder contractions. As indicated above, the frequency ranges from 1 Hz to 500 Hz, such as 1-50 Hz, 5-20 Hz, or 5 Hz. Voltage may range from 1-100 V, such as from 1-20 V or from 3-16 V. Current may range from 1 mA to 80 mA. The aforementioned parameters may be adjusted to provide a stimulus that is from 2 to 6 T, and may be activated for from 1 minute to 360 minutes. The system may be set to produce pulses continuously or intermittently as described above, and can be controllable by the patient, healthcare provider, or both. As described previously, because the electrodes are placed on the dorsal surface of the foot, continuous stimulation of the superficial peroneal nerve is not required (though it may be employed) to achieve the desired effect of modulating urological/gastrointestinal activity.

In practice, the pulse generator may be programmable, pre-programmed, non-programmable, or otherwise adapted to or configured to produce pulses within the ranges described herein as being useful for the stated purposes of modulating urological, bladder, gastrointestinal, and/or rectal activity. For example, a commercial multi-purpose electrical stimulator for use in, e.g., TENS or NEMS, may be adjusted to the parameters useful in the methods described herein. In one non-limiting example, the device is non-programmable, having a pre-fixed output for voltage, pulse frequency, pulse length, and/or stimulus pattern/interval that cannot be changed. For instance, in one aspect, the pulse generator produces 0.2 ms pulses at 5 Hz and between 25 and 60 mA for 90 minutes whenever the device is activated either by the patient or another, or at specific intervals, for example hourly, every 90 minutes, every 120 minutes, or longer. In aspects, the stimulation occurs for discrete periods 1 or more times per day, for example three times per day for 30 minutes each period. Other settings may be any useful stimulation parameters within the ranges described above as being useful in the methods described herein. In another example, the device has two or more pre-fixed settings that cannot be changed, so that a patient or health care provider can choose the most effective stimulation parameter for the patient or for the patient's particular circumstances (e.g., in a meeting versus before bed). The frequency may be adjustable or achieved in any manner within any range described herein. Programmable or fixed-output electrical pulse generators are common and configuration to the stimulation parameters described herein is well within the abilities of those of ordinary skill in the art. For example, and without limitation, U.S. Pat. Nos. 5,273,033; 3,881,494; and 3,902,502 describe suitable pulse generators.

The system further includes a controller for providing instructions to the pulse generator. The controller may be a wireless controller, for providing control instructions to the pulse generator. In such aspects, the pulse generator includes a first wireless communication system and the controller includes a second wireless communication system, an input, and an optional display. In one aspect, the electric pulses are monophasic. The first wireless communication system may also transmit status information for the pulse generator to the wireless controller. Further description of one aspect of such a system is described in reference to FIGS. 9-13. The phrases "configured to" and "adapted to" and like terms or phrases refer to the manufacture, production, modification, etc. of a device or system to produce a desired function. In the context of the devices or systems described herein, a device or system "adapted to" or "configured to" produce a desired output is a device programmed of otherwise manufactured, produced, or modified in any manner to produce the stated effect. In the context of an electrode assembly as described herein, the device may be "adapted to" and "configured to" a specified anatomical structure, such as the for instance the physical size and shape of the sole of the foot or a portion thereof, such as the profile of an arch, heel, ball of the foot, toes or foot pad. Additionally, when it is stated that the base is configured to interact with the dorsal or plantar surface of a human foot, it is meant that the base is shaped, sized, and contoured in a manner that allows for a close tactile relationship between the surface (including electrodes) of the base and the top (dorsal) or bottom (plantar) surface of the foot, to allow for good conduction of electrical pulses from electrodes to the nerves underlying the skin.

Figure 9:
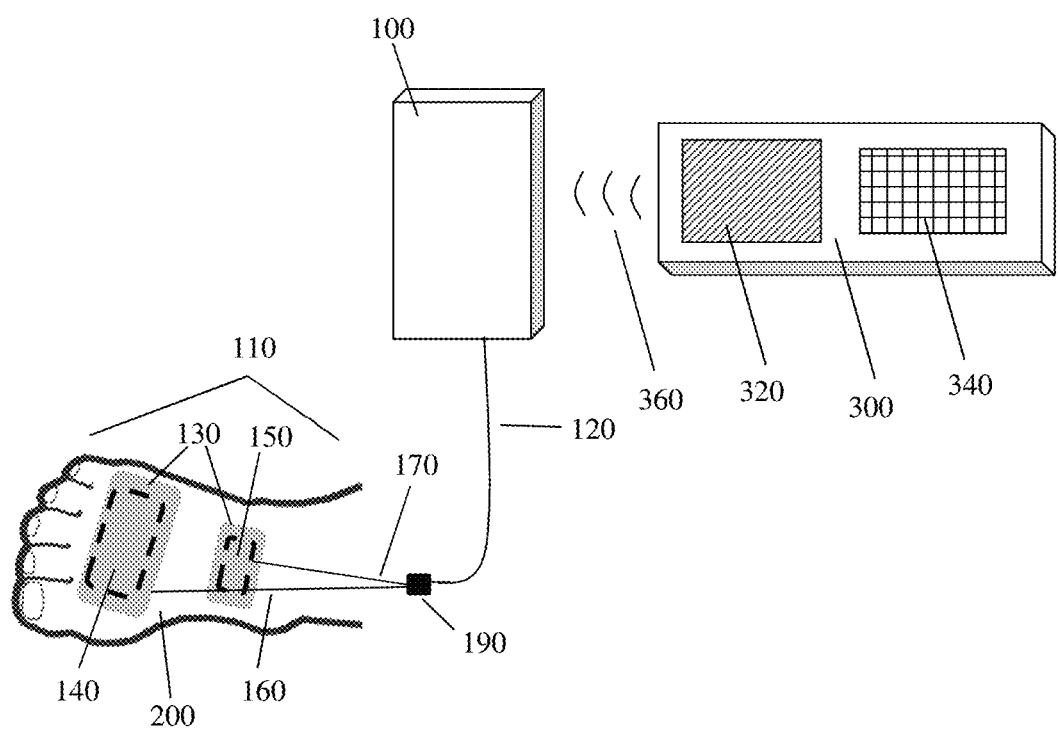
FIG. 9 is a schematic diagram of one aspect of a system including a device for placement on a dorsal surface of the foot as described herein.
Figure 10:
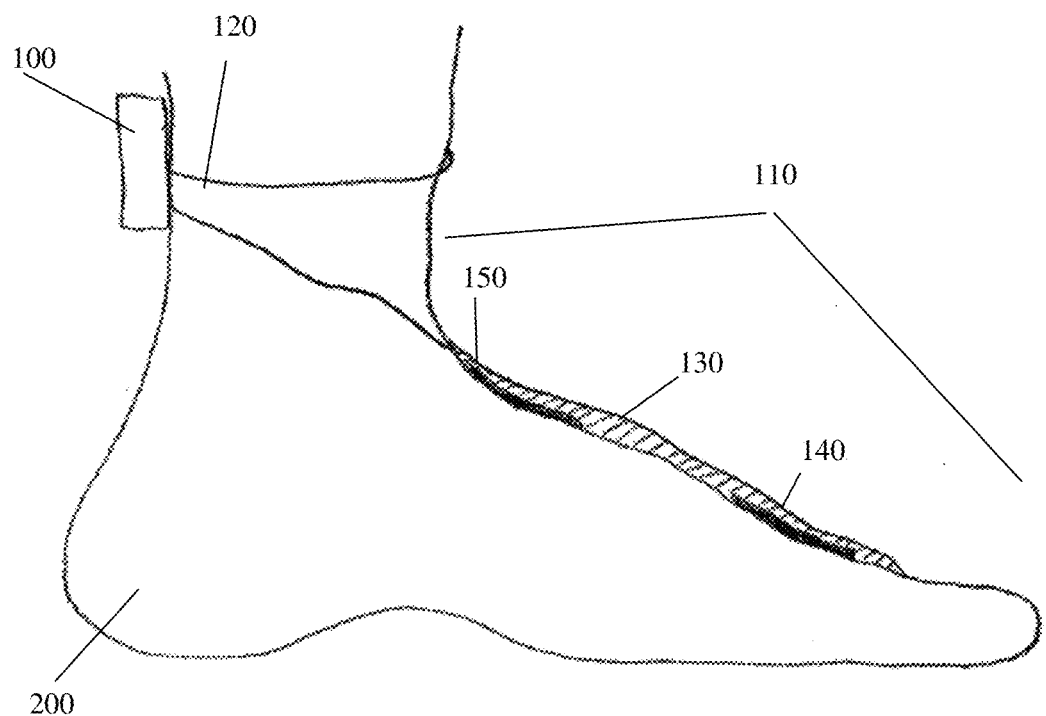
FIG. 10 is a schematic diagram of one aspect of a system including a device for placement on a dorsal surface of the foot as described herein.

Turning to FIGS. 9 and 10, depicted schematically are aspects of a system for stimulating foot nerves according to the device and methods described herein. Structures are out of proportion to facilitate illustration of elements of the depicted system. Pulse generator 100 is depicted as having one output channel, though an increased number of output channels falls within the scope and spirit of the invention. Wire 120 is attached by leads 160 and 170 to electrodes 140 and 150, which are integrated into the base 130 of the electrode-containing device 110 on the dorsal surface of the foot across the forefoot/midfoot (electrode 140) and hindfoot region (electrode 150) of a foot 200. In aspects, only a single, multi-conductor wire 120 connects pulse generator 100 to the leads 160, 170 of electrode-containing device 110 through connector 190, but the single wire contains at least a plurality of leads, for connecting to the anode and cathode. Another aspect (not shown), employs a plurality of wires, one carrying lead(s) for cathode(s) and others carrying lead(s) for anode(s) rather than single wire 120. In the aspect of FIG. 9, electrode 140 is shown on the dorsal surface of the foot at the midfoot and/or forefoot while electrode 150 is shown at the hindfoot.

Output parameters of the pulse generator 100 can be controlled via a wired interface, but also may be controlled by wireless transmission, as shown in the aspect of FIG. 9, which can be carried any suitable wireless protocol, such as radio frequency, IEEE 802.11a/ac/b/g/n, Bluetooth, ZigBee (IEEE 802.15), etc. Thus, an external controller 300 is depicted for communicating with the pulse generator 100. External controller 300 is depicted as having a display 320, such as an LCD, LED or OLED display, and a keypad 340 for entering data into the external controller 300. External controller is depicted as sending a wireless transmission 360 to pulse generator 100, though in another aspect, data can be transferred both to the pulse generator 100 from the external communicator 300 and vice-versa, to permit monitoring of one or more parameters of pulse generator 100, including, without limitation, output signal characteristics (e.g., frequency, amplitude, etc. as outlined above) and battery strength. Smartphones, tablets or computers may be used as controllers, software, such as iOS, Android or Windows-based "apps" may be developed to act as controllers for these devices.

Likewise, wireless transmission 360 can be replaced by a wire or other conductor. Activity of pulse generator 100 and external controller 300 typically is microprocessor controlled and software/firmware installed onto the pulse generator 100 and external controller 300 hardware may be used to implement the described tasks, and to provide, for example and without limitation, a graphical user interface (GUI) for the display 320, which facilitates use of the system. Both pulse generator 100 and external controller 300 may comprise any suitable electrical and electronic components to implement the pulse, communication, feedback, adjustment, etc. activities, including, microprocessors, memory (e.g., RAM, ROM. Flash memory, etc.), connectors, batteries, power transformers, amplifiers, software (including, for example and without limitation: firmware, operating systems, utilities, processes, routines), etc. A person of skill in the electronic arts will be able to implement such a system using readily-available electronics parts and ordinary programming skills. Proprietary chips, chipsets, etc. may be designed and manufactures to implement the devices described herein. Elements of the system depicted in FIG. 9, such as a battery and a pulse generator can be integrated into an aesthetically-pleasing housing, such as an anklet, such as is schematically illustrated in FIG. 10.

With continuing reference to FIG. 9, pulse generator 100 may be connected (at 190) to electrode-containing device 110 through any suitable connection that can transmit pulses provided by pulse generator 100 to the device 110 abutting the dorsal surface of an individual's foot 200. Pulse generator 100 and electrode-containing device 110 may be permanently connected through wiring, or through a releasable coupling. Pulse generator 100 may be a device that can be attached to the individual wearer's ankle, shoe, or any other suitable place for the pulse generator 100 to provide the pulses necessary to stimulate the nerves of the foot through electrode-containing device 110.

The external controller 300 may be a proprietary device that is specifically designed for the task, or a non-proprietary device, such as a commercial TENS controller, smart phone, tablet, personal computer or a portable computer. Pulse generator 100 may comprise any number of channels, so long as the number of channels needed to implement a desired method is provided.

With continuing reference to the system of the present invention, FIG. 10 shows a side view of one aspect of the system, including electrode-containing device 110, base 130, electrodes 140, 150, and pulse generator 100. A controller (not shown) may provide instructions to pulse generator to provide sufficient stimulation through wire 120 containing leads for anode and cathode to stimulate nerves of the foot 200. Pulse generator 100 may be a device that is suitable for attachment around the ankle or lower leg of a patient, such that it can be disguised/hidden from view while still providing stimulation to the patient's foot 200. Wire 120 containing leads may be placed between the wearer's leg/ankle and a garment (sock, hose, or the like) for a thin film-type electrode-containing device (not shown) or for a flexible or rigid two or three-dimensional structure, or may overlay a garment (sock, hose, or the like) for a flexible or rigid two or three-dimensional structure 110.

Returning to FIG. 9, a potential difficulty with use of wireless devices such as a wireless controller for communicating instructions to a pulse generator capable of receiving wireless instructions is one of identity. A controller 300 should only be able to control one pulse generator 100 to prevent accidental stimulation of unintended subjects, or even intentional stimulation. In its simplest form, the transmission range of the devices can also be limited to prevent transmission over distances more than a few feet, thereby limiting the chances of unintended stimulation (crosstalk). Also, any number of identity verification mechanisms may be utilized to prevent crosstalk. In one aspect, different transmission wavelengths may be used for different devices, thus lowering the likelihood of crosstalk. In another aspect, the pulse generator 100 is programmed to only respond to a transmission containing a pre-defined signal, such that the pulse generator 100 and external wireless controller 300 must first, and/or periodically "handshake" in order to communicate. Likewise, the pulse generator 100 and/or controller 300 may transmit encrypted signals which only can be decrypted by a key stored in the other of the pulse generator 100 and/or controller 300. In another aspect, RFID tagging technology may be used to ensure that the controller 300 and pulse generator 100 match. Any combination of these proximity and/or identity verification measures may be used to prevent cross-talk. Other useful technologies for ensuring security and identity in communication are, or may be available and are equally applicable.

Figure 11:
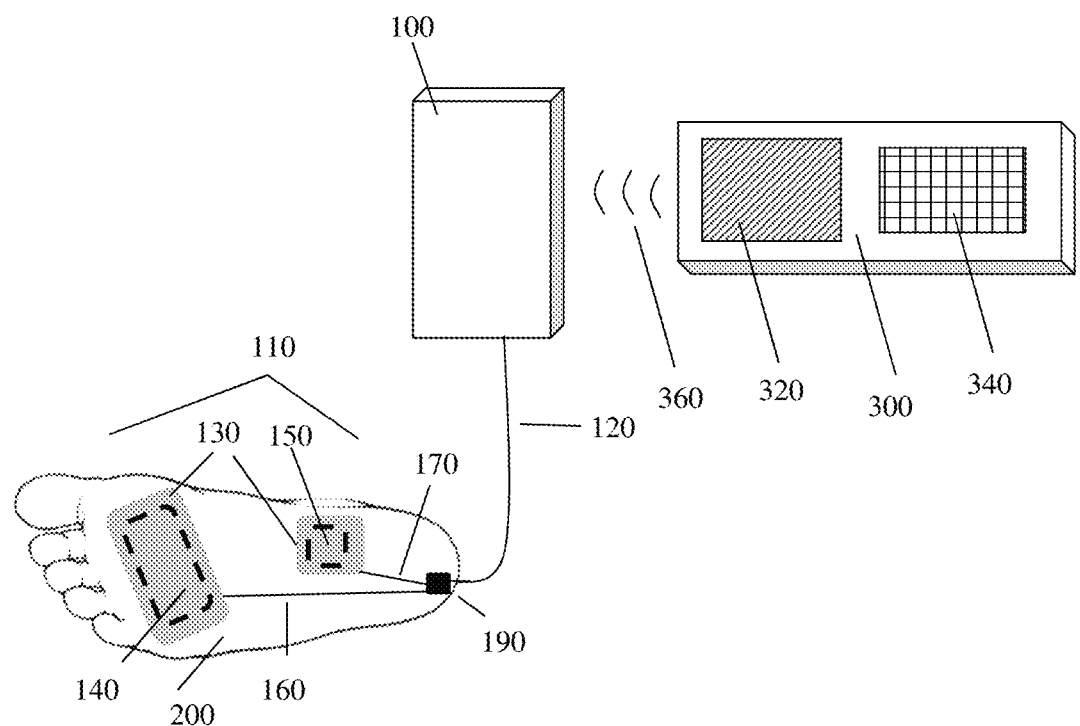
FIG. 11 is a schematic diagram of one aspect of a system including a device for placement on a plantar surface of the foot as described herein.
Figure 12:
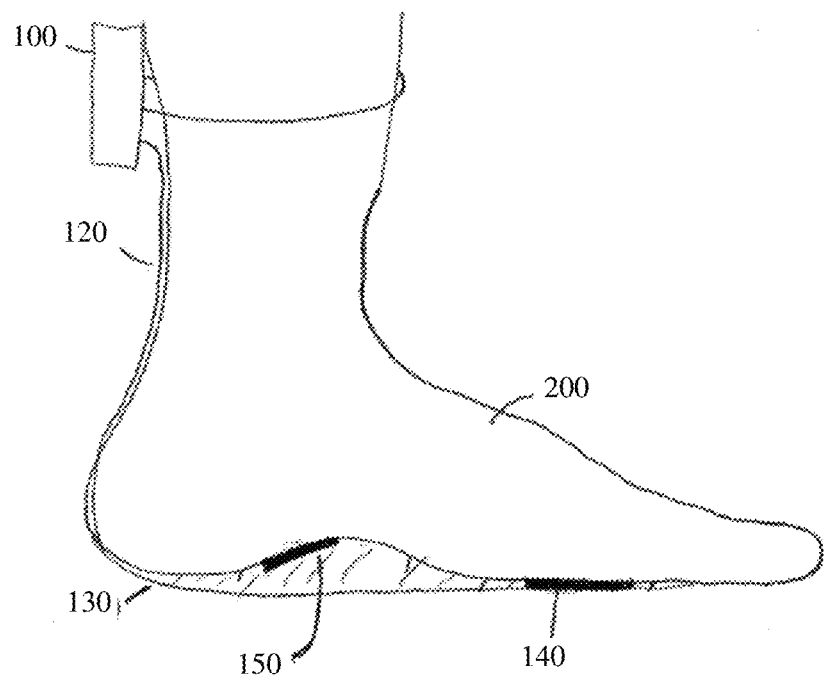
FIG. 12 is a schematic diagram of one aspect of a system including a device for placement on a plantar surface of the foot as described herein.

Turning to FIGS. 11-13, depicted schematically is one aspect of a system for stimulating foot nerves according to the device and methods described herein. Structures are out of proportion to facilitate illustration of elements of the depicted system. Pulse generator 100 is depicted as having one output channel, though an increased number of output channels falls within the scope and spirit of the invention. Wire 120 is attached by leads 160 and 170 to second electrode 140 and first electrode 150, respectively, which are attached to (e.g., affixed to, embedded in or integrated into) the base 130 of the electrode-containing device 110, and are thereby adapted to the plantar side of the foot across the forefoot region (electrode 140) and hindfoot region (electrode 150) of a foot 200. In the depicted aspect, only a single, multi-conductor wire 120 connects pulse generator 100 to the leads 160, 170 of electrode-containing device 110 through connector 190, but the single wire contains at least a plurality of leads, for connecting to the anode and cathode. Another aspect (not shown), employs a plurality of wires, one carrying lead(s) for cathode(s) and others carrying lead(s) for anode(s), rather than single wire 120. In the aspect of FIG. 11, electrode 140 is shown on the plantar side of the foot at the forefoot while electrode 150 is shown at the hindfoot.

Output parameters of the pulse generator 100 can be controlled via a wired interface, but also may be controlled by wireless transmission, as shown in the aspect of FIG. 11, which can be carried any suitable wireless protocol, such as radio frequency, IEEE 802.11a/ac/b/g/n, Bluetooth, ZigBee (IEEE 802.15), etc. Thus, an external controller 300 is depicted for communicating with a receiver in the pulse generator 100. External controller 300 is depicted as having a display 320, such as an LCD, LED or OLED display, and a keypad 340 for entering data into the external controller 300. External controller is depicted as sending a wireless transmission 360 to pulse generator 100, though in another aspect, data can be transferred both to the pulse generator 100 from the external communicator 300 and vice-versa, to permit monitoring of one or more parameters of pulse generator 100, including, without limitation, output signal characteristics (e.g., frequency, amplitude, etc. as outlined above) and battery strength. Smartphones, tablets or computers may be used as controllers, software, such as iOS, Android or Windows-based "apps" may be developed to act as controllers for these devices.

Likewise, wireless transmission 360 can be replaced by a wire or other conductor. In such a case, the controller may be housed within the same housing as the pulse generator. Activity of pulse generator 100 and external controller 300 typically is microprocessor controlled and software/firmware installed onto the pulse generator 100 and external controller 300 hardware may be used to implement the described tasks, and to provide, for example and without limitation, a graphical user interface (GUI) for the display 320, which facilitates use of the system. Both pulse generator 100 and external controller 300 may comprise any suitable electrical and electronic components to implement the pulse, communication, feedback, adjustment, etc. activities including, microprocessors, memory (e.g., RAM, ROM. Flash memory, etc.), connectors, batteries, power transformers, amplifiers, software (including, for example and without limitation: firmware, operating systems, utilities, processes, routines), etc. A person of skill in the electronic arts will be able to implement such a system using readily-available electronics parts and ordinary programming skills. Proprietary chips, chipsets, etc. may be designed and manufactures to implement the devices described herein. Elements of the system depicted in FIG. 11, such as a battery and a pulse generator can be integrated into an aesthetically-pleasing housing, such as an anklet, such as is schematically illustrated in FIG. 12.

With continuing reference to FIG. 11, pulse generator 100 may be connected (at 190) to electrode-containing device 110 through any suitable connection that can transmit pulses provided by pulse generator 100 to the device 110 abutting the plantar surface of an individual's foot 200. Pulse generator 100 and electrode-containing device 110 may be permanently connected through wiring, or through a releasable coupling or connector. Pulse generator 100 may be a device that can be attached to the individual wearer's ankle, shoe, or any other suitable place for the pulse generator 100 to provide the pulses necessary to stimulate the nerves of the foot through electrode-containing device 110.

The external controller 300 may be a proprietary device that is specifically designed for the task, or a non-proprietary device, such as a commercial TENS controller, smart phone, tablet, personal computer or a portable computer. Pulse generator 100 may comprise any number of channels, so long as the number of channels needed to implement a desired method is provided.

With continuing reference to the system of the present invention, FIG. 12 shows a side view of one aspect of the system, including electrode-containing device 110, base 130, electrodes 140, 150, and pulse generator 100. A wireless controller (not shown) may provide instructions to pulse generator to provide sufficient stimulation through wire 120 containing leads for the anode and cathode to stimulate nerves of the foot 200. Pulse generator 100 may be a device that is suitable for attachment around the ankle or lower leg of a patient, such that it can be disguised/hidden from view while still providing stimulation to the patient's foot 200. Wire 120 containing leads may be placed between the wearer's leg/ankle and a garment (sock, hose, or the like) for a thin film-type electrode-containing device (not shown), or may overlay a garment (sock, hose, or the like) for an orthotic-type electrode containing device 110.

Returning to FIG. 11, a potential difficulty with use of wireless devices such as a wireless controller for communicating instructions to a pulse generator capable of receiving wireless instructions is one of identity. A controller 300 should only be able to control one pulse generator 100 to prevent accidental stimulation of unintended subjects, or even intentional stimulation. In its simplest form, the transmission range of the devices can also be limited to prevent transmission over distances more than a few feet, thereby limiting the chances of unintended stimulation (crosstalk). Also, any number of identity verification mechanisms may be utilized to prevent crosstalk. In one aspect, different transmission wavelengths may be used for different devices, thus lowering the likelihood of crosstalk. In another aspect, the pulse generator 100 is programmed to only respond to a transmission containing a pre-defined signal, such that the pulse generator 100 and external wireless controller 300 must first, and/or periodically "handshake" in order to communicate. Likewise, the pulse generator 100 and/or controller 300 may transmit encrypted signals which only can be decrypted by a key stored in the other of the pulse generator 100 and/or controller 300. In another aspect, RFID tagging technology may be used to ensure that the controller 300 and pulse generator 100 match. Any combination of these proximity and/or identity verification measures may be used to prevent cross-talk. Other useful technologies for ensuring security and identity in communication are, or may be available and are equally applicable.

Figure 14:
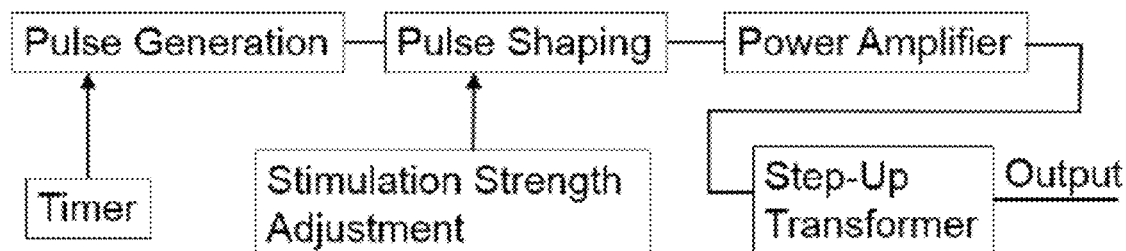
FIG. 14 is a block diagram of electronic design of a device as described herein.

With regard to FIGS. 13 and 14, shown therein are one aspect of a device and system according to the present invention. FIG. 13 shows a small, inexpensive, and easy-to-use stimulator for foot neuromodulation, including two units: a disposable unit and an electronic unit. The disposable unit (a) has an insole shaped substrate or base (130) made of a soft, transparent polymer, which serves multiple purposes, including to match different sizes of the foot, and to pre-fix the electrode locations. Two electrodes (140, 150) are included, and can be formed of, for example and without limitation, copper foils plated with silver—silver chloride. These electrodes can be heat-printed on the surface of the substrate (base) (130). In this aspect, each of the electrodes (140, 150) are connected to an electrode connector (190), made of a thick, high-quality paper.

The connector (190) can be folded along a perforated line (197) to be connected with a strap (199) in the electronic unit (b) (100) using a snap button (195). The silver—silver chloride surface of each electrode can be pre-applied with a conductive adhesive, forming a proper electrical interface with the skin enabling an effective stimulation of the tibial nerve (or branches thereof, as described herein). In the illustrated aspect, the electronic unit (b) (100) is located on top of the foot. On the top panel (not shown) of the electronic unit (100), there can be three main components: a switch/potentiometer combo to turn on/off the power and control the stimulation strength, two LED lights indicating the power and working status of the system, and a timer switch which, when activated, automatically stops stimulation after a pre-set period of time. On the side panel of electronic unit (100), there can be located a standard or mini USB socket (not shown) for recharging the battery (for example, lithium-ion) inside the electronic unit (100). The straps (199) have three functions: 1) making an electrical connection to the electrodes (140, 150), 2) securing the insole (substrate—130) and the electronic unit (100), and 3) facilitating observation and hand access to the top panel for adjusting the stimulation strength.

The block diagram of the circuitry within the electronic unit is shown in FIG. 14. In the illustrated aspect, a non-linear oscillator produces a square wave of a desired frequency. A timer controls the oscillator for automatic shutdown. The square wave is processed by the pulse shaping circuit producing a signal with narrow pulses. A potentiometer controls the pulse width which, when the signal passes through the step-up transformer, can also effectively control the strength of the stimulation. The power amplifier provides a sufficient signal power to drive the step-up transformer. With a 3.7 V, 500 mAh lithium-ion rechargeable battery as the power supply, the device can produce 5 Hz, approximately 0.2 ms stimulation pulses with adjustable peak amplitude between 0-100 V.

Also provided herein is a method of using the electrode-containing device, including the other components of the system such as a pulse generator and controller, for stimulating a physiological response in a subject, such as modulation of urological, bladder, gastrointestinal, and/or rectal activity, for example one or more of: overactive bladder (OAB) symptoms including bladder overactivity, urinary frequency, urinary urgency, urinary incontinence (including bedwetting), interstitial cystitis (IC), urinary retention; pelvic pain; fecal incontinence; irritable bowel syndrome (IBS); and constipation. The method includes stimulating nerves of the foot of a patient a device and system according to any aspect described herein, with electrical pulses at a frequency and amplitude able to either inhibit one or more of bladder contractions, rectum contractions, urination, defecation, and pelvic pain of the bladder, urethra, prostate, anus or rectum, thereby obtaining the physiological response. The physiological response may be one or more of inhibition of micturition, defecation, bladder contractions, pelvic pain of bladder, urethra, prostate, anus, or rectum, and inhibition of rectal contractions.

In one aspect, the electrical pulses range from 1 Hz to 500 Hz, such as 1-50 Hz, 5-20 Hz, or 5 Hz and all subranges therebetween and overlapping therewith. Pulsewidth may be from 0.01 to 3 ms and all subranges therebetween and overlapping therewith. Voltage may range from 1-100 V, such as from 1-20 V or from 3-16 V, including all subranges therebetween and overlapping therewith. Current may range from 1 mA to 100 mA. These ranges include all subranges therein, for example 5-95 mA, 10-90 mA, 15-85 mA, 20-80 mA, 25-75 mA, 30-70 mA, 35-65 mA, 40-60 mA, and subranges therebetween and overlapping therewith.

The aforementioned parameters may be adjusted to provide from 2T to 6 T, which is suitable for, for example, inhibition of bladder contractions; rectum contractions; for treatment of urological conditions, such as overactive bladder (OAB) symptoms including bladder overactivity, urinary frequency, urinary urgency, urinary incontinence (including bedwetting), interstitial cystitis (IC), urinary retention, and pelvic pain, and for treatment of gastrointestinal conditions, such as fecal incontinence, irritable bowel syndrome (IBS), and constipation. The pulses may be applied intermittently, for example and without limitation, in two or more stimulation intervals of, for example and without limitation, from 0.5 to 200 seconds, with a rest period of no electrical stimulation, able to inhibit bladder or rectal contractions between stimulation intervals, or may be applied continuously. Typically during the rest period, no inhibitory stimulus is applied. During the rest period no electrical signal, or essentially no electrical signal is applied. The stimulation protocol may be applied for from between 1 and 360 minutes per day, for example, at least 15, 30, 45, 60, 75, 90, or more minutes per day. The parameters identified as possible and useful herein, for example in discussion of the device and systems above, may be applied to the methods described herein.

As also provided by the following examples, neuromodulation by means of administration of pharmacological substances, in addition to or in place of neuromodulation by electrical stimulation of the foot, can likewise induce either inhibitory or excitatory effect depending on the state of the CNS (that is, exciting or inhibiting an organ). A treatment strategy that combines foot stimulation with low-doses of drugs such as tolterodine or tramadol to enhance OAB treatment efficacy lowers the potential for unwanted side effects (Mally A D et al. Combination of foot stimulation and tramadol treatment reverses irritation induced bladder overactivity in cats. *J Urol* 188: 2426-2432, 2012; Schwen Z et al. Combination of foot stimulation and tolterodine treatment eliminates bladder overactivity in cats. *Neurourol Urodyn* 2013; in press). The additive effect of neuromodulation and drug therapy has also been demonstrated clinically in patients who had incomplete responses to neuromodulation therapy alone (George E et al. Use of combined anticholinergic medication and sacral neuromodulation in the treatment of refractory overactive bladder. *Female Pelvic Med Reconst Surg* 17: 97-99, 2011).

Tramadol has opioid agonist activity and can synergistically enhance foot inhibition and produce a long-lasting post-stimulation inhibitory (Mally A D et al. Combination of foot stimulation and tramadol treatment reverses irritation induced bladder overactivity in cats. *J Urol* 188: 2426-2432, 2012). However, tramadol also acts as a serotonin-norepinephrine reuptake inhibitor (Grond S et al. Clinical pharmacology of tramadol. *Clin Pharmacokin* 43: 879-923, 2004). This raises the possibility that tramadol might also influence foot stimulation by enhancing serotonin and norepinephrine mechanisms. Other compounds with similar actions on the serotonergic and noradrenergic systems may also be utilized. For example, a low dose of duloxetine that is not effective in inhibiting the bladder alone administered in addition to electrical stimulation of the foot. Reducing the dose of duloxetine could minimize the noted side-effects of the compound and thus reduce patient dropout rate. Additionally, use of receptor antagonists, such as the $5HT_{1A}$ antagonist, WAY100635, may be utilized to augment duloxetine's effect on bladder overactivity, to inhibit $5HT_{1A}$ autoreceptors in the raphe nucleus.

Accordingly, provided herein is a method of treating urological and/or gastrointestinal disorders by combining the stimulation by any aspect of the foot stimulation devices, systems, and/or methods described herein with administration of one of, or a combination of, a serotonin/norepinephrine reuptake inhibitor and/or a serotonin/norepinephrine receptor ($5HT_{1A}$) antagonist/blocker. Suitable serotonin/norepinephrine reuptake inhibitors include, without limitation, selective serotonin reuptake inhibitors (SSRIs) such as alaproclate, citalopram, dapoxetine, escitalopram, femoxetine, fluoxetine, fluvoxamine, ifoxetine, indalpine, omiloxetine, panuramine, paroxetine, pirandamine, duloxetine, dapoxetine, sertraline, and/or zimelidine. Suitable serotonin receptor antagonists/blockers include alprenolol, AV-965, BMY-7,378, cyanopindolol, dotarizine, flopropione, GR-46, 611, isodocyanopindolol, isamoltane, lecozotan, methiothepin, methysergide, MPPF, NAN-190, oxprenolol, pindobind, pindolol, propranolol, risperidone, robalzotan, SB-649,915 (which acts as both a reuptake inhibitor and a receptor antagonist), SDZ-216,525, spiperone, spiramide, spiroxatrine, UH-301, WAY100135, WAY 100635, and/or xylamidine. In one aspect, the reuptake inhibitor is duloxetine and the receptor antagonist/blocker is WAY100635. According to one aspect, a combination dosage form is provided, that includes a combination of a serotonin/norepinephrine reuptake inhibitor and a serotonin/norepinephrine receptor ($5HT_{1A}$) antagonist/blocker, such as any combination of a serotonin/norepinephrine reuptake inhibitor and a serotonin/norepinephrine receptor ($5HT_{1A}$) antagonist/blocker described above. As an example, formulation of useful oral dosage forms is well within the skill of an ordinary artisan.

Previous studies investigating antidepressant effects of serotonin-norepinephrine reuptake inhibitors have shown that their action on central serotonergic pathways can be amplified when combined with WAY100635 (Bjorvatn B et al. Venlafaxine and its interaction with WAY100635: effects on serotonergic unit activity and behavior in cats. *Eur J Pharmacol* 404: 121-132, 2000; Marchand F et al. Blockade of supraspinal $5-HT_{1A}$ receptors potentiates the inhibitory effect of venlafaxine on wind-up activity in mononeuropathic rats. *Brain Res* 1008: 288-292, 2004). Because duloxetine's primary mechanism of action on the bladder is also believed to be through central serotonergic regulation of bladder function (Thor KB. Serotonin and norepinephrine involvement in efferent pathways to the urethral rhabdosphincter: implications for treating stress urinary incontinence. *Urol* 62(4 Suppl 1): 3-9, 2003), use of a central receptor antagonist, such as WAY100635, can enhance the effect of duloxetine on bladder overactivity.

Also provided herein is a method of treating urological and/or gastrointestinal disorders by combining stimulation using any aspect of the foot stimulation device, system, and method described herein in combination with administration of an anti-muscarinic compound. Anti-muscarinic compounds are anti-cholinergic compounds acting specifically on muscarinic cholinergic receptors. The method of stimulating the dorsal or plantar surface of the foot described herein may be combined with treatment, prior to, following, or concomitant with the stimulation, with one or more of atropine, benztropine, biperiden, ipratropium, oxitropium, tiotropium, glycopyrrolate, oxybutynin, tolterodine, chlorpheniramine, diphenhydramine, dimenhydrinate, orphenadrine, trihexyphenidyl, and/or dicyclomine. In one aspect, the anti-muscarinic agent used is tolterodine, given prior to stimulation.

Also provided herein is a method of treating urological and/or gastrointestinal disorders by combining stimulation using any aspect of the foot stimulation device, system, and method described herein with administration of an opioid compound. Suitable opioid compounds for use in the method include morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine, buprenorphine, fentanyl, pethidine, levorphanol, methadone, tramadol, dextropropoxyphene, tapentadol, endorphins, enkephalins, dynorphins, and endomorphins. In one aspect, the opioid compound is morphine.

As used herein, any of the above-described agents used for treating urological and/or gastrointestinal disorders is administered in any amount deemed useful by a healthcare practitioner. In one aspect, the agent(s) is/are administered in an amount effective to reduce symptoms of overactive bladder, decrease urinary frequency, increase urine retention, reduce amplitude of mictruition contractions, reduce symptoms IC, reduce pelvic pain, reduce fecal incontinence, reduce symptoms of IBS, and reduce constipation when used as described in combination with foot stimulation by any device, system or method described herein.

According to one aspect, an effective dose ranges from 0.001 to 200 mg/kg/day, and in certain aspects less than 100 mg/kg/day, including any increment or range therebetween, including 0.1 mg/kg/day, 0.5 mg/kg/day, 1 mg/kg/day, 5 mg/kg/day, 10 mg/kg/day, 20 mg/kg/day, 25 mg/kg/day, 50 mg/kg/day, 75 mg/kg/day, 100 mg/kg/day 125 mg/kg/day, 150 mg/kg/day, 175 mg/kg/day, and 200 mg/kg/day. However, for each compound described herein, an effective dose or dose range is expected to vary from that of other compounds described herein for any number of reasons, including the molecular weight of the compound, bioavailability in the dosage form, route of administration, specific activity (e.g., $EC_{50}$), etc. In any case, the effective range (e.g., the therapeutic window) between the minimally-effective dose, and maximum tolerable dose in a subject can be determined empirically by a person of skill in the art, with end points being determinable by in vitro and in vivo assays, and/or are acceptable in the pharmaceutical and medical arts for obtaining such information regarding agents, such as anti-muscarinic compounds, serotonin and/or norepinephrine reuptake inhibitors, serotonin and/or norepinephrine receptor antagonists/blockers, and opioids. Different concentrations of the agents described herein are expected to achieve similar results. The compounds can be administered orally one or more times daily, for example two to four times daily, once every two, three, four, five or more days, weekly, monthly, etc., including increments therebetween. In certain delivery methods, it is possible to deliver the drug continuously, or substantially continuously as in the case of, for example, intravenous or transdermal delivery routes. A person of ordinary skill in the pharmaceutical and medical arts will appreciate that it will be a matter of design choice and/or optimization to identify a suitable dosage regimen for achieving the purpose of the present method(s).

The compounds described herein may be administered in any manner that is effective to reduce symptoms of overactive bladder, decrease urinary frequency, increase urine retention, reduce amplitude of mictruition contractions, reduce symptoms IC, reduce pelvic pain, reduce fecal incontinence, reduce symptoms of IBS, and reduce constipation. Examples of delivery routes include, without limitation: topical, for example, epicutaneous, inhalational, enema, ocular, otic and intranasal delivery; enteral, for example, orally, by gastric feeding tube or swallowing, and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral or inravenous approaches being preferred.

Therapeutic/pharmaceutical compositions are prepared in accordance with acceptable pharmaceutical procedures, such as described in *Remington: The Science and Practice of Pharmacy,* 21st edition, ed. Paul Beringer et al., Lippincott, Williams & Wilkins, Baltimore, MD Easton, Pa. (2005) (see, e.g., Chapters 37, 39, 41, 42 and 45 for examples of powder, liquid, parenteral, intravenous and oral solid formulations and methods of making such formulations).

Any of the compounds described herein may be compounded or otherwise manufactured into a suitable composition for use, such as a pharmaceutical dosage form or drug product in which the compound is an active ingredient. According to one example, the drug product described herein is an oral tablet, capsule, caplet, liquid-filled or gel-filled capsule, etc. Compositions may comprise a pharmaceutically acceptable carrier, or excipient. An excipient is an inactive substance used as a carrier for the active ingredients of a medication. Although "inactive," excipients may facilitate and aid in increasing the delivery, stability or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Also provided herein is a method of manufacturing an electrode-containing device and system as described herein. The method comprises forming a base shaped or adapted to the dorsal or plantar surface of a human foot and having an anterior-posterior axis. The material(s) used to form the base may be any suitable materials such as, without limitation, gels, foams, rubbers, silicon-based products, polymers, neoprene, animal hides, leathers, polyethylene, ethyl vinyl acetate, polypropylene, polyimide, polyester, polyethylene terephthalate, polyaryletheretherketone, polytetrafluoroethylene, polyethylene naphthalate, co-polymer plastics, and combinations thereof. The material is preferably substantially nonconductive. Those of skill in the art are aware of methods for forming and casting bases from the identified materials, for example gelling, polymerizing, molding, vulcanizing, and the like.

The method further includes the steps of introducing a first electrode having a lead at a posterior portion of the base and introducing a second electrode having a lead at an anterior portion of the base. The leads of the electrodes may be provided with the electrodes prior to attachment to the base, or attached to the electrodes during or after incorporation of (attachment of) the electrodes into the base. The first electrode is positioned as described above to contact skin overlaying the hindfoot and specifically the superficial peroneal nerve, deep peroneal nerve, and/or saphenous nerve (or, if the plantar surface of the foot is to be stimulated, the first electrode is positioned and oriented on the base to contact skin of the hindfoot, more specifically overlaying the medial and lateral plantar nerves in the posterior of the medial longitudinal arch). The second electrode is positioned and oriented on the base to contact skin of the forefoot, more specifically overlaying the superficial peroneal nerve and branches thereof (e.g. dorsal intermediate and dorsal medial cutaneous nerves), deep peroneal nerve, sural nerve, and/or saphenous nerve (or the medial and lateral plantar nerves). However, as described above, the electrodes (i.e. their polarity) may be reversed, such that the first electrode is located anteriorly and the second electrode is located posteriorly.

As described above, the electrodes and leads may be formed of any suitable material, such as, without limitation, metals and metal foils, such as, for example and without limitation, copper, gold, silver, tin, nickel, steel, cupronickel, nickel-cobalt ferrous alloys, and carbon-based materials. The base and electrodes are formed in a manner such that the second electrode at the anterior position is configured to engage at least a portion of the forefoot of a human foot and configured such that it covers at least 50% of the width of the forefoot, and wherein the electrode at the posterior position is configured to engage the skin overlaying at least a portion of the calcaneus bone and/or talus bone of a human foot and configured such that it overlays the superficial peroneal nerve, deep peroneal nerve, and/or saphenous nerve on skin on the dorsal surface of the foot overlaying a portion of the calcaneus bone and/or talus bones and/or talocrural joint.

As described in detail elsewhere herein, the base may be formed in a plurality of sizes, widths, contours, etc. In aspects, the electrodes are not replaceable and are embedded within the base. In other aspects, the electrodes are replaceable, and only electrode leads and connections for electrodes are embedded within the base. In such aspects, the connector may also be embedded within the base.

The following are non-limiting examples of the use of electrical stimulation of the foot to inhibit bladder contraction, and are exemplary only and are not intended to limit the scope of the inventions described herein in any way.

Example 1

This study was approved by the Institutional Review Board at the University of Pittsburgh. Foot stimulation was tested in eight healthy humans without OAB (5 male and 3 female, 25-60 years old, Table 1).

TABLE 1

| Subject No.; Sex; Age | Volume/void during 24 h before stimulation (Mean ± SEM) (mL) | Volume/void during 5 h after stimulation (Mean ± SEM) (mL); No. voids in time after stimulation | Volume/void during 36 h after stimulation (Mean ± SEM) (mL) |
|---|---|---|---|
| 1; male; 46 | 368 ± 63 | 667 ± 106; 3 in 1:50 | 465 ± 69 |
| 2; male; 49 | 436 ± 25 | 755 ± 33; 3 in 2:50 | 388 ± 18 |
| 3; male; 41 | 206 ± 26 | 200 ± 0; 2 in 4:45 | 175 ± 28 |
| 4; male; 40 | 406 ± 71 | 577 ± 15; 3 in 5:00 | 469 ± 55 |
| 5; male 25 | 444 ± 26 | 600 ± 25; 1 30 min into stim and 1 in :10 | 368 ± 30 |
| 6; female; 48 | 173 ± 11 | 195 ± 15; 2 in 1:30 | 238 ± 19 |
| 7; male; 47 | 323 ± 54 | 530 ± 80; 2 in 2:10 | 263 ± 26 |
| 8; female; 60 | 538 ± 78 | 800 ± 0; 1 in 1:35 | 581 ± 74 |

The subjects were instructed to record daytime voided volumes during a 3-day period without any restriction on their daily food and water intake. They were also instructed to void in response to their usual bladder sensations and to note any void that was withheld or induced early due to unexpected situations. Those voiding volumes that resulted from unexpected situations were excluded from this study.

Foot stimulation was applied for 90 minutes in the morning (10:00 AM to 11:30 AM) on the second day while the subject was sitting. During the stimulation, the subject was asked to drink 1-2 bottles of water (500-1000 mL) so that a void could occur soon after stimulation. Two skin surface electrodes (LGMedSupply, Cherry Hill, NJ) were attached to the bottom of the foot. A large cathodal electrode (2 inch×3.5 inch) was placed on the front of the foot to cover as much skin area as possible and a small anodal electrode (2 inch×2 inch) was placed between the inner foot arch and the heel (similar to the arrangement shown in FIG. 6A). The electrodes were connected to a transcutaneous electrical nerve stimulator (LG-TEC ELITE, LGMedSupply, Cherry Hill, NJ) that provided constant current, rectangular pulses of 5 Hz frequency and 0.2 ms pulse width. The subject controlled the stimulator to determine the minimal current needed to induce a toe twitch. The stimulation intensity was then increased to a maximal level (25-60 mA) comfortable to the subject for the entire 90 minute stimulation, which ranged between 2-6 times the minimal intensity necessary to induce a toe twitch (T).

The volume per void was averaged among the subjects over three time periods: 1) 24 hours prior to foot stimulation; 2) up to 5 hours after stimulation; and 3) up to 36 hours after stimulation. The second time period always included the first void after the stimulation. However, if the voided volumes remained elevated in the following 1-2 voids, they were also included in the second time period (see Table 1). Therefore, the second time period was variable ranging up to 5 hours, which is indicated in the third column in Table 1. The third time period includes voids up to 36 hours after stimulation, excluding the voids counted in the second time period. One-way ANOVA followed by Dunnett's multiple comparison was used to detect statistically ($p<0.05$) significant differences between voided volumes before and after stimulation.

Figure 15:
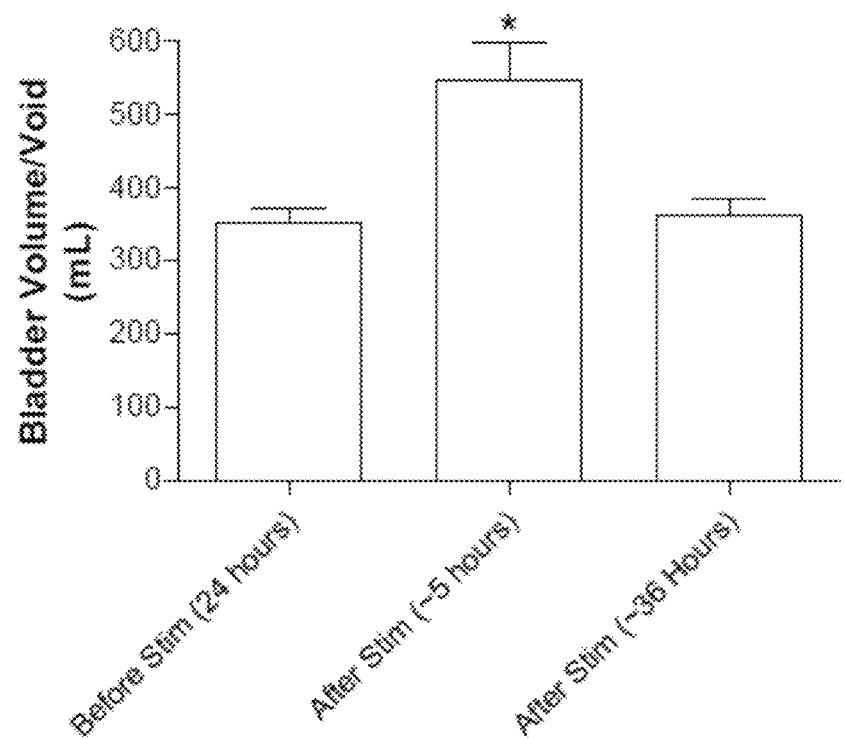
FIG. 15 shows the mean bladder volume per void measured during a 24-hour period before foot stimulation, after foot stimulation within a 5 hour period, and after foot stimulation during a 36 hour period.

The average volume per void was 350±22 mL during the 24 hour period prior to foot stimulation, and this volume increased to 547±52 mL ($p<0.01$) for up to 5 hours after the stimulation (see FIG. 15 and Table 1). The average voided volume returned to 363±21 mL within 36 hours after stimulation. The volume per void remained elevated for several hours following the stimulation in 3 consecutive voids (subjects #1, #2, and #4, Table 1) or 2 consecutive voids (subjects #6, and #7, Table 1). These subjects did not void during the stimulation. However, subject #5 voided 625 mL 30 minutes into the stimulation period. He again voided 575 mL 10 minutes after completing the 90-minute stimulation (average 600±25 mL, see Table 1). Both voided volumes were much larger than the mean voided volume of 444±26 mL prior to stimulation. The stimulation intensity threshold (T) to induce a toe twitch varied from 10 mA to 16 mA in the 8 subjects. The intensity used for the 90 minute stimulation session varied from 2 T to 3 T (24-36 mA) in 7 subjects. In one subject (#8), a stimulation intensity of 6 T (60 mA) was used. All subjects tolerated their stimulation without any discomfort. There was no observable change in the toe twitch during the stimulation. There were no immediate (i.e. local skin reaction) or long-term adverse events.

Example 2

Experiments were performed in a total of 8 adult anesthetized cats (5 female and 3 male cats between 3.1-4.4 kg). Each cat was anesthetized with isoflurane (2-3% in O2) during surgery and then changed to α-chloralose (65 mg/kg, supplemented as necessary) anesthesia during data collection. A pulse oximeter (9847V, Nonin Medical Inc., Plymouth, MN, USA) with the sensor attached to the tongue was used to monitor heart rate and blood oxygen saturation. Catheters were inserted in the right cephalic vein and right carotid artery for intravenous infusion of drugs and monitoring systemic blood pressure, respectively. Airway access was secured with a tracheostomy tube. Ureters were accessed through a midline abdominal incision and drained externally. The bladder was then cannulated with a double lumen catheter through a small cut at the proximal urethra to infuse saline or 0.25% AA and simultaneously measure bladder pressure. The proximal urethra was tied to prevent leakage. Fur was removed from the right hind foot and two self-adhesive pad electrodes (Grass FE10ND, Astro-Medical Inc., Mentor, OH, USA; diameter 1 cm) were attached to the skin at the bottom of the foot. One electrode was at the front of the foot and the other was at the heel (Chen G et al. Post-stimulation inhibitory effect on reflex bladder activity induced by activation of somatic afferent nerves in the foot. *J Urol* 187: 338-343, 2012; Tai C et al. Suppression of bladder overactivity by activation of somatic afferent nerves in the foot. *BJU Int* 107: 303-309, 2011).

Stimulation Protocol and Drug Administration

Uniphasic rectangular pulses (5 Hz frequency, 0.2 ms pulsewidth) were delivered to the surface electrodes on the foot. Stimulation intensity threshold (T) was defined as the minimal intensity to induce a toe twitch. Foot stimulation of intensities 2-4 T was used in this study since previous studies demonstrated that this intensity range was effective in inhibiting reflex bladder contractions (Chen G et al. Post-stimulation inhibitory effect on reflex bladder activity induced by activation of somatic afferent nerves in the foot. *J Urol* 187: 338-343, 2012; Mally A D et al. Combination of foot stimulation and tramadol treatment reverses irritation induced bladder overactivity in cats. *J Urol* 188: 2426-2432, 2012; Tai C et al. Suppression of bladder overactivity by activation of somatic afferent nerves in the foot. *BJU Int* 107: 303-309, 2011). Initially the bladder capacity was determined during cystometrograms (CMGs) by slowly infusing the bladder with saline. Multiple CMGs were performed to ensure reproducibility of the saline control capacity.

Bladder capacity was defined as the bladder volume threshold required to induce a micturition contraction of large amplitude (>30 cm $H_2O$) and long duration (>20 seconds). Then, repeated CMGs were performed with infusion of 0.25% AA to irritate the bladder, activate nociceptive bladder afferent C-fibers, and induce bladder overactivity. When the bladder capacity stabilized, four CMGs were performed with AA infusion (Infusion rate=2 mL/min) prior to the administration of duloxetine: (1) control without stimulation, (2) during 2 T stimulation, (3) during 4 T stimulation, and (4) control without stimulation to determine any post-stimulation effect. The bladder was emptied at the end of each CMG and a 3-5 minute rest period was inserted between CMGs.

After the pre-drug CMGs were performed, increasing cumulative doses (0.003, 0.01, 0.03, 0.1, 0.3, 1, and 3 mg/kg, i.v.) of duloxetine (Selleck Chemicals, Houston, TX) were given to determine the drug effect on bladder capacity. Ten minutes after administering each dose of duloxetine, the four CMGs were again performed with AA infusion under different conditions (control, 2 T stimulation, 4 T stimulation, and post-stimulation control). The four repeated CMGs were completed within 40-60 minutes. In 4 cats 50-70 minutes after giving the maximal dose of duloxetine (3 mg/kg), WAY100635 (Sigma-Aldrich, St. Louis, MO), a $5HT_{1A}$ antagonist, was administered (0.5 mg/kg, i.v.) to block $5HT_{1A}$ inhibitory autoreceptors on serotonergic neurons in the raphe nucleus in an attempt to enhance the serotonergic inhibitory influence of duloxetine on bladder reflexes. Five minutes after administration of WAY100635, we performed control CMGs without stimulation to examine the combined effect of WAY100635 and duloxetine on bladder capacity.

Data Analysis

For each CMG, bladder capacity was normalized to the initial saline control capacity in the same animal, which allowed for comparisons between animals. The bladder capacities were averaged for each condition and reported with standard error of the mean. Student T-test, one way ANOVA followed by Dunnett post-tests, or two-way ANOVA followed by Bonferroni posttests was used to determine the statistical significance ($p<0.05$).

Results

Suppression of Bladder Overactivity by Foot Stimulation

Figure 16:
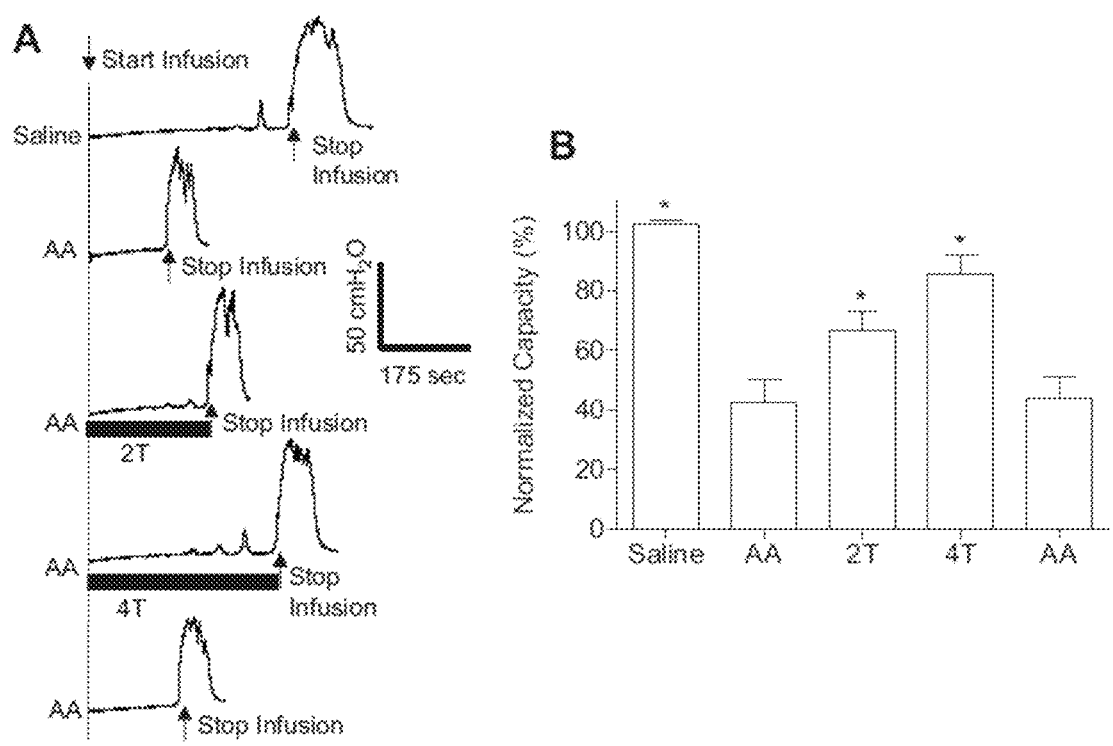
FIG. 16 shows foot inhibition of bladder overactivity induced by 0.25% acetic acid (AA) irritation before duloxetine treatment: A. Cystometrogram (CMG) pressure traces during saline or AA infusion with and without foot stimulation. B. Summarized bladder capacity under different CMG conditions (N=8 cats).

After saline control CMGs were performed, AA-induced bladder irritation significantly ($p<0.0001$) reduced bladder capacity to a mean of 42.7±7.4% (5.7±1.5 mL) of saline control capacity (11.8±1.8 mL) (FIG. 16). Foot stimulation significantly ($p<0.0001$) inhibited bladder overactivity and increased capacity to 66.7±6.3% at 2 T and 85.7±6.5% at 4 T of saline control (Foot stimulation threshold (T) defined as the minimal intensity to induce observable toe twitch. Stimulation: 5 Hz, 0.2 ms, T=11 V). Post-stimulation AA control capacity was not different from pre-stimulation AA control demonstrating that there was no post-stimulation effect on bladder capacity (FIG. 16). In FIG. 16, the black bar under bladder pressure trace represents the duration of stimulation.

Figure 17:
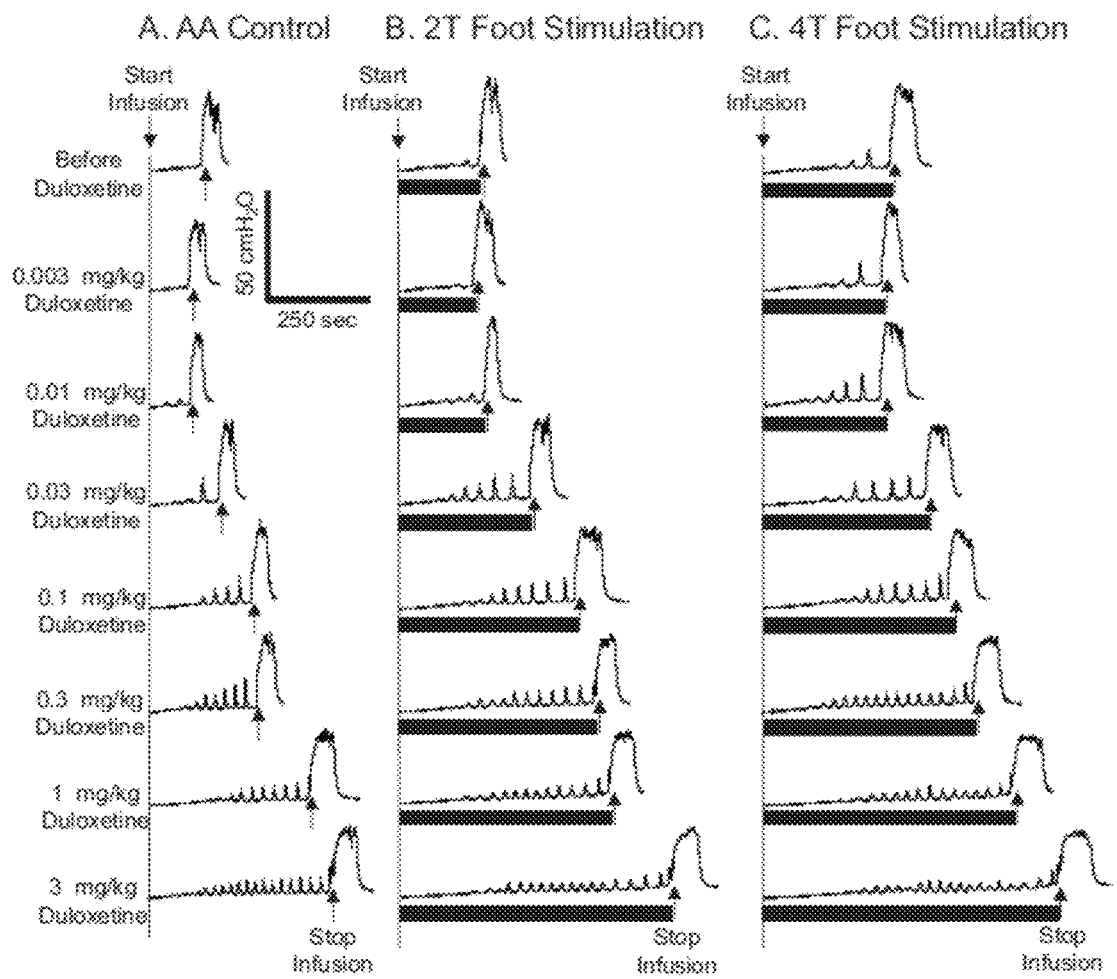
FIG. 17 shows CMG traces showing the dose-dependent effect of a range of intravenous doses of duloxetine and foot inhibition on bladder overactivity caused by AA irritation. A. Control CMGs without foot stimulation. B. CMGs during 2 T stimulation. C. CMGs during 4 T stimulation.
Figure 18:
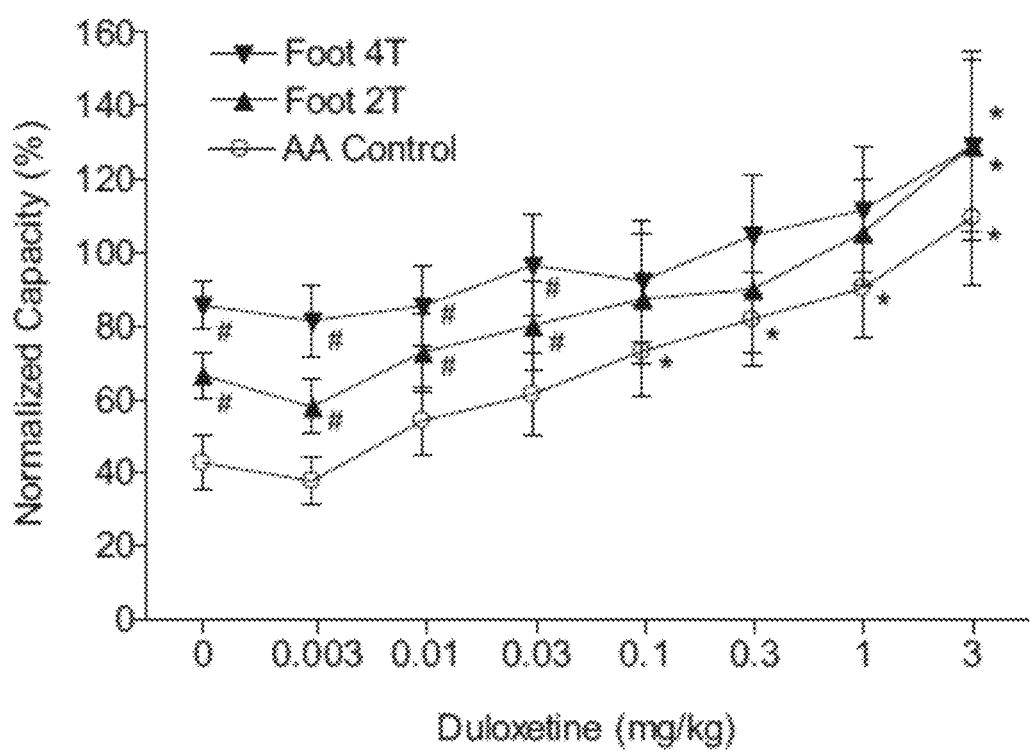
FIG. 18 shows summarized results of the dose-dependent effect of duloxetine administered intravenously and foot inhibition on bladder overactivity induced by AA irritation (N=8 cats).

Dose Dependent Effect of Duloxetine on Bladder Overactivity with and without Stimulation In the absence of stimulation, duloxetine dose-dependently and significantly ($p<0.05$) increased bladder capacity during AA infusion at doses 0.1-3 mg/kg, and completely removed AA-induced overactivity at 3 mg/kg increasing bladder capacity to 109±15.5% of saline control (FIGS. 17(A) and 18). In FIG. 17, the CMGs were performed in sequence from left to right in panels A-C and from top to bottom in each figure to examine a possible interaction between duloxetine and foot stimulation. Black bar under bladder pressure trace represents the duration of stimulation. When foot stimulation was combined with duloxetine, the stimulation significantly ($p<0.05$) increased capacity after doses ranging from 0.003 mg/kg to 0.03 mg/kg but did not significantly increase capacity after doses between 0.1 mg/kg and 3 mg/kg (FIGS. 17 and 18). After the highest dose (3 mg/kg), 2 T and 4 T stimulation significantly ($p<0.05$) increased the bladder capacity to 129.3±23.2% and 129.2±25.8% of saline control, respectively. After 2 T and 4 T stimulation in duloxetine treated animals, bladder capacity returned to pre-stimulation levels indicating an absence of a post-stimulation effect.

Combined Effect of Duloxetine and WAY100635

Figure 19:
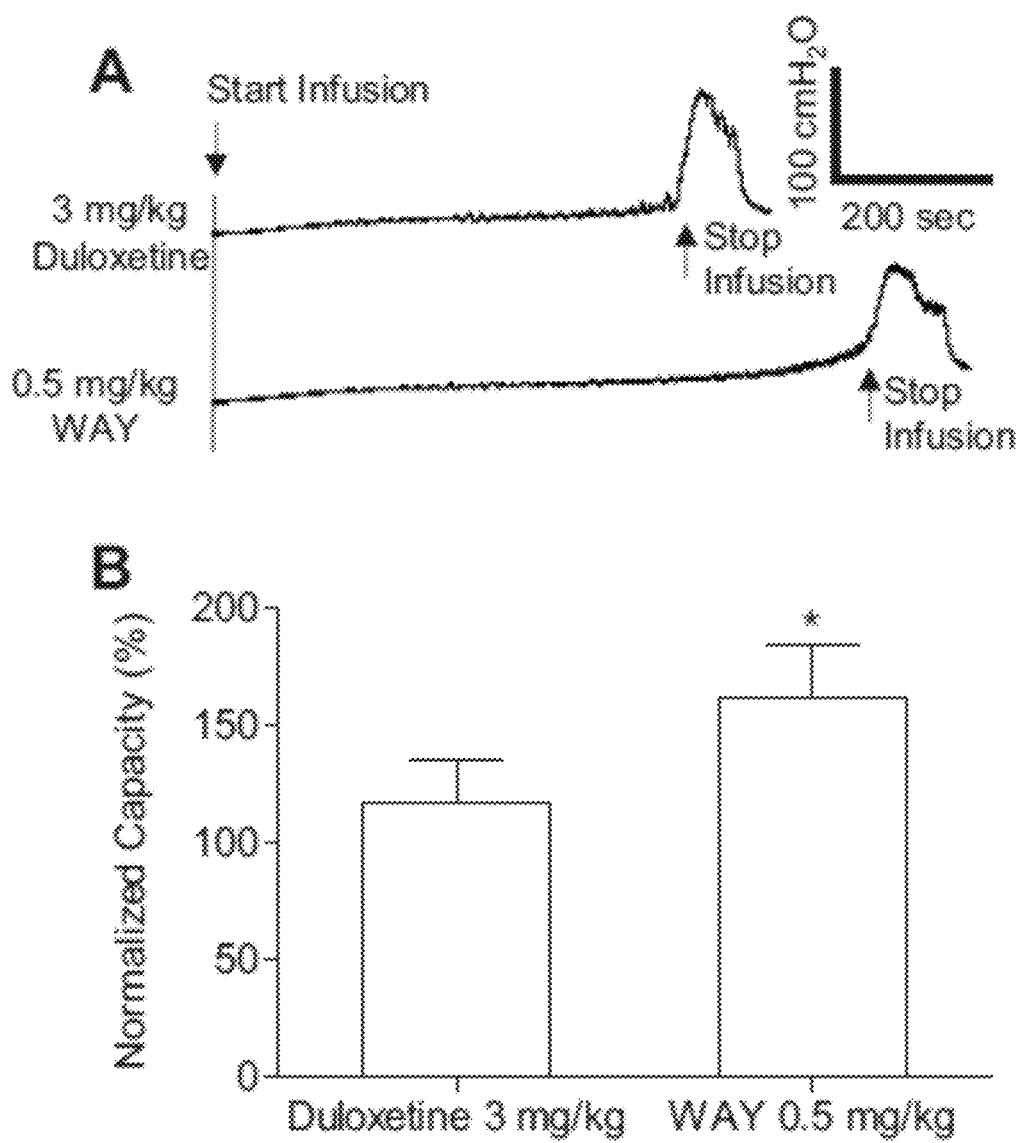
FIG. 19 shows inhibition of bladder overactivity induced by combination of duloxetine and WAY100635 treatment: A. CMG pressure traces during acetic acid (AA) infusion after 3 mg/kg duloxetine and then after 0.5 mg/kg WAY100635 intravenously. B. Summarized bladder capacities measured before and after WAY100635 treatment (N=4 cats).

After the final 3 mg/kg dose of duloxetine, intravenous injection of WAY100635 (0.5168 mg/kg), which is a dose that alone does not affect bladder capacity (20, 31, 36), significantly ($p=0.008$) increased bladder capacity from a mean of 117.3±17.6% to 162.2±22.5% of saline control (FIG. 19).

Example 3

Experiments were conducted in a total of 6 adult cats (4 female and 2 male cats between 2.8-3.8 kg) under achloralose anesthesia (65 mg/kg, supplemented as necessary) after induction with isoflurane (2-3% in $O_2$). Heart rate and blood oxygen level were monitored with a pulse oximeter (9847 V, Nonin Medical Inc., Plymouth, MN, USA) that was attached to the tongue. Systemic blood pressure was monitored via a catheter in the right carotid artery. These physiological parameters were monitored to ensure that the animal's vital functions remained relatively stable during the entire experiment. Drugs or fluids were administered through a catheter in the right cephalic vein and airway access was secured with a tracheostomy tube. Ureters were accessed through a midline abdominal incision and drained externally. The bladder was cannulated through the urethra with a double lumen catheter to infuse (1-2 ml/min) saline or 0.25% acetic acid (AA) via one lumen and measure bladder pressure via another lumen. A ligature was tied around the proximal urethra to prevent leakage. Fur was removed from the foot and two self-adhesive pad electrode (Grass FE10ND, Astro-Medical Inc., Mentor, OH, USA; diameter 1 cm) were attached to the skin at the bottom of the left hind foot. One electrode was at the front of the foot and the other was at the heel.

Stimulation Protocol and Drug Administration

Uniphasic rectangular pulses (5 Hz frequency, 0.2 ms pulsewidth) were delivered to the skin electrodes on the foot. Threshold (T) stimulation intensity (3-16 V), which was defined as the minimal intensity to induce an observable toe twitch, was determined by slowly increasing the stimulation intensity at the beginning of the experiment. Previous studies indicated that foot stimulation at 2 T is required to inhibit reflex bladder contractions.13 Therefore, we chose to use intensities of 2 T and 4 T to suppress bladder overactivity induced by AA irritation. The initial bladder capacity was determined during a cystometrogram (CMG) by slowly infusing the bladder with saline. Bladder capacity was defined as the bladder volume threshold to induce a bladder reflex contraction of large amplitude (>30 cm $H_2O$) and long duration (>20 seconds).

Multiple CMGs were performed to determine reproducibility of the saline control capacity. Then, repeated CMGs were performed with AA infusion to irritate the bladder, activate nociceptive bladder C-fiber afferents, and induce bladder overactivity. Once the irritated bladder capacity was stabilized, four CMGs were performed prior to drug administration: 1. control CMG without stimulation; 2. CMG during 2 T stimulation; 3. CMG during 4 T stimulation; and 4. control CMG without stimulation to determine any post-stimulation effect. Increasing cumulative doses of tolterodine (tolterodine L-tartrate, Tocris Bioscience, Bristol, UK) were then administered (0.003, 0.01, 0.03, 0.1, and 0.3 mg/kg, i.v.). Ten minutes after administering each dose of tolterodine, the CMGs were performed again under the four different conditions (control, 2 T stimulation, 4 T stimulation, and post-stimulation control) to determine the drug effect on bladder capacity. The bladder was emptied after each CMG followed by a 3-5 min rest period to allow the distended detrusor to recover.

Data Analysis

For the repeated CMG recordings, bladder capacity was normalized to the initial saline control capacity in the same animal to allow comparisons between animals. Capacity measurements under the same conditions were averaged and reported as mean±standard error of the mean (SEM). The mean amplitude of the bladder reflex contraction was also measured during each CMG and normalized to the AA control CMG to determine the effect of tolterodine on detrusor contractility. Statistical significance ($p<0.05$) was detected by ANOVA followed by Dunnett or Bonferroni post-tests.

Results

Suppression of Bladder Overactivity by Foot Stimulation

Figure 20:
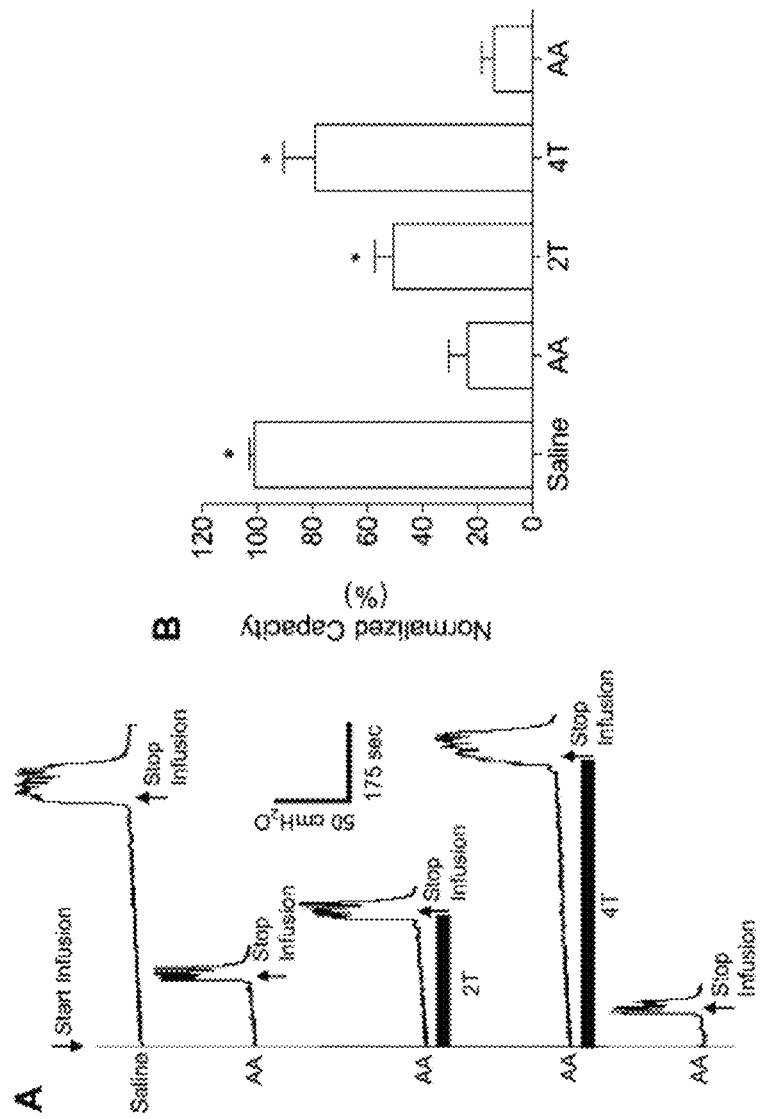
FIG. 20 shows foot inhibition of bladder overactivity caused by 0.25% AA: A. CMG pressure trace during saline or AA infusion at rate of 1 ml/min with or without foot stimulation prior to tolterodine administration. Stimulation denoted by solid black bar under the pressure trace. B. Summarized results (N=6 cats) showing average bladder capacity normalized to saline control.

AA-induced irritation of the bladder significantly ($p<0.0001$) reduced bladder capacity to a mean of 23.6±7.1% (2.0±0.6 mL) of saline control capacity (8.0±1.1 mL) (FIG. 20, foot stimulation: 5 Hz, 0.2 ms, T=3-16 V.). Prior to tolterodine administration, foot stimulation significantly ($p<0.0001$) increased bladder capacity to 50.7±6.8% at 2 T and 79.0±11.6% at 4 T of saline control. After stimulation, bladder capacity returned to the pre-stimulation level (FIG. 20), indicating that there was no post-stimulation inhibition.

Dose Dependent Effect of Tolterodine Alone on Bladder Overactivity

During AA infusion CMGs, cumulative doses of tolterodine (0.003-0.3 mg/kg) increased bladder capacity dose dependently in the absence of foot stimulation (FIG. 21(A), the CMGs were performed in sequence from left to right in (A-C) and from top to bottom in each figure. Duration of foot stimulation is indicated by the black bar under the bladder pressure trace. Stimulation: 5 Hz, 0.2 ms, T=12 V. Infusion rate=1 ml/min). However, only the largest dose of tolterodine (0.3 mg/kg) significantly ($p<0.05$) increased the capacity (to 65.6±15.5% of the saline control capacity) (FIG. 22(A), stimulation: 5 Hz, 0.2 ms, T=3-16 V. Amplitude of micturition contraction is normalized to AA control prior to drug administration.).

Combined Effect of Tolterodine and Foot Stimulation on Bladder Overactivity

When tolterodine was combined with foot stimulation, the total inhibitory effect was additive. Bladder capacity was significantly ($p<0.05$) increased by both 2 T and 4 T foot stimulation when compared to AA control at every dosage (FIGS. 21 and 22(A)). After the 0.3 mg/kg dose of tolterodine which restored the small irritated bladder to a capacity of 65.6±15.5% of saline control, 2 T or 4 T foot stimulation significantly increased bladder capacity to 86.2±6.2% or 107.9±10.6%, respectively, of the saline control (FIG. 22(A)). A lower dose of tolterodine (0.1 mg/kg), which was not effective in significantly increasing control bladder capacity in the absence of stimulation, significantly ($p<0.05$) increased bladder capacity to 97.0±11.2% of saline control when combined with 4 T foot stimulation. Thus, combination therapy completely restored the irritated bladder to the capacity equivalent to the saline control (see the dashed line in FIG. 22(A)). After 2 T and 4 T stimulation, the bladder capacity returned to the pre-stimulation level at every dose of tolterodine, i.e. no post-stimulation effect was observed.

Figure 21:
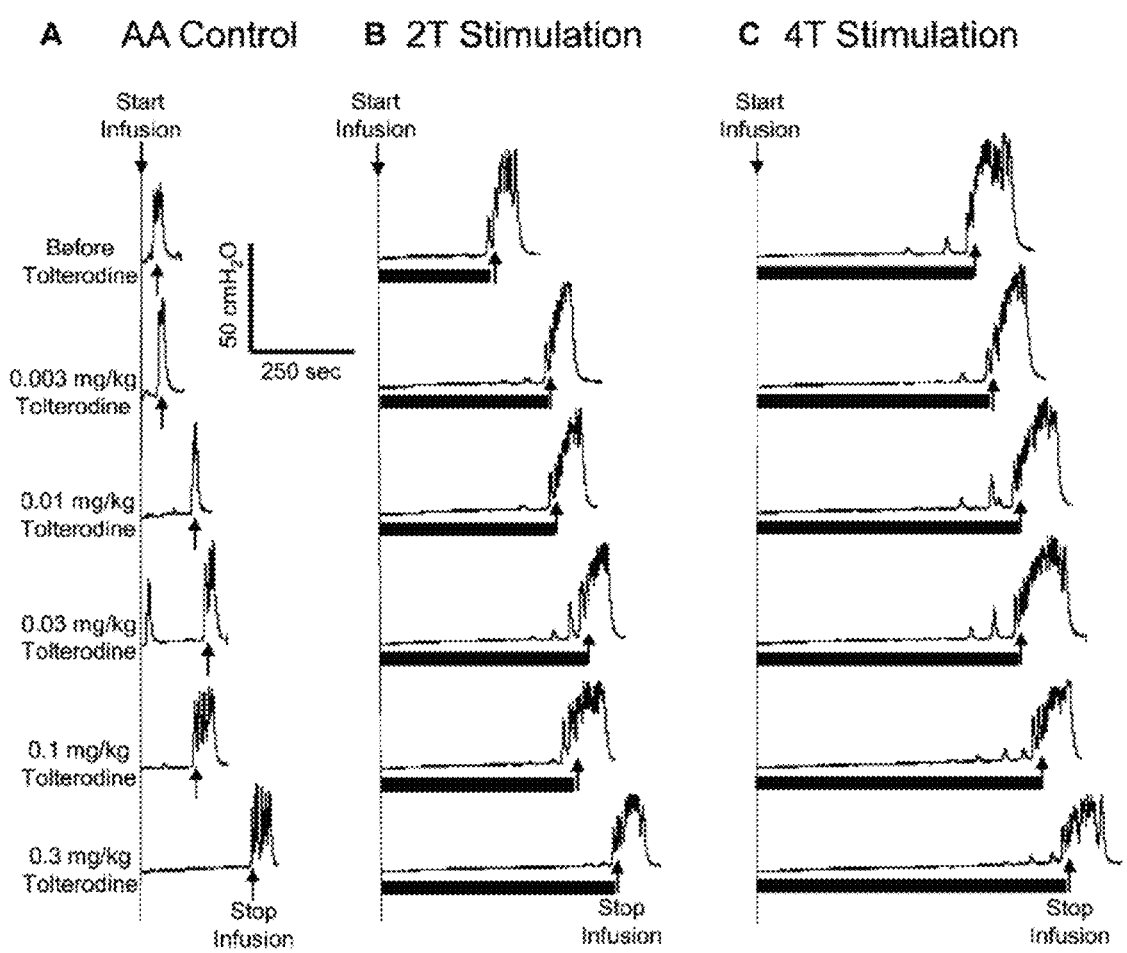
FIG. 21 shows dose-dependent effect of tolterodine and foot inhibition on bladder overactivity caused by AA irritation. A. Control CMGs without foot stimulation after increasing doses of tolterodine. B. CMGs during 2 T foot stimulation. C. CMGs during 4 T foot stimulation.
Figure 22:
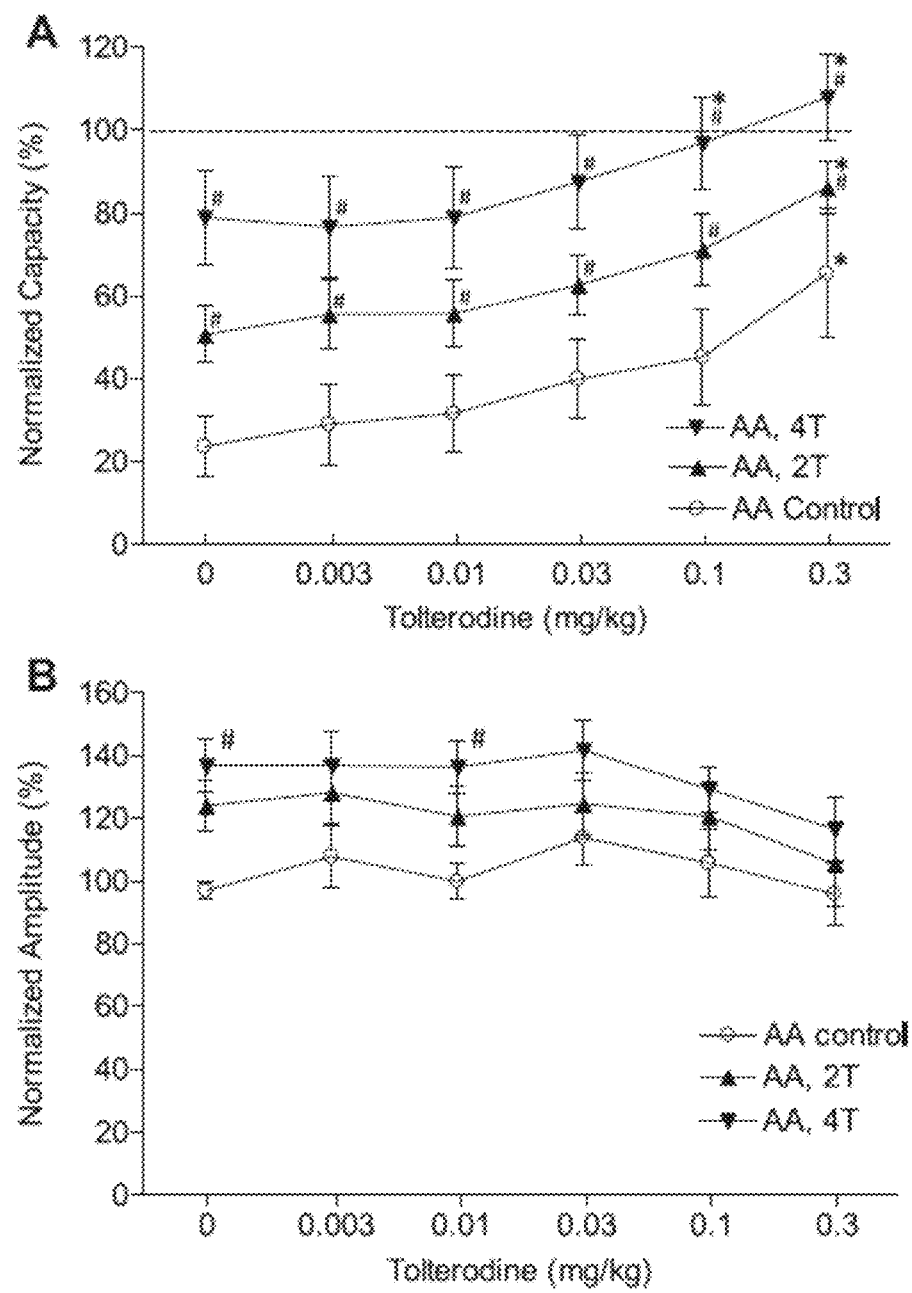
FIG. 22 shows summarized results of dose dependent effect of tolterodine and foot inhibition. A. Bladder overactivity caused by AA irritation. B. Amplitude of micturition contraction.

Tolterodine (0.003-0.3 mg/kg) did not alter the amplitude of bladder reflex contractions during control, 2 T or 4 T foot stimulation CMGs (FIGS. 21 and 22(B)). Foot stimulation at 4 T significantly ($p<0.05$) increased the contraction amplitude only at 0 mg/kg and 0.01 mg/kg tolterodine (FIG. 22(B)). The threshold pressure (5.0±1.3 cm $H_2O$) for inducing a micturition reflex was significantly ($p<0.05$) increased by foot stimulation (7.1±0.9 cm $H_2O$ at 2 T; 8.5±1.0 cm $H_2O$ at 4 T) and by tolterodine treatment (8.1±1.4 cm $H_2O$ at 0.3 mg/kg).

Example 4

Figure 23:
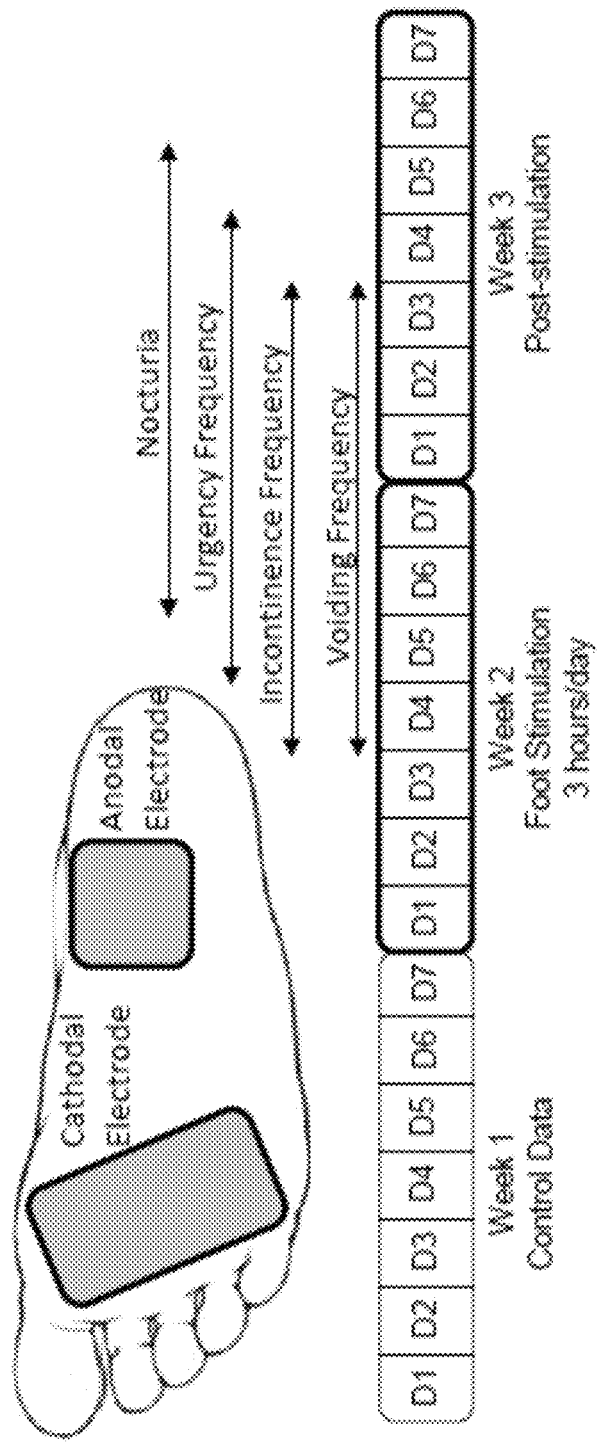
FIG. 23 shows foot stimulation schedule and electrode location in an experiment using a device as described herein.
Figure 24A:
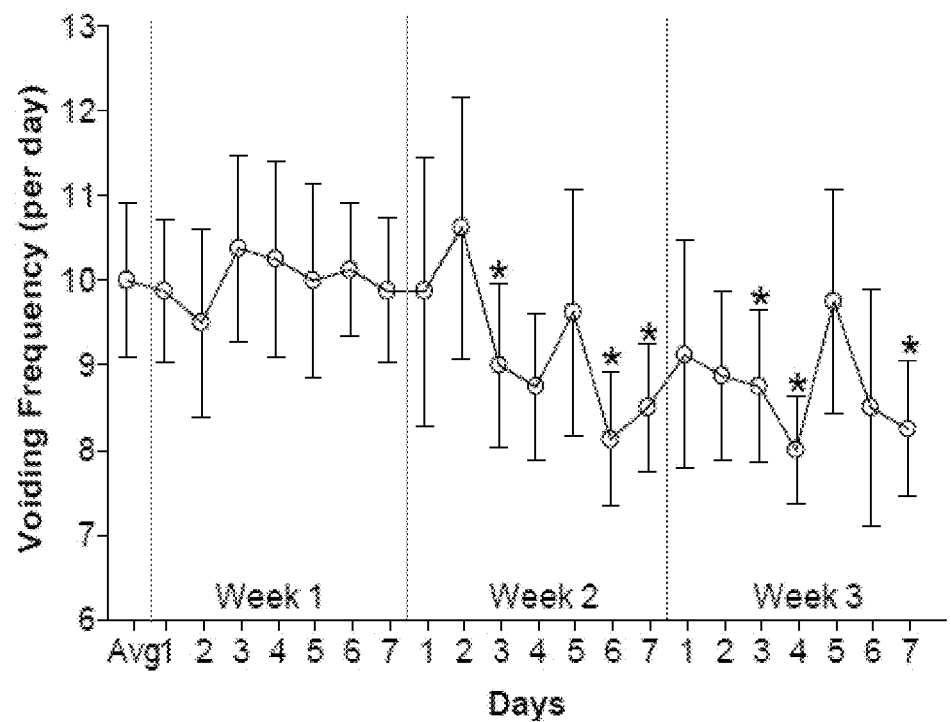
FIG. 24A-24B shows results of daily voiding from diaries in subjects undergoing foot stimulation as described herein. 24A (upper panel) Voiding frequency; 24A (lower panel) Urgency frequency; 24B (upper panel) Incontinence frequency; 24B (lower panel) Nocturia episodes.
Figure 24A:
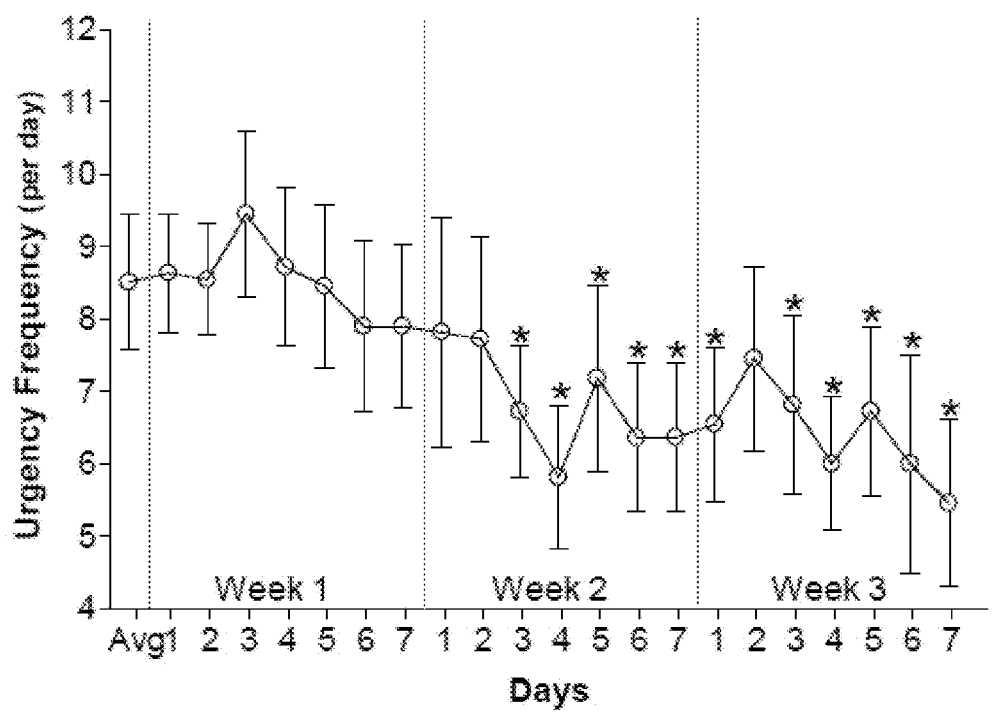
Figure 24B:
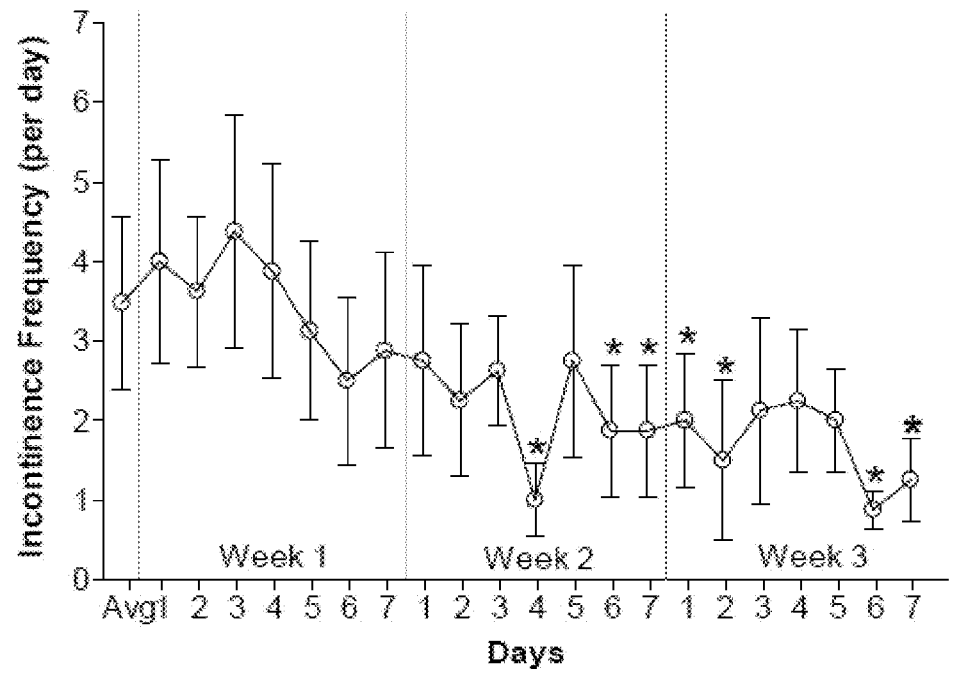
Figure 24B:
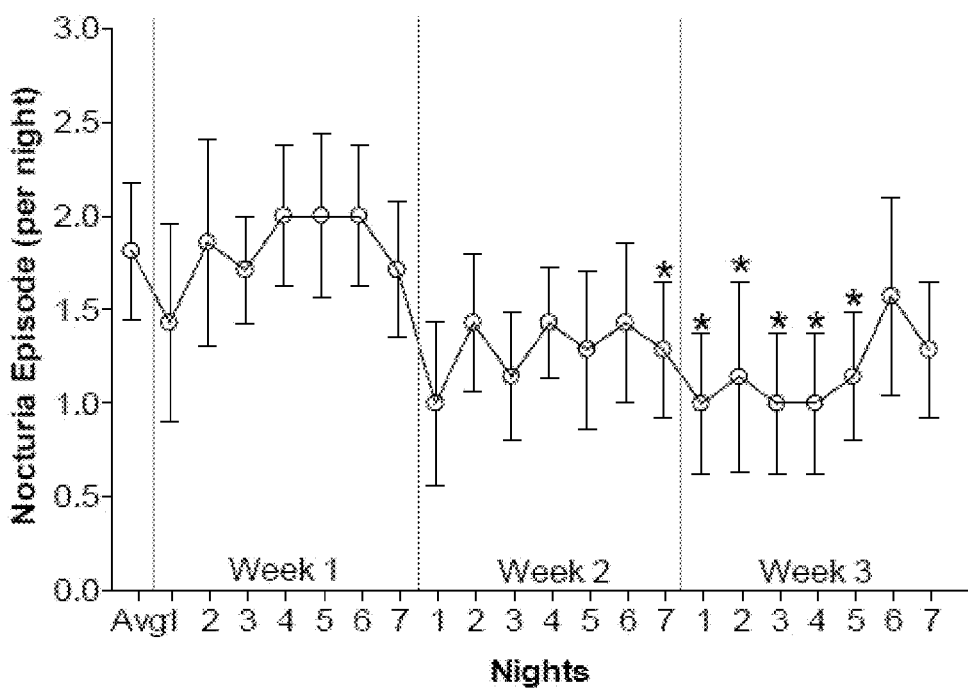

In this experiment, 20 adults with overactive bladder received foot neuromodulation with a device as described herein. The experiment was a three-week trial, as shown in FIG. 23. Specifically 20 adults were monitored for three weeks. No stimulation was applied during the first and third weeks (FIG. 23). During the second week of the trial, participants utilized a device as described herein, with electrode placement on the plantar surface of the foot as shown in FIG. 23. The acute effect of foot neuromodulation was determined during the second week, while the long-lasting post-stimulation effect was detected during the last week. During the second week, foot stimulation (5 Hz, 0.2 ms pulsewidth). The participants were asked to increase the stimulation intensity to as high of a level as possible without pain/discomfort. The stimulation was applied for three hours each day. As shown in FIG. 23, participants who showed a response to the treatment (N=16) maintained a urine diary, recording voiding frequency, incontinence frequency, urgency frequency, and episodes of nocturia (waking at night to urinate). These observations occurred for the periods illustrated in FIG. 23.

Figure 25:
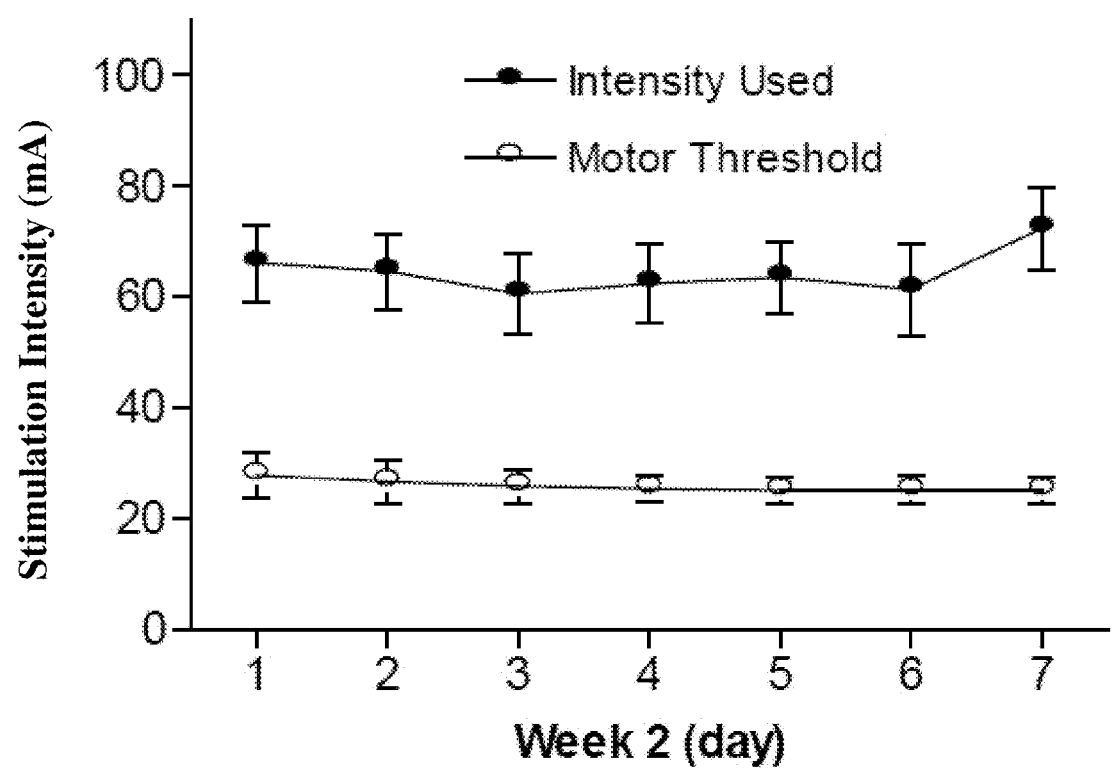
FIG. 25 shows average foot stimulation intensity used by subjects undergoing foot stimulation as described herein.

Results from this experiment are shown in FIGS. 24-26. FIG. 24 shows that participants reported significantly ($p<0.05$) less voiding (panel A), lower urgency frequency (B), lower incontinence frequency (C), and fewer episodes of nocturia per night (D) following initiation of foot neuromodulation. These results are provided in tabular form in FIG. 26, which further shows that stimulation resulted in larger volume (mL/void, p=0.0465), les strength per void (p=0.001), and lower severity per void (p=0.0006). When measuring incontinence severity, the scale is 0-3, with 0 being no severity, 1 and 2 being a little and moderate severity, and 3 being a large amount. Similarly, when measuring urgency strength, 0 is no strength, with 1 and 2 being mild and moderate strength and 3 being severe. FIG. 25 shows the average stimulation intensity for the participants during each of the days during the second week, when stimulation was applied. As can be seen, the average intensity was above 60 mA, or about 2.5 T (toe-twitch threshold), which was 26.2 mA in the cohort.

The results of this experiment show that foot neuromodulation, with simple stimulation for only three hours per day with a device as described herein, improve symptoms of overactive bladder in adults.

Example 5

In this experiment a device, system, and method as described herein was utilized to prevent bedwetting by foot neuromodulation, which stimulates the nerves in the foot during the day using skin surface electrodes to modulate bladder reflex activity during the night. Foot neuromodulation therapy eliminates the sleep disruptions associated with bedwetting alarms and many side effects associated with the drug treatments.

Figure 27:
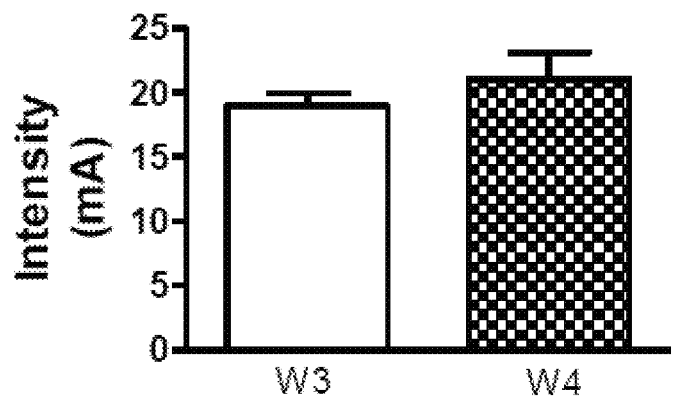
FIG. 27 shows stimulation frequency and electrode placement used by subjects undergoing foot stimulation as described herein.
Figure 27:
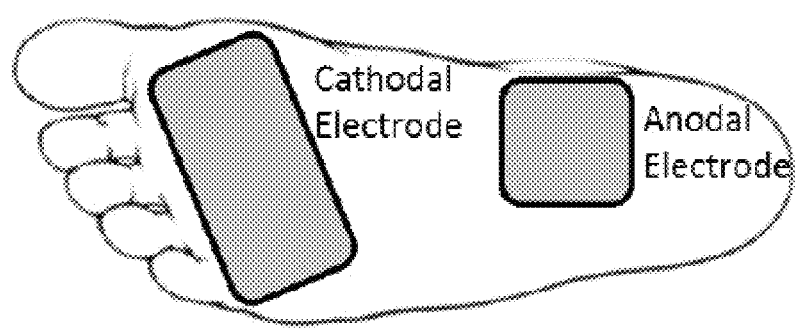

In this experiment, 20 children (mean age 11.2 years) underwent foot neuromodulation with a device as described herein (see, e.g., FIG. 13). The experiment was a six-week trial. Specifically, 20 children were monitored for six weeks. No stimulation was applied during weeks 1, 2, 5, and 6. During weeks 3 and 4 of the trial, participants utilized a device as described herein, with electrode placement on the plantar surface of the foot as shown in FIG. 27. The acute effect of foot neuromodulation was determined during the 3rd and 4th weeks, while the long-lasting post-stimulation effect was detected during the last 2 weeks. During these two weeks, foot stimulation (5 Hz, 0.2 ms pulse width). Average intensity of the stimulation is shown in FIG. 27. Participants were asked to increase the intensity to as high of a level as possible without discomfort. Stimulation was applied for one hour each day, at night before sleep. Participants were asked to increase the intensity (mA) of the stimulation to as high of a level as possible without causing discomfort, and were asked to record a night-time voiding log specifying the number of bedwetting nights the 6-week period.

Figure 28:
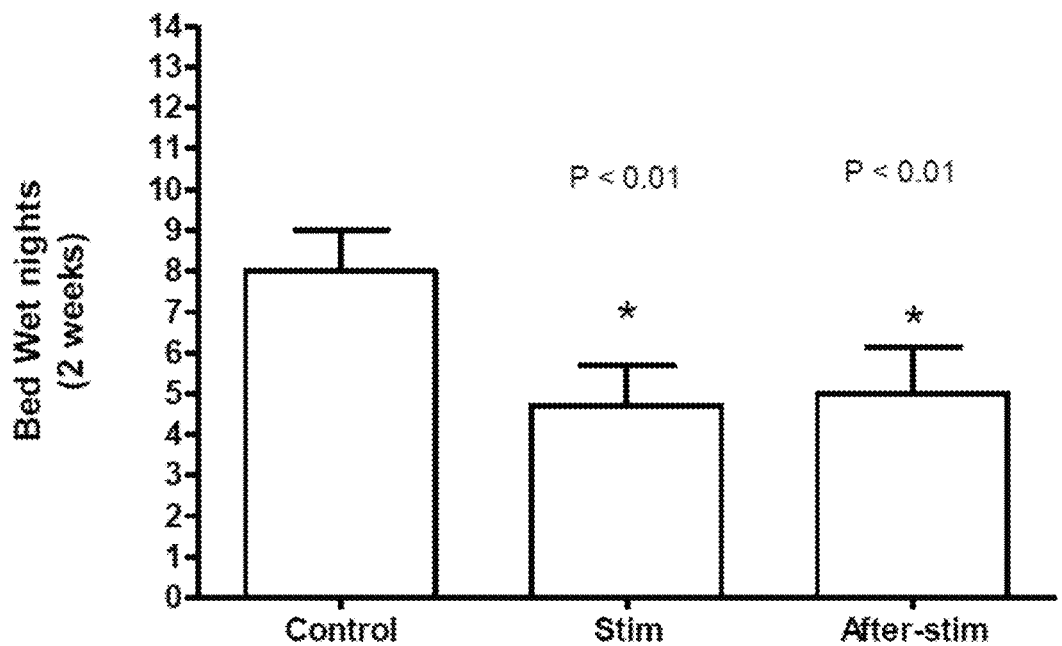
FIG. 28 shows results of nocturia in subjects undergoing foot stimulation as described herein.

Results from the experiment are shown in FIGS. 27 and 28. FIG. 27 shows average intensity (mA) for children during weeks 3 and 4. FIG. 28 shows the number of bedwetting nights in the initial two weeks (Control), during the two weeks when stimulation was applied (Stim), and during weeks 5 and 6, when no stimulation was applied (After-stim). As the graph shows, children who responded to the treatment (N=14) exhibited fewer bedwetting nights during stimulation (p<0.01) and after stimulation (p<0.01), suggesting a long-term effect of foot neuromodulation.

The results of the experiment show that foot neuromodulation is the first treatment that is effective for treatment of bedwetting. This treatment is accomplished without disrupting the sleep of the children and their parents, thereby reducing the stress for the family. Most importantly, it is safe without any side effects, and thus could completely change the current clinical practice in the treatment of bedwetting.

Example 6

The subjects are instructed to record daytime voided volumes during a 3-day period without any restriction on their daily food and water intake. They are also instructed to void in response to their usual bladder sensations and to note any void that was withheld or induced early due to unexpected situations. Those voiding volumes that resulted from unexpected situations are excluded from the study.

Foot stimulation is applied for 90 minutes in the morning (10:00 AM to 11:30 AM) on the second day while the subject is sitting. During the stimulation, the subject is asked to drink 1-2 bottles of water (500-1000 mL) so that a void could occur soon after stimulation. Two skin surface electrodes (LGMedSupply, Cherry Hill, NJ) are attached to the top surface of the foot. A large cathodal electrode (2 inch× 3.5 inch) is placed on the front of the foot to cover as much skin area as possible and a small anodal electrode (2 inch×2 inch) is placed between the first electrode and the talocrural joint (ankle) (similar to the arrangement of electrodes shown in FIG. 5). The electrodes are connected to a transcutaneous electrical nerve stimulator (LG-TEC ELITE, LGMedSupply, Cherry Hill, NJ) that provides constant current, rectangular pulses of 5 Hz frequency and 0.2 ms pulse width. The subject controls the stimulator to determine the minimal current needed to induce a toe twitch. The stimulation intensity is then increased to a maximal level (25-60 mA) comfortable to the subject for the entire 90 minute stimulation, which ranges between 2-6 times the minimal intensity necessary to induce a toe twitch (T).

The volume per void is averaged among the subjects over three time periods: 1) 24 hours prior to foot stimulation; 2) up to 5 hours after stimulation; and 3) up to 36 hours after stimulation. The second time period always includes the first void after the stimulation. However, if the voided volumes remain elevated in the following 1-2 voids, they are also included in the second time period. Therefore, the second time period is variable ranging up to 5 hours. The third time period includes voids up to 36 hours after stimulation, excluding the voids counted in the second time period. One-way ANOVA followed by Dunnett's multiple comparison is used to detect statistically (p<0.05) significant differences between voided volumes before and after stimulation.

Example 7

The subjects are instructed to record daytime voided volumes during a 3-day period without any restriction on their daily food and water intake. They are also instructed to void in response to their usual bladder sensations and to note any void that was withheld or induced early due to unexpected situations. Those voiding volumes that resulted from unexpected situations are excluded from the study.

Foot stimulation is applied for 90 minutes in the morning (10:00 AM to 11:30 AM) on the second day while the subject is sitting. During the stimulation, the subject is asked to drink 1-2 bottles of water (500-1000 mL) so that a void could occur soon after stimulation. Two skin surface electrodes (LGMedSupply, Cherry Hill, NJ) are attached to the bottom surface of the foot. A large cathodal electrode (2 inch×3.5 inch) is placed on the front of the foot to cover as much skin area as possible and a small anodal electrode (2 inch×2 inch) is placed between the first electrode and the talocrural joint (ankle) (similar to the arrangement of electrodes shown in FIG. 6). The electrodes are connected to a transcutaneous electrical nerve stimulator (LG-TEC ELITE, LGMedSupply, Cherry Hill, NJ) that provides constant current, rectangular pulses of 5 Hz frequency and 0.2 ms pulse width. The subject controls the stimulator to determine the minimal current needed to induce a toe twitch. The stimulation intensity is then increased to a maximal level (25-60 mA) comfortable to the subject for the entire 90 minute stimulation, which ranges between 2-6 times the minimal intensity necessary to induce a toe twitch (T).

The volume per void is averaged among the subjects over three time periods: 1) 24 hours prior to foot stimulation; 2) up to 5 hours after stimulation; and 3) up to 36 hours after stimulation. The second time period always includes the first void after the stimulation. However, if the voided volumes remain elevated in the following 1-2 voids, they are also included in the second time period. Therefore, the second time period is variable ranging up to 5 hours. The third time period includes voids up to 36 hours after stimulation, excluding the voids counted in the second time period. One-way ANOVA followed by Dunnett's multiple comparison is used to detect statistically ($p<0.05$) significant differences between voided volumes before and after stimulation.

Example 8

Experiments are performed in adult anesthetized cats. Each cat is anesthetized with isoflurane (2-3% in O2) during surgery and then changed to α-chloralose (65 mg/kg, supplemented as necessary) anesthesia during data collection. A pulse oximeter (9847V, Nonin Medical Inc., Plymouth, MN, USA) with the sensor attached to the tongue is used to monitor heart rate and blood oxygen saturation. Catheters are inserted in the right cephalic vein and right carotid artery for intravenous infusion of drugs and monitoring systemic blood pressure, respectively. Airway access is secured with a tracheostomy tube. Ureters are accessed through a midline abdominal incision and drained externally. The bladder is then cannulated with a double lumen catheter through a small cut at the proximal urethra to infuse saline or 0.25% AA and simultaneously measure bladder pressure. The proximal urethra is tied to prevent leakage. Fur is removed from the right hind foot and two self-adhesive pad electrodes (Grass FE10ND, Astro-Medical Inc., Mentor, OH, USA; diameter 1 cm) are attached to the skin at the top of the foot. One electrode is at the front of the foot and the other is between the first electrode and the talocrural joint.
Stimulation Protocol and Drug Administration Uniphasic rectangular pulses (5 Hz frequency, 0.2 ms pulsewidth) are delivered to the surface electrodes on the foot. Stimulation intensity threshold (T) is defined as the minimal intensity to induce a toe twitch. Foot stimulation of intensities 2-4 T are used in this study since previous studies demonstrated that this intensity range was effective in inhibiting reflex bladder contractions. Initially the bladder capacity is determined during cystometrograms (CMGs) by slowly infusing the bladder with saline. Multiple CMGs are performed to ensure reproducibility of the saline control capacity.

Bladder capacity is defined as the bladder volume threshold required to induce a micturition contraction of large amplitude (>30 cm $H_2O$) and long duration (>20 seconds). Then, repeated CMGs are performed with infusion of 0.25% AA to irritate the bladder, activate nociceptive bladder afferent C-fibers, and induce bladder overactivity. When the bladder capacity stabilizes, four CMGs are performed with AA infusion prior to the administration of duloxetine: (1) control without stimulation; (2) during 2 T stimulation; (3) during 4 T stimulation; and (4) control without stimulation to determine any post-stimulation effect. The bladder is emptied at the end of each CMG and a 3-5 minute rest period is inserted between CMGs.

After the pre-drug CMGs are performed, increasing cumulative doses (0.003, 0.01, 0.03, 0.1, 0.3, 1, and 3 mg/kg, i.v.) of duloxetine (Selleck Chemicals, Houston, TX) are given to determine the drug effect on bladder capacity. Ten minutes after administering each dose of duloxetine, the four CMGs are again performed with AA infusion under different conditions (control, 2 T stimulation, 4 T stimulation, and post-stimulation control). The four repeated CMGs are completed within 40-60 minutes.

Example 9

Experiments are performed in adult anesthetized cats. Each cat is anesthetized with isoflurane (2-3% in O2) during surgery and then changed to α-chloralose (65 mg/kg, supplemented as necessary) anesthesia during data collection. A pulse oximeter (9847V, Nonin Medical Inc., Plymouth, MN, USA) with the sensor attached to the tongue is used to monitor heart rate and blood oxygen saturation. Catheters are inserted in the right cephalic vein and right carotid artery for intravenous infusion of drugs and monitoring systemic blood pressure, respectively. Airway access is secured with a tracheostomy tube. Ureters are accessed through a midline abdominal incision and drained externally. The bladder is then cannulated with a double lumen catheter through a small cut at the proximal urethra to infuse saline or 0.25% AA and simultaneously measure bladder pressure. The proximal urethra is tied to prevent leakage. Two self-adhesive pad electrodes (Grass FE10ND, Astro-Medical Inc., Mentor, OH, USA; diameter 1 cm) are attached to the skin at the bottom of the foot. One electrode is at the front of the foot and the other is between the first electrode and the talocrural joint.
Stimulation Protocol and Drug Administration Uniphasic rectangular pulses (5 Hz frequency, 0.2 ms pulsewidth) are delivered to the surface electrodes on the foot. Stimulation intensity threshold (T) is defined as the minimal intensity to induce a toe twitch. Foot stimulation of intensities 2-4 T are used in this study since previous studies demonstrated that this intensity range was effective in inhibiting reflex bladder contractions. Initially the bladder capacity is determined during cystometrograms (CMGs) by slowly infusing the bladder with saline. Multiple CMGs are performed to ensure reproducibility of the saline control capacity.

Bladder capacity is defined as the bladder volume threshold required to induce a micturition contraction of large amplitude (>30 cm $H_2O$) and long duration (>20 seconds). Then, repeated CMGs are performed with infusion of 0.25% AA to irritate the bladder, activate nociceptive bladder afferent C-fibers, and induce bladder overactivity. When the bladder capacity stabilizes, four CMGs are performed with AA infusion prior to the administration of duloxetine: (1) control without stimulation; (2) during 2 T stimulation; (3) during 4 T stimulation; and (4) control without stimulation to determine any post-stimulation effect. The bladder is emptied at the end of each CMG and a 3-5 minute rest period is inserted between CMGs.

After the pre-drug CMGs are performed, increasing cumulative doses (0.003, 0.01, 0.03, 0.1, 0.3, 1, and 3 mg/kg, i.v.) of duloxetine (Selleck Chemicals, Houston, TX) are given to determine the drug effect on bladder capacity. Ten minutes after administering each dose of duloxetine, the four CMGs are again performed with AA infusion under different conditions (control, 2 T stimulation, 4 T stimulation, and post-stimulation control). The four repeated CMGs are completed within 40-60 minutes.
Data Analysis For each CMG, bladder capacity is normalized to the initial saline control capacity in the same animal, which allows for comparisons between animals. The bladder capacities are averaged for each condition and reported with standard error of the mean. Student T-test, one way ANOVA followed by Dunnett post-tests, or two-way ANOVA followed by Bonferroni posttests are used to determine the statistical significance ($p<0.05$).

Example 10

Experiments are conducted in adult cats under alpha-chloralose anesthesia (65 mg/kg, supplemented as necessary) after induction with isoflurane (2-3% in $O_2$). Heart rate and blood oxygen level are monitored with a pulse oximeter (9847 V, Nonin Medical Inc., Plymouth, MN, USA) that is attached to the tongue. Systemic blood pressure is monitored via a catheter in the right carotid artery. These physiological parameters are monitored to ensure that the animal's vital functions remain relatively stable during the entire experiment. Drugs or fluids are administered through a catheter in the right cephalic vein and airway access is secured with a tracheostomy tube. Ureters are accessed through a midline abdominal incision and drained externally. The bladder is cannulated through the urethra with a double lumen catheter to infuse (1-2 ml/min) saline or 0.25% AA via one lumen and measure bladder pressure via another lumen. A ligature is tied around the proximal urethra to prevent leakage. Fur is removed from the foot and two self-adhesive pad electrode (Grass FE10ND, Astro-Medical Inc., Mentor, OH, USA; diameter 1 cm) are attached to the skin at the top of the left hind foot. One electrode was at the front of the foot and the other was at the hindfoot, near the talocrural (ankle) joint.

Stimulation Protocol and Drug Administration

Uniphasic rectangular pulses (5 Hz frequency, 0.2 ms pulsewidth) are delivered to the skin electrodes on the foot. Threshold (T) stimulation intensity (3-16 V), which is defined as the minimal intensity to induce an observable toe twitch, is determined by slowly increasing the stimulation intensity at the beginning of the experiment. Previous studies indicated that foot stimulation at 2 T is required to inhibit reflex bladder contractions. Therefore, intensities of 2 T and 4 T are used to suppress bladder overactivity induced by AA irritation. The initial bladder capacity is determined during a cystometrogram (CMG) by slowly infusing the bladder with saline. Bladder capacity is defined as the bladder volume threshold to induce a bladder reflex contraction of large amplitude (>30 cm $H_2O$) and long duration (>20 seconds).

Multiple CMGs are performed to determine reproducibility of the saline control capacity. Then, repeated CMGs are performed with AA infusion to irritate the bladder, activate nociceptive bladder C-fiber afferents, and induce bladder overactivity. Once the irritated bladder capacity is stabilized, four CMGs are performed prior to drug administration: 1. control CMG without stimulation; 2. CMG during 2 T stimulation; 3. CMG during 4 T stimulation; and 4. control CMG without stimulation to determine any post-stimulation effect. Increasing cumulative doses of tolterodine (tolterodine L-tartrate, Tocris Bioscience, Bristol, UK) are then administered (0.003, 0.01, 0.03, 0.1, and 0.3 mg/kg, i.v.). Ten minutes after administering each dose of tolterodine, the CMGs are performed again under the four different conditions (control, 2 T stimulation, 4 T stimulation, and post-stimulation control) to determine the drug effect on bladder capacity. The bladder is emptied after each CMG followed by a 3-5 min rest period to allow the distended detrusor to recover.

Data Analysis

For the repeated CMG recordings, bladder capacity is normalized to the initial saline control capacity in the same animal to allow comparisons between animals. Capacity measurements under the same conditions are averaged and reported as mean±standard error of the mean (SEM). The mean amplitude of the bladder reflex contraction is also measured during each CMG and normalized to the AA control CMG to determine the effect of tolterodine on detrusor contractility. Statistical significance (p<0.05) is detected by ANOVA followed by Dunnett or Bonferroni post-tests.

Example 11

Experiments are conducted in adult cats under achloralose anesthesia (65 mg/kg, supplemented as necessary) after induction with isoflurane (2-3% in $O_2$). Heart rate and blood oxygen level are monitored with a pulse oximeter (9847 V, Nonin Medical Inc., Plymouth, MN, USA) that is attached to the tongue. Systemic blood pressure is monitored via a catheter in the right carotid artery. These physiological parameters are monitored to ensure that the animal's vital functions remain relatively stable during the entire experiment. Drugs or fluids are administered through a catheter in the right cephalic vein and airway access is secured with a tracheostomy tube. Ureters are accessed through a midline abdominal incision and drained externally. The bladder is cannulated through the urethra with a double lumen catheter to infuse (1-2 ml/min) saline or 0.25% AA via one lumen and measure bladder pressure via another lumen. A ligature is tied around the proximal urethra to prevent leakage. Two self-adhesive pad electrode (Grass FE10ND, Astro-Medical Inc., Mentor, OH, USA; diameter 1 cm) are attached to the skin at the bottom of the left hind foot. One electrode was at the front of the foot and the other was at the hindfoot, near the talocrural (ankle) joint.

Stimulation Protocol and Drug Administration

Uniphasic rectangular pulses (5 Hz frequency, 0.2 ms pulsewidth) are delivered to the skin electrodes on the foot. Threshold (T) stimulation intensity (3-16 V), which is defined as the minimal intensity to induce an observable toe twitch, is determined by slowly increasing the stimulation intensity at the beginning of the experiment. Previous studies indicated that foot stimulation at 2 T is required to inhibit reflex bladder contractions. Therefore, intensities of 2 T and 4 T are used to suppress bladder overactivity induced by AA irritation. The initial bladder capacity is determined during a cystometrogram (CMG) by slowly infusing the bladder with saline. Bladder capacity is defined as the bladder volume threshold to induce a bladder reflex contraction of large amplitude (>30 cm $H_2O$) and long duration (>20 seconds).

Multiple CMGs are performed to determine reproducibility of the saline control capacity. Then, repeated CMGs are performed with AA infusion to irritate the bladder, activate nociceptive bladder C-fiber afferents, and induce bladder overactivity. Once the irritated bladder capacity is stabilized, four CMGs are performed prior to drug administration: 1. control CMG without stimulation; 2. CMG during 2 T stimulation; 3. CMG during 4 T stimulation; and 4. control CMG without stimulation to determine any post-stimulation effect. Increasing cumulative doses of tolterodine (tolterodine L-tartrate, Tocris Bioscience, Bristol, UK) are then administered (0.003, 0.01, 0.03, 0.1, and 0.3 mg/kg, i.v.). Ten minutes after administering each dose of tolterodine, the CMGs are performed again under the four different conditions (control, 2 T stimulation, 4 T stimulation, and post-stimulation control) to determine the drug effect on bladder capacity. The bladder is emptied after each CMG followed by a 3-5 min rest period to allow the distended detrusor to recover.

Data Analysis

For the repeated CMG recordings, bladder capacity is normalized to the initial saline control capacity in the same animal to allow comparisons between animals. Capacity measurements under the same conditions are averaged and reported as mean±standard error of the mean (SEM). The mean amplitude of the bladder reflex contraction is also measured during each CMG and normalized to the AA control CMG to determine the effect of tolterodine on detrusor contractility. Statistical significance (p<0.05) is detected by ANOVA followed by Dunnett or Bonferroni post-tests.

The invention can be further characterized in the following numbered clauses.

Clause 1: An electrode-containing device comprising: a base adapted to cover a portion of a plantar surface of a human foot including a portion of the forefoot overlaying a plurality of branches of the medial or lateral plantar nerves and a portion of the hindfoot overlaying the medial and lateral plantar nerves; a first electrode attached to the base at a position adapted to the hindfoot to contact skin overlaying the medial and lateral plantar nerves; a second electrode attached to the base at a position adapted to the forefoot to contact skin overlaying a plurality of branches of the medial or lateral plantar nerves in the forefoot; and a first and second electrical lead attached to the first and second electrodes, respectively.

Clause 2: The electrode-containing device of clause 1, in which the first electrode is a cathode and the second electrode is an anode.

Clause 3: The electrode-containing device of clause 1, in which the first electrode is an anode and the second electrode is a cathode.

Clause 4: The electrode-containing device of any of clauses 1-3, in which the second electrode overlays at least 50% of the width of the sole at the forefoot.

Clause 5: The electrode-containing device of any of clauses 1-4, in which the second electrode overlays at least a portion of the metatarsophalangeal joint.

Clause 6: The electrode-containing device of any of clauses 1-5, in which the first electrode overlays at least a portion of the calcaneus bone.

Clause 7: The electrode-containing device of any of clauses 1-6, in which the second electrode overlays a predominance of branches of the medial and lateral plantar nerves in the forefoot.

Clause 8: The electrode-containing device of any of clauses 1-7, wherein the base has a perimeter having the shape of a sole of a foot, and optionally is an orthotic insert.

Clause 9: The electrode-containing device of any of clauses 1-8, wherein the base is a thin polymeric film having an adhesive on a side comprising the electrodes and facing the foot.

Clause 10: The electrode-containing device of any of clauses 1-9, further comprising one or more connectors for an external pulse generator attached to the leads.

Clause 11: The electrode-containing device of any of clauses 1-10, further comprising an adhesive on a surface of the base and/or electrodes for removably securing the device to a patient's foot.

Clause 12: The electrode-containing device of any of clauses 1-11, wherein the base is shaped substantially like a plantar surface or sole of a human foot.

Clause 13: An electrical nerve stimulation system comprising: an electrode-containing device of any of clauses 1-12; a pulse generator external to the electrode-containing device and connected to the leads, configured to generate pulses of pulsewidth 0.01-3 ms between 1-100 V and 1-100 mA, at frequency 1-50 Hz.

Clause 14: The system of clause 13, in which the pulse generator comprises an adjustment mechanism for adjusting one or more parameters of the pulses.

Clause 15: The system of clause 13 or 14, in which the adjustment mechanism comprise a wireless receiver in wireless communication with a wireless controller.

Clause 16: The system of any of clauses 13-15, wherein the pulse generator produces monophasic, rectangular pulses or biphasic pulses.

Clause 17: The system of any of clauses 13-16, wherein the pulse generator provides pulses having a pulsewidth of 0.2 ms at 5 Hz, and wherein the intensity of the pulses is from 2-6 times a toe twitch threshold of a patient.

Clause 18: The system of any of clauses 13-17, wherein the pulse generator provides a fixed output of pulses of pulsewidth 0.01-3 ms between 1-100 V and 1-80 mA, at frequency 1-50 Hz.

Clause 19: A method of treating urological or gastrointestinal disorders comprising: applying an electrode-containing device of any of clauses 1-12 to a foot of a patient in need of such treatment, wherein the electrode-containing device is attached to a pulse generator external to the electrode-containing device comprising a connector for connecting the pulse generator to the device; and stimulating the patient's foot with the device with pulses of pulsewidth 0.01-3 ms between 1-100 V and 1-100 mA, at frequency 1-50 Hz, thereby stimulating the lateral and medial plantar nerves of the patient.

Clause 20: The method of clause 19, in which the urological or gastrointestinal disorder is one or more of: overactive bladder (OAB) symptoms including bladder overactivity, urinary frequency, urinary urgency, urinary incontinence; interstitial cystitis (IC); urinary retention; pelvic pain; fecal incontinence; irritable bowel syndrome (IBS); and constipation.

Clause 21: The method of clause 19 or 20, in which the urological or gastrointestinal disorder is urinary incontinence.

Clause 22: The method of any of clauses 19-21, in which the urinary incontinence is bedwetting, and, optionally, with pulses of a frequency of 5 Hz, 0.2 ms pulsewidth, and/or from greater than 0 mA to 80 mA.

Clause 23: The method of any of clauses 19-22, wherein the pulse generator provides pulses having a pulsewidth of 0.2 ms at 5 Hz, and wherein the intensity of the pulses is from 2-6 times a toe twitch threshold of a patient.

Clause 24: The method of any of clauses 19-23, wherein the patient's foot is stimulated for from 1 to 360 minutes.

Clause 25: The method of any of clauses 19-24, wherein the patient's foot is stimulated for at least 30 minutes.

Clause 26: The method of any of clauses 19-25, wherein the patient's foot is stimulated for at least 180 minutes.

Clause 27: The method of any of clauses 19-26, further comprising administering an anti-muscarinic compound to the patient.

Clause 28: The method of clause 27, wherein the anti-muscarinic compound is selected from the group consisting of atropine, benztropine, biperiden, ipratropium, oxitropium, tiotropium, glycopyrrolate, oxybutynin, tolterodine, chlorpheniramine, diphenhydramine, dimenhydrinate, orphenadrine, trihexyphenidyl, and dicyclomine.

Clause 29: The method of clause 27 or 28, wherein the anti-muscarinic compound is tolterodine.

Clause 30: The method of any of clauses 27-29, wherein the anti-muscarinic compound is administered at between 0.003 and 1 mg/kg.

Clause 31: The method of any of clauses 27-30, wherein the anti-muscarinic compound is administered orally or parenterally.

Clause 32: The method of any of clauses 19-31, further comprising administering to a patient in need thereof a serotonin reuptake inhibitor and/or a serotonin receptor antagonist.

Clause 33: The method of clause 32, wherein the serotonin reuptake inhibitor is selected from the group consisting of alaproclate, citalopram, dapoxetine, escitalopram, femoxetine, fluoxetine, fluvoxamine, ifoxetine, indalpine, omiloxetine, panuramine, paroxetine, pirandamine, duloxetine, dapoxetine, sertraline, and zimelidine and the serotonin receptor antagonist is selected from the group consisting of alprenolol, AV-965, BMY-7,378, cyanopindolol, dotarizine, flopropione, GR-46,611, isodocyanopindolol, isamoltane, lecozotan, methiothepin, methysergide, MPPF, NAN-190, oxprenolol, pindobind, pindolol, propranolol, risperidone, robalzotan, SB-649,915 (which acts as both a reuptake inhibitor and a receptor antagonist), SDZ-216,525, spiperone, spiramide, spiroxatrine, UH-301, WAY100135, WAY 100635, and xylamidine.

Clause 34: The method of clause 32 or 33, wherein the serotonin reuptake inhibitor is duloxetine.

Clause 35: The method of any of clauses 32-34, wherein the serotonin receptor antagonist is WAY100635.

Clause 36: The method of any of clauses 32-35, comprising administering both a serotonin reuptake inhibitor and a serotonin receptor antagonist.

Clause 37: The method of any of clauses 32-36, in which the serotonin reuptake inhibitor is duloxetine and the serotonin receptor antagonist is WAY100635.

Clause 38: The method of any of clauses 32-37, wherein the serotonin reuptake inhibitor is administered at between 0.003 and 5 mg/kg and the serotonin receptor antagonist is administered at between 0.1 and 1 mg/kg.

Clause 39: The method of any of clauses 32-38, wherein the serotonin reuptake inhibitor or the serotonin receptor antagonist are administered orally of parenterally.

Clause 40: The method of any of clauses 19-39, further comprising administering an opioid drug to the patient.

Clause 41: The method of clause 40, wherein the opioid drug is selected from the group consisting of morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine, buprenorphine, fentanyl, pethidine, levorphanol, methadone, tramadol, dextropropoxyphene, tapentadol, endorphins, enkephalins, dynorphins, and endomorphins.

Clause 42: The method of clause 40 or 41, wherein the opioid drug is tramadol.

Clause 43: The method of any of clauses 40-42, wherein the opioid drug is administered at between 0.003 and 1 mg/kg.

Clause 44: The method of any of clauses 40-43, wherein the opioid drug is administered orally or parenterally.

Clause 45: A method of manufacturing an electrode-containing device comprising: forming a base adapted to cover a portion of a bottom surface of a human foot including a portion of the forefoot overlaying a plurality of branches of the medial or lateral plantar nerves and a portion of the hindfoot overlaying the medial and lateral plantar nerves; attaching a first electrode to the base at a position in the base adapted to contact skin overlaying the medial and lateral plantar nerves; attaching a second electrode to the base at a position in the base adapted to contact skin overlaying a plurality of branches of the medial or lateral plantar nerves in the forefoot; and attaching electrode leads for the first and second electrodes to the base.

Clause 46: The method of clause 45, wherein the second electrode is adapted to engage skin of the sole of the foot over at least 50% of the width of the forefoot.

Clause 47: The method of clause 45 or 46, in which a plurality of the devices are manufactured to accommodate a plurality of standardized foot sizes.

Clause 48: The method of any of clauses 45-47, in which the electrodes are embedded within the base.

Clause 49: The method of any of clauses 45-48, in which the base is configured to have a perimeter having the shape of a sole of a foot, and optionally is an orthotic insert.

Clause 50: The method of any of clauses 45-49, wherein electrode leads are embedded within the base.

Clause 51. An electrode-containing device comprising: a base adapted to cover a portion of a dorsal surface of a human foot including a portion of the forefoot overlaying a plurality of branches of the dorsal intermediate and medial cutaneous nerves, deep peroneal nerve, sural nerve, and/or saphenous nerve, and a portion of the hindfoot overlaying the superficial peroneal nerve, deep peroneal nerve, and/or saphenous nerve; a first electrode attached to the base at a position adapted to a dorsal portion of the hindfoot to contact skin overlaying the superficial peroneal nerve, deep peroneal nerve, and/or saphenous nerve; a second electrode attached to the base at a position adapted to a dorsal portion of the forefoot to contact skin overlaying a plurality of branches of the dorsal intermediate and medial cutaneous nerves, deep peroneal nerve, sural nerve, and/or saphenous nerve in the forefoot; and a first and second electrical lead attached to the first and second electrodes, respectively.

Clause 52: The electrode-containing device of clause 51, in which the first electrode is a cathode and the second electrode is an anode.

Clause 53: The electrode-containing device of clause 51, in which the first electrode is an anode and the second electrode is a cathode.

Clause 54: The electrode-containing device of any of clauses 51-53, in which the second electrode overlays at least 50% of the width of the foot at the forefoot.

Clause 55: The electrode-containing device of any of clauses 51-54, in which the second electrode overlays at least a portion of the metatarsophalangeal joint.

Clause 56: The electrode-containing device of any of clauses 51-55, in which the first electrode overlays at least a portion of the calcaneus bone.

Clause 57: The electrode-containing device of any of clauses 51-56, in which the second electrode overlays a predominance of branches of the dorsal intermediate and medial cutaneous nerves, deep peroneal nerve, sural nerve, and/or saphenous nerve in the forefoot.

Clause 58: The electrode-containing device of any of clauses 51-57, wherein the base has a perimeter having the shape of the dorsal area of a foot from the proximal phalanges to the talocrural joint.

Clause 59: The electrode-containing device of any of clauses 51-58, wherein the base is a thin polymeric film having an adhesive on a side comprising the electrodes and facing the foot.

Clause: 60: The electrode-containing device of any of clauses 51-59, further comprising one or more connectors for an external pulse generator attached to the leads.

Clause 61: The electrode-containing device of any of clauses 51-60 further comprising an adhesive on a surface of the base and/or electrodes for removably securing the device to a patient's foot.

Clause 62: The electrode-containing device of any of clauses 51-61, wherein the base is shaped substantially to interact with the dorsal surface of a human foot.

Clause 63: An electrical nerve stimulation system comprising: an electrode-containing device of any of clauses 51-62; a pulse generator external to the electrode-containing device and connected to the leads, configured to generate pulses of between 1-100 V and 1-100 mA, having a pulsewidth of 0.01-3 ms, at frequency 1-50 Hz.

Clause 64: The system of clause 63, in which the pulse generator comprises an adjustment mechanism for adjusting one or more parameters of the pulses.

Clause 65: The system of clause 63 or 64, in which the adjustment mechanism comprise a wireless receiver in wireless communication with a wireless controller.

Clause 66: The system of any of clauses 63-65, wherein the pulse generator produces monophasic, rectangular pulses or biphasic pulses.

Clause 67: The system of any of clauses 63-66, wherein the pulse generator provides pulses having a pulsewidth of 0.01-3 ms at 1-50 Hz, and wherein the intensity of the pulses is from 2-6 times a toe twitch threshold of a patient.

Clause 68: The system of any of clauses 63-67, wherein the pulse generator provides a fixed output of pulses of 1-100 V and 1-80 mA, having a pulsewidth of 0.01-3 ms, at frequency 1-50 Hz.

Clause 69: A method of treating urological or gastrointestinal disorders comprising: applying an electrode-containing device of any of clauses 51-62 to a foot of a patient in need of such treatment, wherein the electrode-containing device is attached to a pulse generator external to the electrode-containing device comprising a connector for connecting the pulse generator to the device; and stimulating the patient's foot with the device with pulses of between 1-100 V and 1-100 mA, having a pulsewidth of 0.01-3 ms, at from 1-50 Hz, thereby stimulating the dorsal intermediate and medial cutaneous nerves, deep peroneal nerve, sural nerve, and/or saphenous nerve of the patient.

Clause 70: The method of clause 69, in which the urological or gastrointestinal disorder is one or more of: overactive bladder (OAB) symptoms including bladder overactivity; urinary frequency; urinary urgency, urinary incontinence; interstitial cystitis (IC), urinary retention; pelvic pain; fecal incontinence; irritable bowel syndrome (IBS); and constipation.

Clause 71: The method of clause 69 or 70, wherein the pulse generator provides pulses having a pulsewidth of 0.01-3 ms at 1-50 Hz, and wherein the intensity of the pulses is from 2-6 times a toe twitch threshold of a patient.

Clause 72: The method of any of clauses 69-71, wherein the patient's foot is stimulated for from 1 to 360 minutes.

Clause 73: The method of any of clauses 69-72, wherein the patient's foot is stimulated for at least 30 minutes.

Clause 74: The method of any of clauses 69-73, wherein the patient's foot is stimulated for at least 90 minutes.

Clause 75: The method of any of clauses 69-74, further comprising administering an anti-muscarinic compound to the patient.

Clause 76: The method of clause 75, wherein the anti-muscarinic compound is selected from the group consisting of atropine, benztropine, biperiden, ipratropium, oxitropium, tiotropium, glycopyrrolate, oxybutynin, tolterodine, chlorpheniramine, diphenhydramine, dimenhydrinate, orphenadrine, trihexyphenidyl, and dicyclomine.

Clause 77: The method of clause 75 or 76, wherein the anti-muscarinic compound is tolterodine.

Clause 78: The method of any of clauses 75-77, wherein the anti-muscarinic compound is administered at between 0.003 and 1 mg/kg.

Clause 79: The method of any of clauses 75-78, wherein the anti-muscarinic compound is administered orally or parenterally.

Clause 80: The method of any of clauses 69-79, further comprising administering to a patient in need thereof a serotonin reuptake inhibitor and/or a serotonin receptor antagonist.

Clause 81: The method of clause 80, wherein the serotonin reuptake inhibitor is selected from the group consisting of alaproclate, citalopram, dapoxetine, escitalopram, femoxetine, fluoxetine, fluvoxamine, ifoxetine, indalpine, omiloxetine, panuramine, paroxetine, pirandamine, duloxetine, dapoxetine, sertraline, and zimelidine and the serotonin receptor antagonist is selected from the group consisting of alprenolol, AV-965, BMY-7,378, cyanopindolol, dotarizine, flopropione, GR-46,611, isodocyanopindolol, isamoltane, lecozotan, methiothepin, methysergide, MPPF, NAN-190, oxprenolol, pindobind, pindolol, propranolol, risperidone, robalzotan, SB-649,915 (which acts as both a reuptake inhibitor and a receptor antagonist), SDZ-216,525, spiperone, spiramide, spiroxatrine, UH-301, WAY100135, WAY 100635, and xylamidine.

Clause 82: The method of clause 80 or 81, wherein the serotonin reuptake inhibitor is duloxetine.

Clause 83: The method of any of clauses 80-82, wherein the serotonin receptor antagonist is WAY100635.

Clause 84: The method of any of clauses 80-83, comprising administering both a serotonin reuptake inhibitor and a serotonin receptor antagonist.

Clause 85: The method of any of clauses 80-84, in which the serotonin reuptake inhibitor is duloxetine and the serotonin receptor antagonist is WAY100635.

Clause 86: The method of any of clauses 80-85, wherein the serotonin reuptake inhibitor is administered at between 0.003 and 5 mg/kg and the serotonin receptor antagonist is administered at between 0.1 and 1 mg/kg.

Clause 87: The method of any of clauses 80-86, wherein the serotonin reuptake inhibitor or the serotonin receptor antagonist are administered orally of parenterally.

Clause 88: The method of any of clauses 69-87, further comprising administering an opioid drug to the patient.

Clause 89: The method of clause 88, wherein the opioid drug is selected from the group consisting of morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine, buprenorphine, fentanyl, pethidine, levorphanol, methadone, tramadol, dextropropoxyphene, tapentadol, endorphins, enkephalins, dynorphins, and endomorphins.

Clause 90: The method of clause 88 or 89, wherein the opioid drug is tramadol.

Clause 91: The method of any of clauses 88-90 wherein the opioid drug is administered at between 0.003 and 1 mg/kg.

Clause 92: The method of any of clauses 88-91, wherein the opioid drug is administered orally or parenterally.

Clause 93: A method of manufacturing an electrode-containing device comprising: forming a base adapted to cover a portion of a dorsal surface of a human foot including a portion of the forefoot overlaying a plurality of branches of the dorsal intermediate and medial cutaneous nerves, deep peroneal nerve, sural nerve, and/or saphenous nerve, and a portion of the hindfoot overlaying the superficial peroneal nerve, deep peroneal nerve, and/or saphenous nerve; attaching a first electrode to the base at a position in the base adapted to contact skin overlaying the superficial peroneal nerve, deep peroneal nerve, and/or saphenous nerve; attaching a second electrode to the base at a position in the base adapted to contact skin overlaying a plurality of branches of the dorsal intermediate and medial cutaneous nerves, deep peroneal nerve, sural nerve, and/or saphenous nerve in the forefoot; and attaching electrode leads for the first and second electrodes to the base.

Clause 94: The method of clause 93, wherein the second electrode is adapted to engage skin of the dorsal surface of the foot over at least 50% of the width of the forefoot.

Clause 95: The method of clause 93 or 94, in which a plurality of the devices are manufactured to accommodate a plurality of standardized foot sizes.

Clause 96: The method of any of clauses 93-95, in which the electrodes are embedded within the base.

Clause 97: The method of any of clauses 93-96, in which the base is configured to have a perimeter having the shape of the dorsal area of a foot from the proximal phalanges to the talocrural joint.

Clause 98: The method of any of clauses 93-97, wherein electrode leads are embedded within the base.

Clause 99: Use of an electrode-containing device comprising a base adapted to cover a portion of a dorsal surface of a human foot including a portion of the forefoot overlaying a plurality of branches of the dorsal intermediate and medial cutaneous nerves, deep peroneal nerve, sural nerve, and/or saphenous nerve, and a portion of the hindfoot overlaying the superficial peroneal nerve, deep peroneal nerve, and/or saphenous nerve; a first electrode attached to the base at a position adapted to a dorsal portion of the hindfoot to contact skin overlaying the superficial peroneal nerve, deep peroneal nerve, and/or saphenous nerve; a second electrode attached to the base at a position adapted to a dorsal portion of the forefoot to contact skin overlaying a plurality of branches of the dorsal intermediate and medial cutaneous nerves, deep peroneal nerve, sural nerve, and/or saphenous nerve in the forefoot; and a first and second electrical lead attached to the first and second electrodes, respectively, for treatment of urinary incontinence, comprising: applying the electrode-containing device to a dorsal surface of a foot of a patient in need of such treatment, wherein the electrode-containing device is attached to a pulse generator external to the electrode-containing device comprising a connector for connecting the pulse generator to the device; and stimulating the patient's foot with the device with pulses of between 1-100 V, preferably about 60 V, and 1-100 mA, having a pulsewidth of 0.01-3 ms, at from 1-50 Hz, preferably about 5 Hz, thereby stimulating the dorsal intermediate and medial cutaneous nerves, deep peroneal nerve, sural nerve, and/or saphenous nerve of the patient.

Clause 100: Use of an electrode-containing device comprising: a base adapted to cover a portion of a plantar surface of a human foot including a portion of the forefoot overlaying a plurality of branches of the medial or lateral plantar nerves and a portion of the hindfoot overlaying the medial and lateral plantar nerves; a first electrode attached to the base at a position adapted to the hindfoot to contact skin overlaying the medial and lateral plantar nerves; a second electrode attached to the base at a position adapted to the forefoot to contact skin overlaying a plurality of branches of the medial or lateral plantar nerves in the forefoot; and a first and second electrical lead attached to the first and second electrodes, respectively, for treatment of urinary incontinence, comprising: applying the electrode-containing device to a plantar surface of foot of a patient in need of such treatment, wherein the electrode-containing device is attached to a pulse generator external to the electrode-containing device comprising a connector for connecting the pulse generator to the device; and stimulating the patient's foot with the device with pulses of between 1-100 V, preferably about 60 V, and 1-100 mA, having a pulsewidth of 0.01-3 ms, at from 1-50 Hz, preferably about 5 Hz, thereby stimulating the dorsal intermediate and medial cutaneous nerves, deep peroneal nerve, sural nerve, and/or saphenous nerve of the patient.

While the present invention has been described in terms of the above examples and detailed description, those of ordinary skill will understand that alterations may be made within the spirit of the invention. Accordingly, the above should not be considered limiting, and the scope of the invention is defined by the appended claims.

What is claimed is:

1. A method of treating a urological or gastrointestinal disorder in a patient, comprising:
    stimulating a patient's foot, through an electrode-containing device comprising:
        a base adapted to cover a portion of a plantar surface of a human foot including a portion of the forefoot overlaying a plurality of branches of the medial or lateral plantar nerves and a portion of the hindfoot overlaying the medial and lateral plantar nerves;
        a cathode electrode attached to the base at a position adapted to the hindfoot to contact skin overlaying the medial and lateral plantar nerves;
        an anode electrode attached to the base at a position adapted to the forefoot to contact skin overlaying a plurality of branches of the medial or lateral plantar nerves in the forefoot, the anode overlaying at least 50% of the width of the plantar surface of the patient's foot at the forefoot; and
        first and second electrical leads attached to the anode and cathode electrodes, respectively,
    wherein the patient's foot is stimulated with electrical pulses having a pulsewidth of 0.01-3 ms, at between 1-100 V and 1-100 mA, at a frequency of 1-50 Hz, thereby stimulating either the lateral and/or medial plantar nerves or the dorsal intermediate and medial cutaneous nerves, deep peroneal nerve, sural nerve, and/or saphenous nerves of the patient; and
    administering to the patient one or more of:
        an anti-muscarinic compound;
        a serotonin reuptake inhibitor;
        a serotonin receptor antagonist; and
        an opioid drug.

2. The method of claim 1, in which the urological or gastrointestinal disorder is one or more of: overactive bladder (OAB) symptoms including bladder overactivity, urinary frequency, urinary urgency, urinary incontinence; interstitial cystitis (IC); urinary retention; pelvic pain; fecal incontinence; irritable bowel syndrome (IBS); and constipation.

3. The method of claim 2, in which the urinary incontinence is bedwetting, and wherein the device delivers pulses of a frequency of 5 Hz, 0.2 ms pulsewidth, from greater than 0 mA to 100 mA, and from 2-6 times a toe twitch threshold of a patient.

4. The method of claim 1, wherein the patient's foot is stimulated for at least 30 minutes.

5. The method of claim 1, wherein the patient's foot is stimulated for at least 180 minutes.

6. The method of claim 1, wherein the anti-muscarinic compound is selected from the group consisting of atropine, benztropine, biperiden, ipratropium, oxitropium, tiotropium, glycopyrrolate, oxybutynin, tolterodine, chlorpheniramine, diphenhydramine, dimenhydrinate, orphenadrine, trihexyphenidyl, and dicyclomine.

7. The method of claim 6, wherein the anti-muscarinic compound is tolterodine.

8. The method of claim 6 wherein the anti-muscarinic compound is administered at between 0.003 and 1 mg/kg and is administered orally or parenterally.

9. The method of claim 1, wherein the serotonin reuptake inhibitor is selected from the group consisting of alaproclate, citalopram, dapoxetine, escitalopram, femoxetine, fluoxetine, fluvoxamine, ifoxetine, indalpine, omiloxetine, panuramine, paroxetine, pirandamine, duloxetine, sertraline, and zimelidine and the serotonin receptor antagonist is selected from the group consisting of alprenolol, AV-965, BMY-7,378, cyanopindolol, dotarizine, flopropione, GR-46,611, isodocyanopindolol, isamoltane, lecozotan, methiothepin, methysergide, MPPF, NAN-190, oxprenolol, pindobind, pindolol, propranolol, risperidone, robalzotan, SB-649,915 (which acts as both a reuptake inhibitor and a receptor antagonist), SDZ-216,525, spiperone, spiramide, spiroxatrine, UH-301, WAY100135, WAY 100635, and xylamidine.

10. The method of claim 1, wherein the serotonin reuptake inhibitor is duloxetine.

11. The method of claim 1, wherein the serotonin receptor antagonist is WAY100635.

12. The method of claim 1, comprising administering both a serotonin reuptake inhibitor and a serotonin receptor antagonist, and wherein the serotonin reuptake inhibitor is duloxetine and the serotonin receptor antagonist is WAY100635 and wherein duloxetine is administered at between 0.003 and 5 mg/kg and WAY100635 is administered at between 0.1 and 1 mg/kg.

13. The method of claim 1, wherein the serotonin reuptake inhibitor or the serotonin receptor antagonist are administered orally or parenterally.

14. The method of claim 1, wherein the opioid drug is selected from the group consisting of tramadol, morphine, codeine, thebaine, diacetylmorphine (morphine diacetate; heroin), nicomorphine (morphine dinicotinate), dipropanoylmorphine (morphine dipropionate), desomorphine, acetylpropionylmorphine, dibenzoylmorphine, diacetyldihydromorphine, hydromorphone, hydrocodone, oxycodone, oxymorphone, ethylmorphine, buprenorphine, fentanyl, pethidine, levorphanol, methadone, dextropropoxyphene, tapentadol, endorphins, enkephalins, dynorphins, and endomorphins.

15. The method of claim 1, wherein the opioid drug is tramadol.

16. The method of claim 1, wherein the opioid drug is administered at between 0.003 and 1 mg/kg, and is administered orally or parenterally.

17. The method of claim 1, wherein the stimulation is delivered at 5 Hz, with a 0.2 ms pulsewidth, thereby providing post-stimulation inhibition of the urological or gastrointestinal disorder.

18. The method of claim 1, wherein the stimulation is delivered at six times a toe twitch threshold of the patient.

* * * * *

UNITED STATES PATENT AND TRADEMARK OFFICE
CERTIFICATE OF CORRECTION

PATENT NO. : 11,794,009 B2
APPLICATION NO. : 17/318110
DATED : October 24, 2023
INVENTOR(S) : Changfeng Tai It is certified that error appears in the above-identified patent and that said Letters Patent is hereby corrected as shown below:

On the Title Page

Column 2, Item (56) U.S. Patent Documents, Line 2, delete "Iss" and insert -- Liss --

Column 2, Item (57) Abstract, Line 6, delete "and/or and" and insert -- and/or --

In the Specification

Column 4, Line 66, delete "isodocyanopindolol" and insert -- iodocyanopindolol --

Column 25, Line 33, delete "isodocyanopindolol" and insert -- iodocyanopindolol --

Column 43, Line 9, delete "isodocyanopindolol" and insert -- iodocyanopindolol --

Column 46, Line 19, delete "isodocyanopindolol" and insert -- iodocyanopindolol --

In the Claims

Column 49, Line 20, Claim 9, delete "isodocyanopindolol" and insert -- iodocyanopindolol --

Signed and Sealed this
Thirteenth Day of February, 2024

Katherine Kelly Vidal
*Director of the United States Patent and Trademark Office*